United States Patent
Wyss-Coray et al.

(10) Patent No.: US 11,891,442 B2
(45) Date of Patent: Feb. 6, 2024

(54) COMPOSITIONS AND METHODS FOR TREATING AGE-RELATED DISEASES

(71) Applicants: THE BOARD OF TRUSTEES OF THE LELAND STANFORD JUNIOR UNIVERSITY, Stanford, CA (US); THE UNITED STATES GOVERNMENT AS REPRESENTED BY THE DEPARTMENT OF VETERANS AFFAIRS, Washington, DC (US)

(72) Inventors: Anton Wyss-Coray, Palo Alto, CA (US); John Vincent Pluvinage, Atherton, CA (US); Michael C. Bassik, Stanford, CA (US); Michael Haney, Stanford, CA (US); Benjamin Smith, Stanford, CA (US); Carolyn Bertozzi, Stanford, CA (US)

(73) Assignees: THE BOARD OF TRUSTEES OF THE LELAND STANFORD JUNIOR UNIVERSITY, Stanford, CA (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 16/956,339

(22) PCT Filed: Dec. 21, 2018

(86) PCT No.: PCT/US2018/067250
§ 371 (c)(1),
(2) Date: Jun. 19, 2020

(87) PCT Pub. No.: WO2019/126725
PCT Pub. Date: Jun. 27, 2019

(65) Prior Publication Data
US 2020/0317778 A1    Oct. 8, 2020

Related U.S. Application Data

(60) Provisional application No. 62/672,420, filed on May 16, 2018, provisional application No. 62/609,961, filed on Dec. 22, 2017.

(51) Int. Cl.
*C07K 16/28* (2006.01)
*A61P 25/28* (2006.01)
(Continued)

(52) U.S. Cl.
CPC .......... *C07K 16/2803* (2013.01); *A61K 38/47* (2013.01); *A61K 39/001113* (2018.08);
(Continued)

(58) Field of Classification Search
CPC ...... A61K 39/001113; A61K 2039/505; A61K 2039/54; A61K 38/47; A61K 39/3955;
(Continued)

(56) References Cited

U.S. PATENT DOCUMENTS 6,664,235 B1   12/2003  Kanie et al.
6,812,332 B2   11/2004  Johnson et al.
(Continued)

FOREIGN PATENT DOCUMENTS

WO   WO 2008066854 A2   6/2008
WO   WO 2009082488 A2   7/2009
(Continued)

OTHER PUBLICATIONS

Dörner et al., Arthritis Research and Therapy 2006; 8:R74 (Year: 2006).*
(Continued)

*Primary Examiner* — Kimberly Ballard
*Assistant Examiner* — Stacey N Macfarlane
(74) *Attorney, Agent, or Firm* — Casimir Jones, S.C.; Kirk J. Hogan

(57) ABSTRACT

Provided herein are compositions, methods, kits and systems for treating cells, tissues and subjects to alter age-
(Continued)

related biology (e.g., to study or to treat age-related diseases and conditions). In particular, provided herein are compositions, methods, and uses for inhibition or modification of sialic acid or its cognate receptor to restore phagocytosis in aged cells.

7 Claims, 44 Drawing Sheets

Specification includes a Sequence Listing.

(51) Int. Cl.
| | |
|---|---|
| *A61K 39/395* | (2006.01) |
| *A61K 39/00* | (2006.01) |
| *A61K 38/47* | (2006.01) |
| *C12N 9/24* | (2006.01) |
| *A61K 47/68* | (2017.01) |
| *A61M 25/00* | (2006.01) |

(52) U.S. Cl.
CPC ...... *A61K 39/3955* (2013.01); *A61K 47/6815* (2017.08); *A61K 47/6849* (2017.08); *A61P 25/28* (2018.01); *C12N 9/2402* (2013.01); *C12Y 302/01018* (2013.01); *A61K 2039/505* (2013.01); *A61M 25/0097* (2013.01); *C07K 2317/76* (2013.01); *C07K 2317/77* (2013.01)

(58) Field of Classification Search
CPC ............ A61K 47/6815; A61K 47/6849; A61K 39/00; A61P 25/28; C07K 2317/76; C07K 16/2803; C07K 2317/77; C07K 14/70503; C07K 2317/70; C12N 9/2402; C12N 2740/16044; C12Y 302/01018; A61M 25/0097

See application file for complete search history.

(56) References Cited

U.S. PATENT DOCUMENTS

| | | |
|---|---|---|
| 8,114,062 B2 | 2/2012 | Muni et al. |
| 9,493,575 B2 | 11/2016 | Siddhartha et al. |
| 2005/0031651 A1 | 2/2005 | Gervais et al. |
| 2005/0256207 A1 | 11/2005 | McGrath et al. |

FOREIGN PATENT DOCUMENTS

| | | |
|---|---|---|
| WO | WO 2013090857 A1 | 6/2013 |
| WO | WO 2019126725 | 6/2019 |

OTHER PUBLICATIONS

ClinicalTrials.gov Identifier: NCT00382837, published online with last update May 21, 2014 (Year: 2014).*
Trysberg and Tarkowski, Cerebral inflammation and degeneration in systemic lupus erythmatosus, Current Opinion in Rheumatology, 16:527-533, 2004 (Year: 2004).*
Carnahan et al., Clinical Cancer Research, Epratuzumab, a Humanized Monoclonal Antibody Targeting CD22, 9(10); 2003 (Year: 2003).*
Bohlen et al., "Diverse Requirements for Microglial Survival, Specification, and Function Revealed by Defined-Medium Cultures". Neuron. May 17, 2017;94(4):759-773.
Cabral et al., The phagocytic capacity and immunological potency of human dendritic cells is improved by a2,6-sialic acid deficiency. Immunology, 2012, vol. 138, pp. 235-245; abstract.
Coughlin et al., "An extracatalytic function of CD45 in B cells is mediated by CD22". Proc Natl Acad Sci U S A. Nov. 24, 2015;112(47):E6515-24.
Ereño-Orbea et al., "Molecular basis of human CD22 function and therapeutic targeting". Nat Commun. Oct. 2, 2017;8(1):764.
International search Report and Written Opinion issued for corresponding Application No. PCT/US2018/067250 dated May 23, 2019, 22 pages.
Macauley et al., "Siglec-mediated regulation of immune cell function in disease". Nat Rev Immunol. Oct. 2014;14(10):653-66.
Mott et al., "Neuronal expression of CD22: novel mechanism for inhibiting microglial proinflammatory cytokine production". Glia. May 2004;46(4):369-79.
Müller et al., "The role of CD22 and Siglec-G in B-cell tolerance and autoimmune disease". Nat Rev Rheumatol. Jul. 2014;10(7):422-8.
Miyagi et al., "Mammalian sialidases: physiological and pathological roles in cellular functions". Glycobiology. Jul. 2012;22(7):880-96.
Nitschke et al., "CD22 is a negative regulator of B-cell receptor signaling", Current Biology, 1997, vol. 7, No. 2, p. 133-143; abstract; p. 134, col. 2 para. 2.
Salter et al., "Microglia emerge as central players in brain disease". Nat Med. Sep. 8, 2017;23(9):1018-1027.

* cited by examiner

FIG. 1 Continued
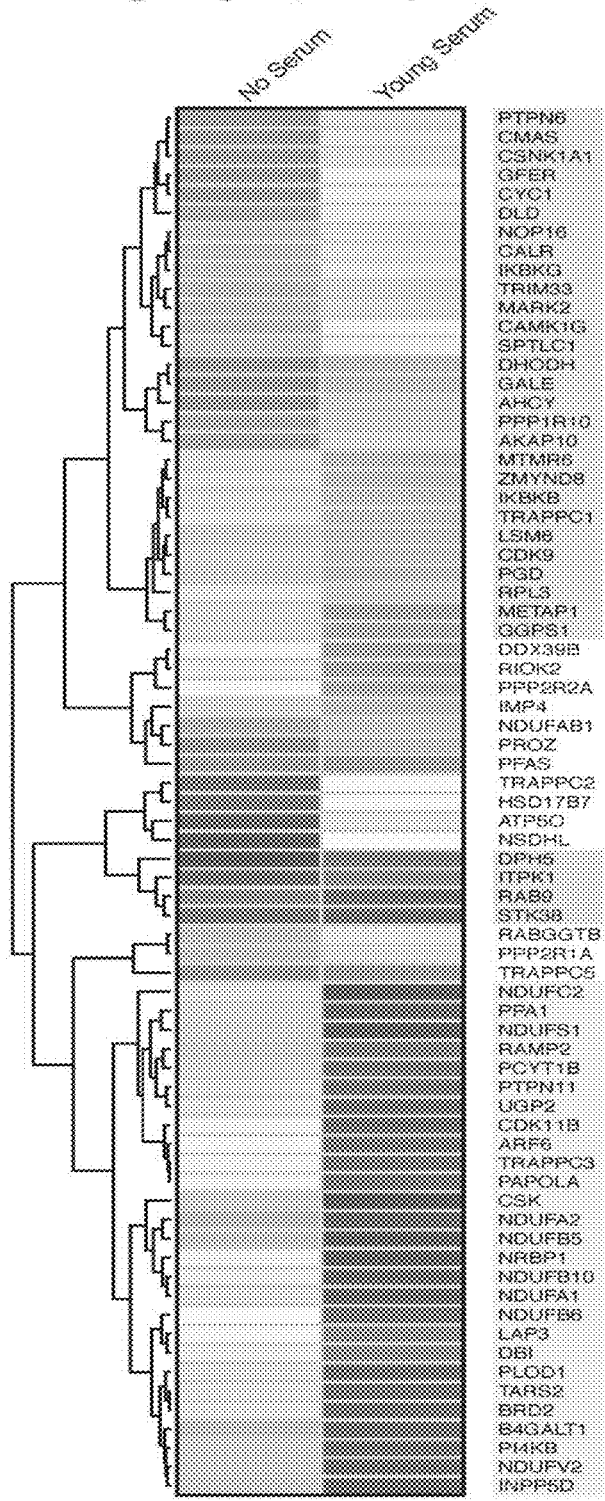
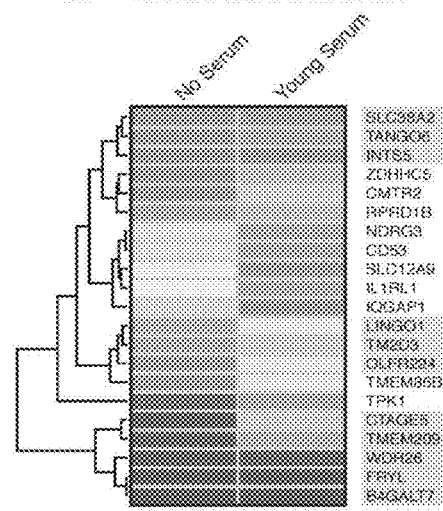

FIG. 13
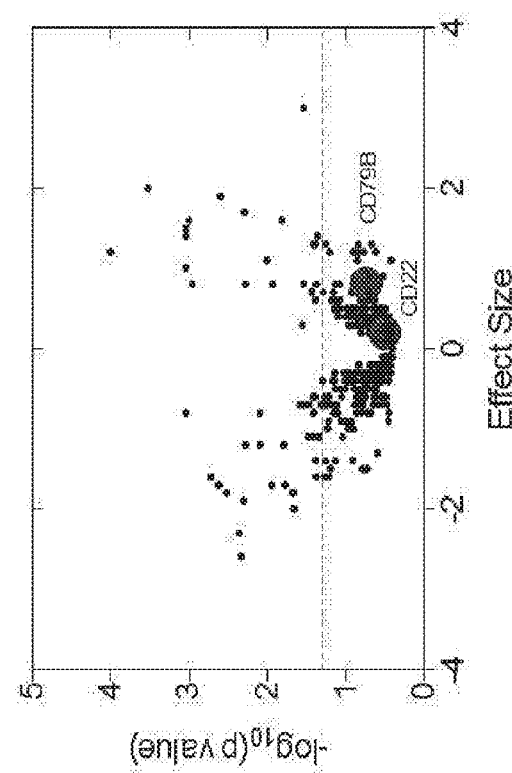
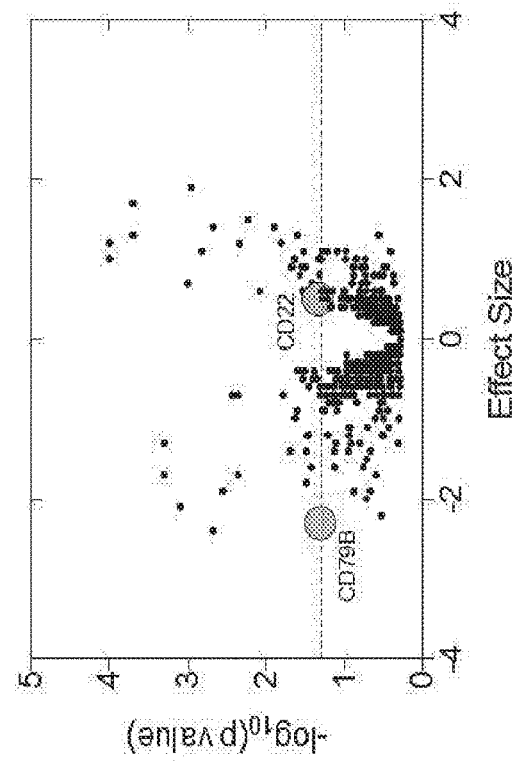

FIG. 20
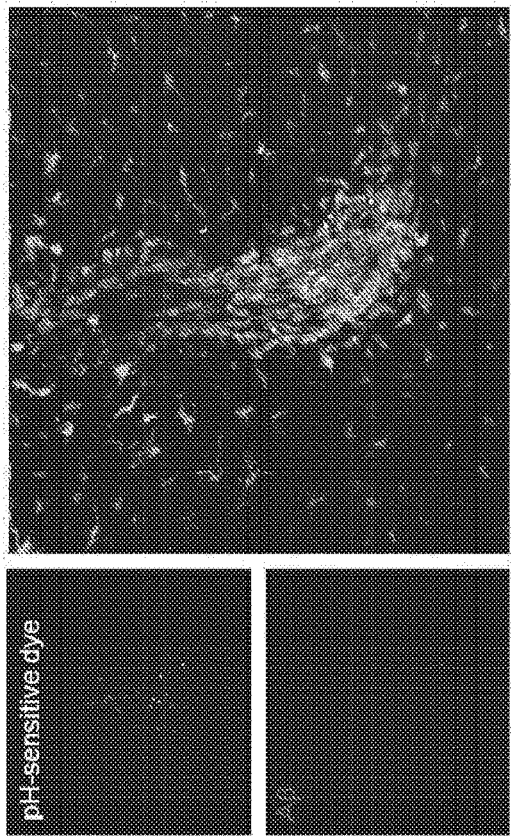
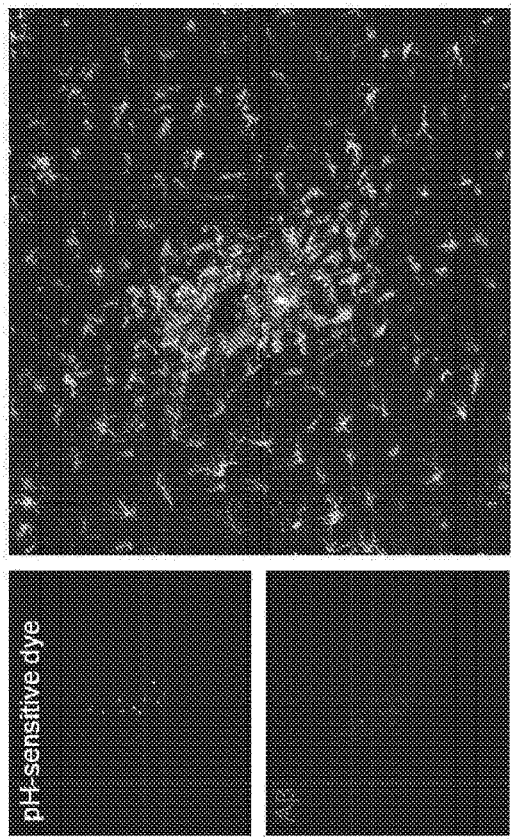

FIG. 32
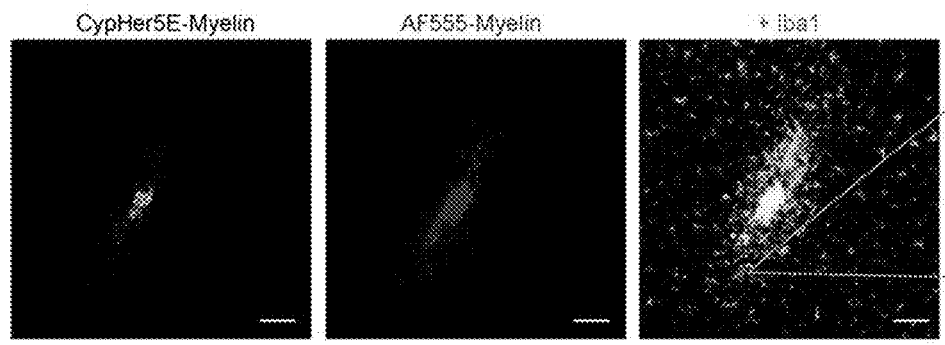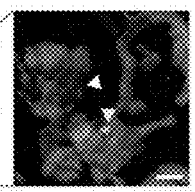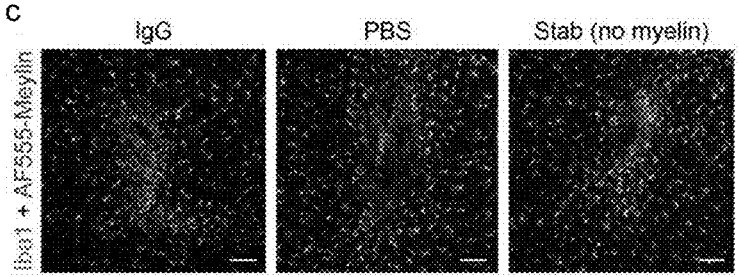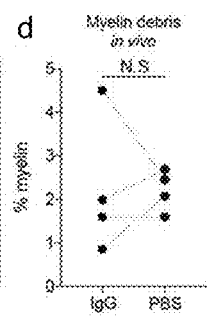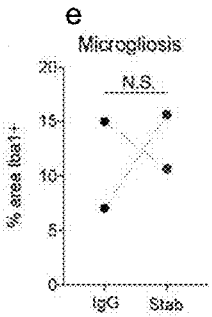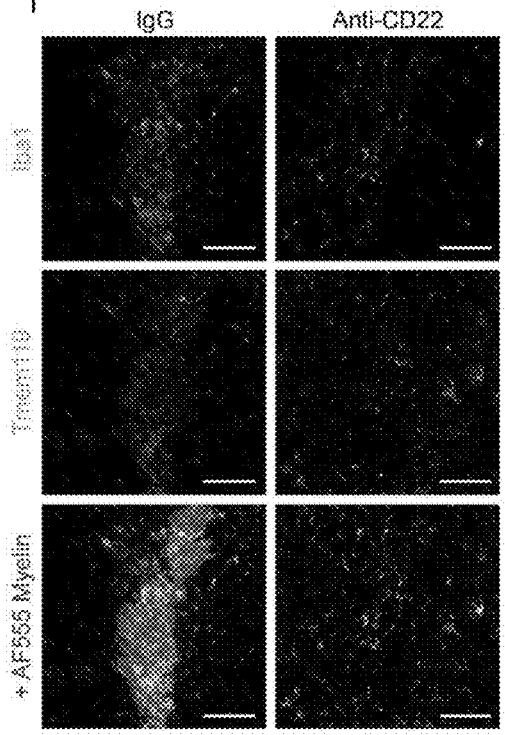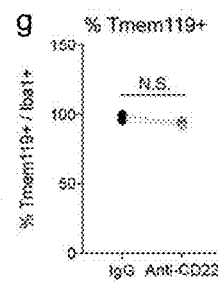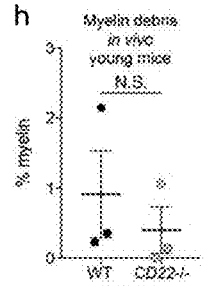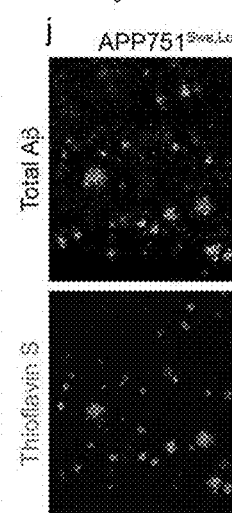

FIG. 33
a
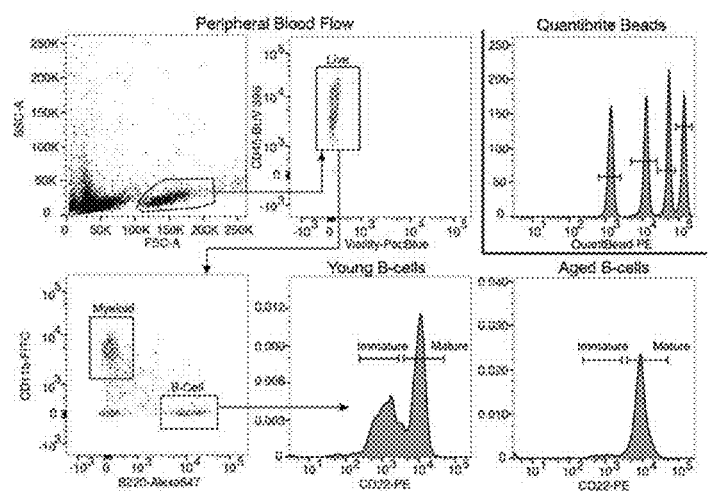
b
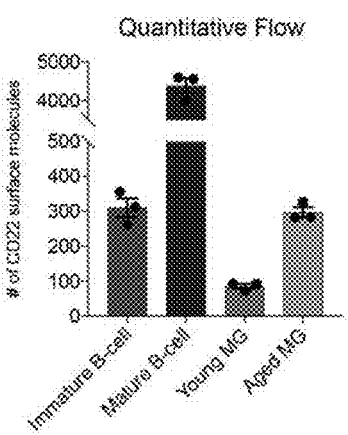
c 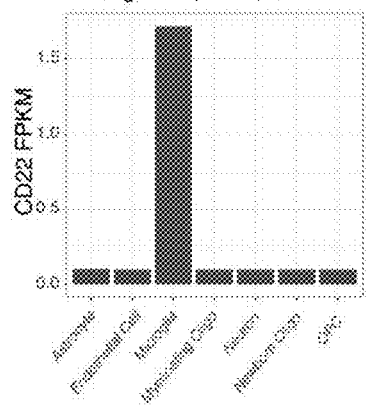
d 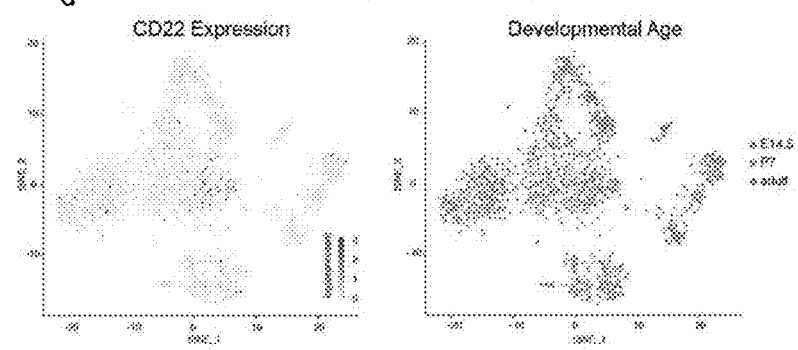
e 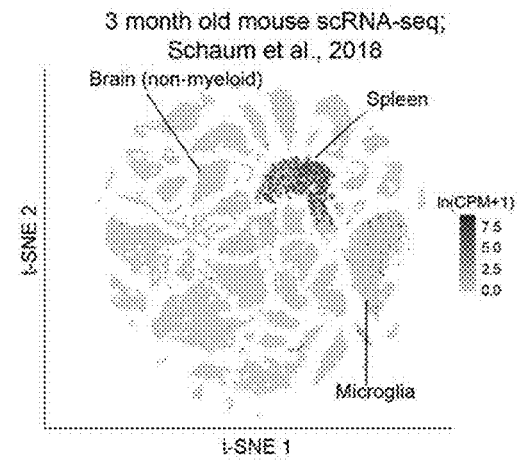
f 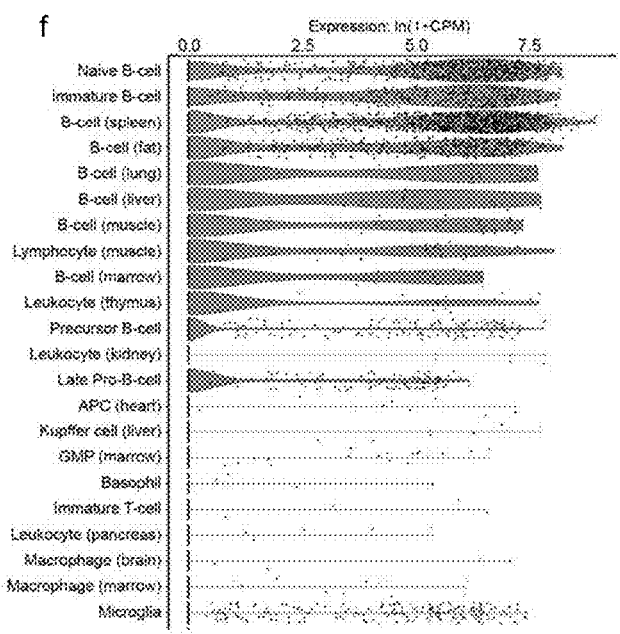

```
                      SEQUENCE LISTING

<160> NUMBER OF SEQ ID NOS: 6

<210> SEQ ID NO 1
<211> LENGTH: 18
<212> TYPE: DNA
<213> ORGANISM: Artificial sequence
<220> FEATURE:
<223> OTHER INFORMATION: Synthetic

<400> SEQUENCE: 1
gtttcagaac ttcttcga                                                 18

<210> SEQ ID NO 2
<211> LENGTH: 19
<212> TYPE: DNA
<213> ORGANISM: Artificial sequence
<220> FEATURE:
<223> OTHER INFORMATION: Synthetic

<400> SEQUENCE: 2
gaggcgccat cagtttcga                                                19

<210> SEQ ID NO 3
<211> LENGTH: 17
<212> TYPE: DNA
<213> ORGANISM: Artificial sequence
<220> FEATURE:
<223> OTHER INFORMATION: Synthetic

<400> SEQUENCE: 3
gacacgtggc ttcggct                                                  17

<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
```

```
ggtgatggag gtgacagaag                                              20

<210> SEQ ID NO 5
<211> LENGTH: 21
<212> TYPE: DNA
<213> ORGANISM: Artificial sequence
<220> FEATURE:
<223> OTHER INFORMATION: Synthetic

<400> SEQUENCE: 5
ccactcctca ggccagaaac t                                            21

<210> SEQ ID NO 6
<211> LENGTH: 20
<212> TYPE: DNA
<213> ORGANISM: Artificial sequence
<220> FEATURE:
<223> OTHER INFORMATION: Synthetic

<400> SEQUENCE: 6
tgccgatggt ctctggactg                                              20
```

COMPOSITIONS AND METHODS FOR TREATING AGE-RELATED DISEASES

The present application is a 371 U.S. National Phase Entry of pending International Application No. PCT/US2018/067250 filed Dec. 21, 2018, which claims priority to U.S. Provisional Patent Application Ser. No. 62/609,961 filed Dec. 22, 2017, and to U.S. Provisional Patent Application Ser. No. 62/672,420 filed May 16, 2018, each of which is incorporated by reference in its entirety herein.

This invention was supported by Grant Nos. R01-AG045034 and DP1-AG053015 awarded by the National Institutes of Health, and by the U.S. Veteran's Administration. The U.S. government has certain rights in the invention.

FIELD

Provided herein are compositions, methods, kits and systems for treating cells, tissues and subjects to alter age-related biology (e.g., to study or to treat age-related diseases and conditions). In particular, provided herein are compositions, methods, and uses for inhibition or modification of sialic acid or its cognate receptor to restore phagocytosis in aged cells.

BACKGROUND

Brain-resident microglia, peripheral macrophages and other cell types maintain homeostasis through phagocytic clearance of pathogens, apoptotic cells, and debris[1-3]. This process deteriorates with normal ageing and age-related disease, but is restored by exposure to a young environment[4,5]. Aberrant phagocytosis contributes to the pathogenesis of various age-related diseases including frontotemporal dementia[6], age-related macular degeneration, atherosclerosis, cancer and Alzheimer's disease[7]. Many of the pathological features found in the brains of patients with neurodegenerative disorders are also seen in clinically-unimpaired age-matched adults[8]. In particular, microglia in the aged brain are dystrophic, hypo-motile and burdened with lysosomal deposits indicative of impaired phagocytic degradation of debris[9-12].

A strategy to reverse this decline is heterochronic parabiosis[13]. By connecting the circulations of young and aged animals, or by direct infusion of young plasma, exposure to a young systemic environment rejuvenates multiple aged tissues including the brain[14-17]. In turn, young serum restores the phagocytic function of tissue resident macrophages from aged animals[5], and phagocyte rejuvenation is partially responsible for these beneficial organismal effects[18]. Parabiosis and transfusion of serum have many disadvantages including acquisition and compensation of donors, complications of surgery and blood-letting, transmission of infection, cost, inconvenience, consumption of time, complications of sample labeling, shipment and storage, decline in serum constituents over time, lack of potent and specific effects on phagocyte rejuvenation, and diverse and life-threatening transfusion reactions. Accordingly, compositions and methods for restoring phagocytosis in aged macrophages, microglia and other cells, for example, retinal pigment epithelial cells, are needed.

SUMMARY

Provided herein are compositions, methods, kits and systems for treating cells, tissues and subjects to alter age-related biology (e.g., to study or to treat age-related diseases and conditions). In particular, provided herein are compositions, methods, and uses for inhibition or modification of sialic acid or its cognate receptor to restore phagocytosis in aged cells.

For example, provided herein are methods of treating an age-related disease or condition, comprising exposing one or more of a subject's microglia, macrophage and/or other phagocytic cells to a CD22 inhibitor wherein the exposing treats the age-related disease or condition. In certain embodiments, the exposing to the CD22 inhibitor increases phagocytosis by the one or more of the subject's microglia, macrophage and/or other phagocytic cells. In some embodiments, the subject is a human subject. In particular embodiments, the age-related disease or condition is selected from the group consisting of, for example, dementia, frontotemporal dementia, Parkinson's disease, Alzheimer's disease, chronic obstructive pulmonary disease, macular degeneration amyotrophic lateral sclerosis, Huntington's disease, Nasu-Hakola disease, stroke, rheumatoid arthritis, osteoarthritis, tuberculosis, malaria, Behcet's disease, systemic lupus erythematosus, central nervous system (CNS) lupus, granulomatous disease, sarcoidosis, spinal cord injury, traumatic brain injury, lysosomal storage diseases, (Niemann-Pick disease, Niemann-Pick disease Type C, Fabry disease, Gaucher disease, Tay-Sachs disease, Krabbe disease, metachromatic leukodystrophy, Hurler syndrome, Hunter syndrome), multiple system atrophy, Lewy body dementia, lymphocytic choriomeningitis virus infection, viral and bacterial infections of the CNS, retinitis pigmentosa, Paget disease, pulmonary fibrosis, Smith-Lemil-Opitz syndrome, Tay-Sachs, Niemann-Pick's, Sjögren's syndrome, scleroderma, Goodpasture syndrome, glomerulonephritis, bullous pemphigoid, pemphigous vulgaris, schizophrenia, major depressive disorder, bipolar disorder, anorexia nervosa, obsessive compulsive disorder, general anxiety disorder, hematogenous neoplasia, and solid tumors of the periphery and CNS. In other embodiments, the age-related disease or condition is selected from the group consisting of atherosclerosis and cancer. In certain embodiments, the CD22 inhibitor is an anti-CD22 antibody. In other embodiments, the CD22 inhibitor is a CD22 antagonist. In further embodiments, the CD22 antagonist is selected from the group consisting of a small molecule, a peptide, and a nucleic acid, for example, an allele specific oligonucleotide (ASO) nucleic acid. In certain embodiments, the small molecule is NSC-87877 (CAS No. 56990-57-9) or derivatives and analogs thereof (see e.g., U.S. Patent Application Publication No. 2008017309, incorporated herein by reference in its entirety). In other embodiments, the small molecule is 3Fax-Neu5Ac (e.g., CAS 117405-58-0). In particular embodiments, the small molecule inhibitor is a multivalent conjugate. In specific embodiments, the multivalent conjugate comprises a glycan component and/or a glycomimetic component. In further embodiments, the multivalent conjugate is a neoglycoprotein, a glycopolymer, a glycol-liposome, or a nanoparticle. In still further embodiments, the small molecule blocks ligand engagement with CD22. In additional embodiments, the small molecule is an antagonist of CD22 signaling downstream of ligand attachment. In some embodiments, the CD22 inhibitor is a combination of the aforementioned embodiments. In specific embodiments, the CD22 inhibitor interferes with CD22 expression. In still further embodiments, the exposing is in vivo exposing, ex vivo exposing or in vitro exposing. In additional embodiments, the exposing to the CD22 inhibitor is selected from the group consisting of local administration, topical administration, intrathecal administration, intraparenchymal administration, intracerebroventricular administration, intravenous administration, intraarterial administration, intrapulmonary administration and oral administration. In some embodiments, the exposing comprises combination therapy with an agent that interferes with β-amyloid expression and accumulation. In other embodiments, the exposing comprises combination therapy with an agent that interferes with tau expression and accumulation. In some embodiments, the exposing comprises combination therapy with an intervention that treats a cancer-related disease or condition.

As well, provided herein are methods of treating an age-related disease or condition, comprising exposing one or more of a subject's microglia, macrophage and/or other phagocytic cells to an agent that decreases cell surface sialic acid wherein the exposing treats said age-related disease or condition. In some embodiments, the exposing to the agent that decreases cell surface sialic acid increases phagocytosis by the one or more of the subject's microglia, macrophage and/or other phagocytic cells. In particular embodiments, the subject is a human subject. In certain embodiments, the age-related disease or condition is selected from the group consisting of dementia, frontotemporal dementia, Parkinson's disease, Alzheimer's disease, chronic obstructive pulmonary disease, macular degeneration, macular degeneration, amyotrophic lateral sclerosis, Huntington's disease, Nasu-Hakola disease, stroke, rheumatoid arthritis, osteoarthritis, tuberculosis, malaria, Behcet's disease, systemic lupus erythematosus, central nervous system (CNS) lupus, granulomatous disease, sarcoidosis, spinal cord injury, traumatic brain injury, lysosomal storage diseases, retinitis pigmentosa, Paget disease, Tay-Sachs, Niemann-Pick's, Sjögren's syndrome, scleroderma, Goodpasture syndrome, glomerulonephritis, bullous pemphigoid, pemphigous vulgaris, schizophrenia, major depressive disorder, bipolar disorder, anorexia nervosa, obsessive compulsive disorder, general anxiety disorder, hematogenous neoplasia, and solid tumors of the periphery and CNS. In other embodiments, the age-related disease or condition is selected from the group consisting of atherosclerosis and cancer. In certain embodiments, the agent that decreases cell surface sialic acid is a sialidase. In additional embodiments, the sialidase is a *Vibrio cholera, Streptococcus thermophilus, Arthrobacter ureafaciens, Clostridium perfringens, Mus musculus, Homo sapiens*, Coronaviridae, or influenza sialidase. In other embodiments, the sialidase is a recombinant sialidase. In specific embodiments, the sialidase is a protein or peptide with silaidase activity. In additional embodiments, the agent that decreases cell surface sialic acid is a sialic acid antagonist. In specific embodiments, the sialic acid antagonist is a small molecule. In some embodiments, the sialic acid antagonist contains a biphenylcarbonyl moiety. In other embodiments, the sialic acid antagonist is metabolized to a fluorinated sialic acid. In different embodiments, the sialic acid antagonist is 5-(acetylamino)-3,5-dideoxy-3-fluoro-D-erythro-α-L-manno-2-nonulopyranosonic acid. In further embodiments, the sialic acid antagonist interferes with sialic acid expression. In still further embodiments, the exposing to the agent that decreases cell surface sialic acid is selected from the group consisting of local administration, topical administration, intrathecal administration, intraparenchymal administration, intracerebroventricular administration, intravenous administration, intraarterial administration, intrapulmonary administration and oral administration. In other embodiments, the exposing comprises combination therapy with an agent that interferes with β-amyloid expression. In some embodiments, the exposing comprises combination therapy with an intervention that treats a cancer-related disease or condition.

Moreover, provided herein are methods of treating of treating a cell, a tissue, or a subject having, for example, an age-related disease or condition and/or a neurodegenerative disease or condition, comprising exposing one or more microglia, macrophage and/or other phagocytic cells to a CD22 inhibitor and an agent that decreases cell surface sialic acid, for example, wherein the exposing treats the age-related disease or condition, or the neurodegenerative disease or condition.

In addition, provided herein are methods of preventing or reversing microglia, macrophage or other phagocytic cell ageing in a subject's tissue or cell, comprising down-regulating gene expression of CD22, and/or decreasing cell surface sialic acid.

In turn, provided herein are methods of treating an age-related and/or neurodegenerative disease in a subject, comprising assaying a microglia, macrophage and/or other phagocytic cell sample from the subject for the presence of CD22 and/or sialic acid, and administering an agent that decreases CD22 and/or sialic acid.

Further embodiments provide a composition, kit and/or system comprising a CD22 inhibitor and an agent that decreases cell surface sialic acid.

Also provided herein is use of a CD22 inhibitor and/or an agent that decreases sialic acid to study or to treat an age-related disease or condition.

Provided herein are methods of treating an age-related disease or condition and/or a neurodegenerative disease or condition, comprising: exposing one or more of a subject's microglia, macrophage and/or other phagocytic cells to a CMAS (CMP-Neu5Ac synthase) inhibitor and an agent that decreases cell surface sialic acid wherein said exposing treats said age-related disease or condition, or the neurodegenerative disease or condition.

Also provided herein are methods of preventing or reversing microglia, macrophage and/or other phagocytic cell ageing in a subject, comprising down-regulating gene expression of CMAS, and/or decreasing cell surface sialic acid.

In addition, provided herein are methods of treating an age-related and/or neurodegenerative disease in a subject, comprising assaying a microglia, macrophage and/or other phagocytic cell sample from said subject for the presence of CMAS and/or sialic acid, and administering an agent that decreases activity and/or sialic acid.

Further embodiments provide a composition, comprising a CMAS inhibitor, and an agent that decreases cell surface sialic acid.

Also provided herein is use of a CMAS inhibitor and/or an agent that decreases sialic acid to study or to treat an age-related disease or condition.

Provided herein are compositions, methods, kits and systems for promoting the clearance of myelin debris, amyloid oligomers and alpha-synuclein in vivo comprising blocking CD22, an age-dependent regulator of phagocytosis, and/or blocking the sialic acid/CD22/SHP1 pathway. In some embodiments, CD22 is blocked with a function- and/or ligand-blocking antibody. In additional embodiments, CD22 is blocked with a protein, a small molecule, and/or an aptamer. In another embodiment, CD22 is blocked by an antisense molecule, a small RNA, or other disruptor of CD22 gene expression. In further embodiments, the sialic acid/CD22/SHP1 pathway is blocked by an inhibitor of SHP phosphatases, and/or by a compound that targets one or more sialic acid ligands. In certain embodiments, a CD22 blocking antibody is delivered to the central nervous system by an osmotic pump and restores microglial homeostasis and cognitive function in aging mammals. In other embodiments, the mammal is a murine or human mammal. In still further embodiments, CD22 modulates CCL3 and promotes cognitive improvement. In given embodiments, compositions and methods comprising SHP1 and CCL3 inhibitor, and/or inhibitors of CCL3 receptors (e.g., CCR1-5) promote phagocytosis.

Also provided herein are methods and compositions for use of CD22 as a biomarker, for example as a cerebrospinal fluid (CSF) biomarker of Alzheimer's disease (AD).

In some embodiments, the present invention provides a kit comprising a CD22 antagonist, a solution for reconstitution and dilution of said CD22 antagonist, and a CD22 antagonist administration vessel, a needle, a catheter and a catheter connection locking hub.

In some embodiments, the present invention provides a system for administration of a CD22 antagonist comprising a CD22 antagonist, at least one component configured for CD22 antagonist reconstitution and dilution, at least one component configured for parenteral or enteral administration of said CD22 antagonist comprising one or more of a CD22 antagonist administration vessel, a needle, a catheter, a catheter connection locking hub, and a volumetric CD22 antagonist pump.

In some embodiments, the present invention provides a method of treating a neurodegenerative disease or condition comprising exposing one or more of a subject's microglia, macrophage and/or other phagocytic cells to a CD22 inhibitor wherein the exposing treats the neurodegenerative condition. In certain embodiments the exposing to the CD22 inhibitor increases phagocytosis by the one or more of said subject's microglia, macrophage and/or other phagocytic cells. In other embodiments, the subject is a human. In further embodiments, neurodegenerative disease or condition is Niemann-Pick disease Type C (NPC). In still further embodiments the CD22 inhibitor is an anti-CD22 antibody. In additional embodiments, the CD22 inhibitor is a CD22 antagonist. In given embodiments, the CD22 antagonist is selected from the group consisting of a small molecule, a peptide, and a nucleic acid. In particular embodiments, the CD22 inhibitor interferes with CD22 expression. In still further embodiments, the exposing is in vivo exposing, ex vivo exposing or in vitro exposing.

Provided herein are compositions, methods, kits and systems for the treatment of Niemann-Pick disease with a CD22 blocking compound. In some embodiments, the Niemann-Pick disease is Niemann-Pick disease Type C. In certain embodiments, the CD22 blocking compound is an anti-CD22 antibody, an aptamer, an antisense molecule, a small RNA, a protein, a small molecule or other disruptor of CD22 expression. In given embodiments, the CD22 blocking compound is delivered intrathecally, intravenously, parenterally, enterally, by osmotic pump, by electronic pump, intermittently, continuously, and/or by catheter to a subject with NPC. 39.

DESCRIPTION OF THE FIGURES

FIG. 13 shows that cell-surface sialic acid inhibits phagocytosis in a second screen composed of an sgRNA sublibrary that knocks out membrane proteins. Volcano plots show significant glycosylation hits from screening of the no serum-treated (a) and the young serum-treated (b) BV2 cells. The dashed lines indicate the P=0.05 significance cutoff. Green indicates a significant hit, and red indicates "does not pass significance". Knocking out B-cell receptor signaling genes replicates the pro-phagocytic effect of serum.

FIG. 20 shows that CD22 blockade promotes clearance and phagocytosis of Aβ using the histologic methods provided in the description of FIG. 19. 48 hours after injection, mice treated with anti-CD22 showed dramatically increased clearance of oligomeric Aβ compared to control mice.

FIG. 32 shows validation of in vivo phagocytosis assays. (a), Representative images of myelin labeled with a pH-sensitive fluorescent dye (CypHer5E, white), a constitutively fluorescent dye (AF555, red) and stained for Iba1 (green). The majority of AF555 overlapping with Iba1 is also positive for CypHer5E, indicating localization to an acidified compartment. Scale bar=100 microns. (b), 3D reconstruction of microglial cell (Iba1, green) with ingested myelin (CypHer5E and AF555, white and red, yellow arrow) near un-ingested myelin (AF555, red, white arrow). Scale bar=5 microns. (c), Representative images of myelin (red) overlaid with the microglia marker Iba1 (green) at the injection site of IgG (left) or PBS (middle) treated hemispheres of the same aged brain, or an image of a stab wound control (not injected with myelin). Scale bar=100 microns. (d), Clearance of myelin debris in the IgG (black) or PBS (blue) treated hemispheres assessed 48 hours post-injection (n=4, N.S. not significant, paired t-test). (e), Microgliosis, as assessed by % Iba1+ area at the injection site, was not altered by IgG (n=4, N.S. not significant, paired t-test). (f), Representative images of the macrophage marker, Iba1 (cyan, top row), the resident microglia-specific marker, Tmem119 (orange, middle row), or the two markers overlaid with myelin (magenta, bottom row) at the injection site of IgG (left) or anti-CD22 (right) treated hemispheres of the same aged brain. Scale bar=100 microns. (g), Percent of Iba1+ phagocytes expressing Tmem119 at the injection site (n=4, N.S. not significant, paired t-test). (h), Clearance of myelin debris in young WT (black) or CD22−/− (green) mice was assessed 48 hours after injection (n=4, N.S. not significant, t-test). (i), Percent of CypHer5E+ residual Aβ oligomers, indicating localization to acidified lysosomes (n=8, **P<0.005, paired t-test). (j), Representative images of total Aβ (white, top row) or Thioflavin S+ fibrillar Aβ (green, bottom row) in transgenic mice expressing human Aβ P with Swedish and London familial AD mutations (left) or WT mice injected with Aβ oligomers 48 hours prior to analysis (right). (k), Microgliosis, as assessed by % Iba1+ area at the Aβ oligomer injection site, was not altered by CD22 blockade (n=8, N.S. not significant). (l), Microgliosis, as assessed by % Iba1+ area at the α-synuclein fibril injection site, was not altered by CD22 blockade (n=7, N.S. not significant).

FIG. 33 shows CD22 expression in mice and humans. (a), Flow cytometry gating scheme for analysis of CD22 expression in peripheral blood-derived myeloid cells (CD45+CD11b+), immature B-cells (CD45+B220+CD22lo), and mature B-cells (CD45+B220+CD22hi). Quantibrite beads are shown on the top right panel. (b), Quantification of flow cytometry analysis showing the number of CD22 molecules on various cell types, interpolated from the Quantibrite bead standard curve. (c), CD22 expression in various cell types of the mouse CNS, showing exclusive expression in microglia. Data from Barres lab RNA-seq (http://www.brainrnaseq.org/). (d), t-SNE plot showing scRNA-seq analysis of CD22 expression in microglia isolated from E14.5, P7, and adult mouse brains. CD22 is enriched in a subpopulation of P7 microglia. (e), t-SNE plot showing scRNA-seq analysis of CD22 expression in cells from 20 different mouse tissues. CD22 is expressed in B-cells and microglia, but absent from non-myeloid brain cells. (f), Violin plots of log-normalized CD22 counts per million reads (CPM) showing high expression in B-cells from multiple organs and in microglia.

DEFINITIONS

Figure 1:
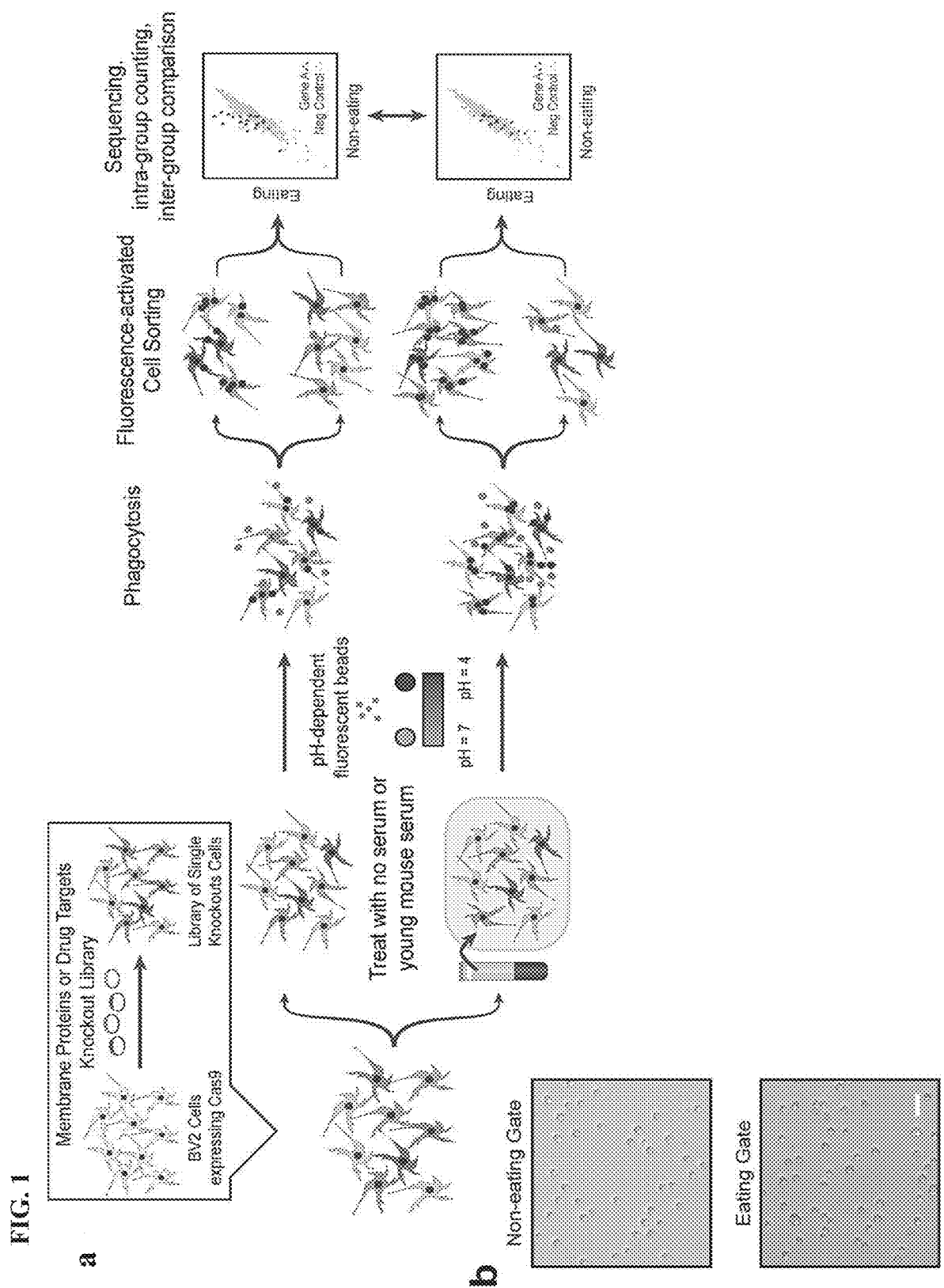
FIG. 1 shows that CRISPR-Cas9 knockout screen identifies young serum modifiers of phagocytosis. (a), Experimental schematic for pooled genetic screen. (b), Confirmation of non-eating (top) and eating (bottom) populations based on microscopic images of sorted cells gated on fluorescence of pH-dependent particle. (c,d), Heatmap with hierarchical clustering of significant hits (FDR<0.1) from Drug Targets, Phosphatases, Kinases Screen and Membrane Proteins Screen. Color gradient represents the following quantification: Sign of Effect Size (+/−)*−Log 10 (p-value). e,f,g,h), Phagocytosis of pH-dependent fluorescent particles monitored over 24 hours for a hit that is necessary for phagocytosis in general (B4GALT7, (e)), a hit that promotes phagocytosis in general (GALE, (f)), a hit that inhibits phagocytosis only in the young serum condition (B4GALT1, (g)), and a hit that promotes phagocytosis only in the no serum condition (PTPN6, (h)). Each experiment was performed 3 independent times in technical triplicate. Data represent mean+/−S.E.M. Normalized phagocytosis=red object area/phase confluence, where phagocytosis by control no serum cells at T0h is set to 0 and phagocytosis by control no serum cells at T24h is set to 1. Scale bar, 50 um.

To facilitate an understanding of the present disclosure, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., Alzheimer's disease, Parkinson's disease, atherosclerosis, cancer). Test compounds comprise both known and potential therapeutic compounds. A test compound can be determined to be therapeutic by screening using the screening methods of the present disclosure.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present disclosure.

As used herein, the term "effective amount" refers to the amount of a compound (e.g., a compound described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, or ex vivo.

As used herein, the term "antigen binding agent (e.g., "antigen-binding protein" or protein mimetic such as an apatamer) refers to proteins that bind to a specific antigen. "Antigen-binding proteins" include, but are not limited to, immunoglobulins, including polyclonal, monoclonal, chimeric, single chain, single domain, scFv, minibody, nanobody, and humanized antibodies, Fab fragments, F(ab')2 fragments, and Fab expression libraries.

As used herein, the term "single-chain variable fragment" (scFv) refers to an antibody fragment that comprises a fusion protein of the variable regions of the heavy ($V_H$) and light chains ($V_L$) of an immunoglobulin. In some embodiments, the $V_H$ and $V_L$ are connected with a short linker peptide.

As used herein, the term "minibody" refers to an antibody fragment that retains antigen binding activity. In some embodiments, minobodies comprise an scFv fused to an Fc region (e.g., an IgG Fc region).

Various procedures known in the art are used for the production of polyclonal antibodies. For the production of antibody, various host animals can be immunized by injection with the peptide or protein containing the desired epitope including but not limited to rabbits, mice, rats, sheep, goats, llamas, alpacas, etc. In a preferred embodiment, the peptide is conjugated to an immunogenic carrier (e.g., diphtheria toxoid, bovine serum albumin (BSA), or keyhole limpet hemocyanin (KLH)). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, Gerbu adjuvant and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, NY). These include, but are not limited to, the hybridoma technique originally developed by Köhler and Milstein (Köhler and Milstein, Nature, 256:495-497 [1975]), as well as the trioma technique, the human B-cell hybridoma technique (See e.g., Kozbor et al., Immunol. Today, 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]). In other embodiments, suitable monoclonal antibodies, including recombinant chimeric monoclonal antibodies and chimeric monoclonal antibody fusion proteins are prepared as described herein.

According to the invention, techniques described for the production of single chain antibodies (U.S. Pat. No. 4,946,778; herein incorporated by reference) can be adapted to produce specific single chain antibodies as desired. An additional embodiment of the invention utilizes the techniques known in the art for the construction of Fab expression libraries (e.g., Huse et al., Science, 246:1275-1281 [1989]) to allow rapid and easy identification of monoclonal Fab fragments with the desired specificity.

In some embodiments, monoclonal antibodies are generated using the ABL-MYC method (See e.g., U.S. Pat. Nos. 5,705,150 and 5,244,656, each of which is herein incorporated by reference) (Neoclone, Madison, WI). ABL-MYC is a recombinant retrovirus that constitutively expresses v-abl and c-myc oncogenes. When used to infect antigen-activated splenocytes, this retroviral system rapidly induces antigen-specific plasmacytomas. ABL-MYC targets antigen-stimulated (Ag-stimulated) B-cells for transformation.

In some embodiments, biopanning as described in Pardon et al., Nat Protoc. 2014 March; 9(3):674-93 is used to generate single domain antibodies. In some embodiments, to generate murine scFv units, phage-based biopanning strategies, of which there are several published protocols available, are used.

Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

Genes encoding antigen-binding proteins can be isolated by methods known in the art. In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, phage display biopanning, and immunoelectrophoresis assays, etc.)

As used herein, the term "toxic" refers to any detrimental or harmful effects on a cell or tissue as compared to the same cell or tissue prior to the administration of the toxicant.

DETAILED DESCRIPTION OF THE DISCLOSURE

Provided herein are compositions, methods, kits and systems for treating cells, tissues and subjects to alter age-related biology (e.g., to study or to treat age-related diseases and conditions). In particular, provided herein are compositions, methods, and uses for inhibition or modification of sialic acid or its cognate receptor to restore phagocytosis in aged cells.

In experiments conducted in the course of development of certain embodiments of the present invention, CRISPR-Cas9 knockout screens[19-23] were used as a drug target identification platform with previous success in small molecule target identification[24]. As an alternative to isolating pro-phagocytic factors from the heterogeneous milieu of young serum, genes in microglia necessary for receiving and transducing signals from these factors were identified. Because serum borne factors promoting phagocytosis are potential signals through pathways comprising transmembrane proteins that transduce ligand-receptor interactions with downstream kinases and phosphatases, libraries of single-guide RNAs (sgRNAs) targeting ~1,000 genes coding for transmembrane proteins and ~2,000 genes coding for kinases, phosphatases, and drug targets, along with ~3,000 negative control sgRNAs[25], were designed. Additional drug targets were annotated to identify druggable genes whereby pre-validated pharmacological interventions are repurposed to promote phagocytosis.

Cas9-expressing BV2 cells, a mouse microglia-derived cell line[26], were infected with a pool of sgRNAs to obtain a population of single-knockout cells for every gene represented in the sgRNA library (FIG. 1a). One population of the pooled knockout cells was treated with medium containing young mouse serum, and another population with serum-free medium. After 24 hours of young serum or serum-free exposure, the media was replaced with serum-free media containing latex particles labeled with a pH-dependent fluorescent dye and phagocytosis was allowed to proceed. The dye is minimally fluorescent at neutral pH, and intensely fluorescent at an acidic pH similar to the luminal pH of a lysosome. This allows distinction between phagocytic and non-phagocytic cells by fluorescence (FIGS. 1a,b). Eating and non-eating populations were sorted by fluorescence-activated cell sorting (FACS) (FIG. 1b), genomic DNA from each population was sequenced, and the sgRNA distributions were analyzed in eating and non-eating populations for both the young serum and no serum conditions. The effect size and p-value of each gene knockout were estimated using casTLE[27], wherein sgRNAs enriched in the eating population are represented by a positive effect sign and sgRNAs enriched in the non-eating population are represented by a negative effect sign. The significantly enriched sgRNAs ("hits") between young serum and no serum conditions were compared, and hits categorized based on their magnitude and direction (inhibiting phagocytosis or promoting phagocytosis) in each condition (FIGS. 1c,d).

In addition to discovering general regulators of phagocytosis which inhibit or promote phagocytosis in both conditions (FIGS. 1e,f), hits which displayed differential effects depending on the presence of young serum were discovered. For example, specific knockouts inhibited phagocytosis in the young serum condition but had no effect in the no serum condition (e.g. B4GALT1, FIG. 1g), indicating that these genes transduce a pro-phagocytic signaling cascade initiated by a factor in young serum. In contrast, another category of hits promoted phagocytosis in the no serum condition, but had no effect in the young serum condition (e.g., PTPN6, FIG. 1h). These data indicate that young serum downregulates genes that normally inhibit phagocytosis. Knocking out genes in this category recapitulates the pro-phagocytic effect of young serum, and mimics pathways by which young serum exerts this effect.

Figure 2:
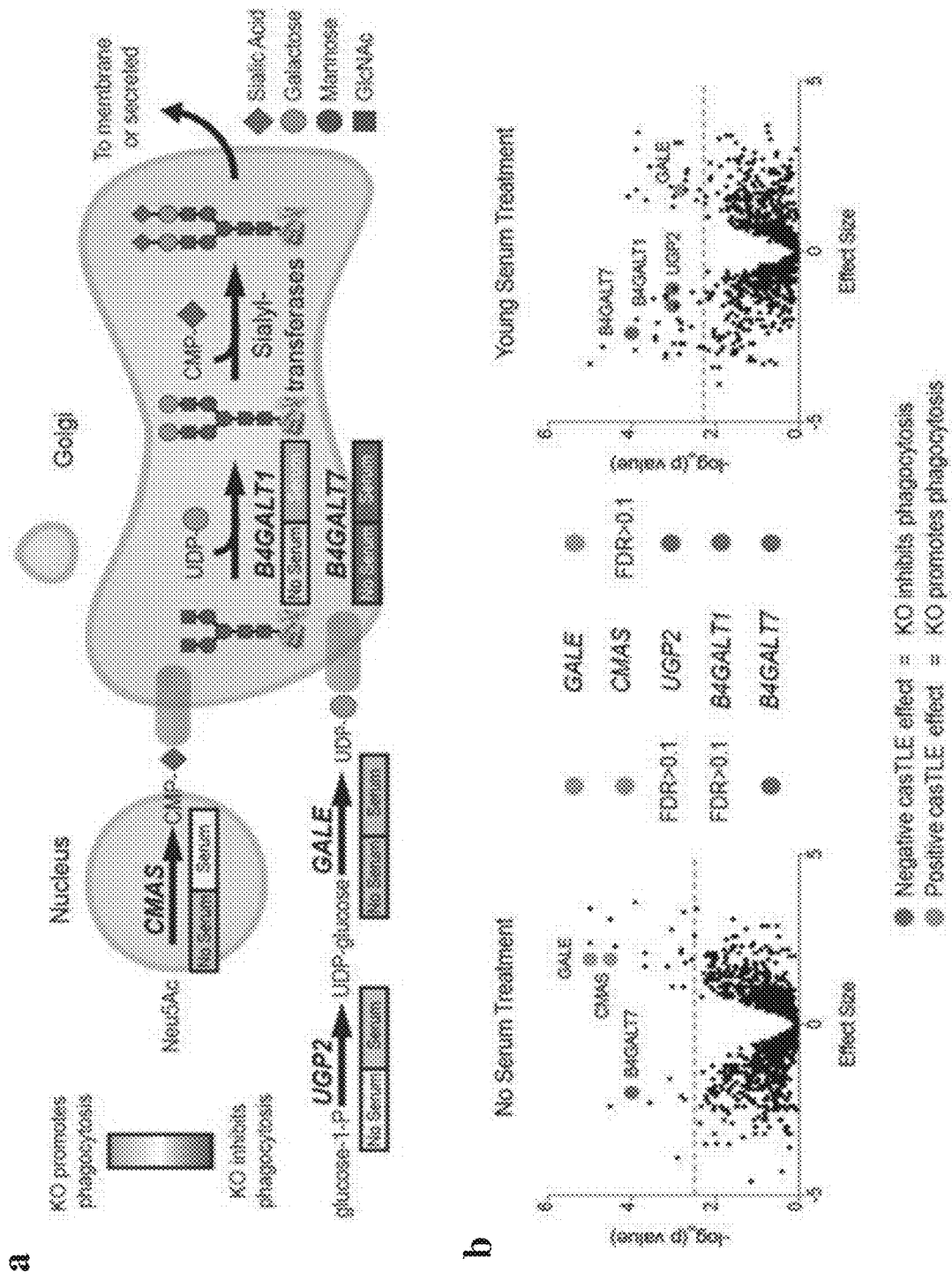
FIG. 2 shows that cell-surface sialic acid inhibits phagocytosis. (a), Pathway map of hits involved in galactosylation and subsequent terminal sialylation. Color gradient represents the following quantification: Sign of Effect Size (+/−)*−Log 10 (p-value). (b), Volcano plot of significant glycosylation hits from screen in the no serum-treated (left) and the young serum-treated (right) cells. Dashed line represents 10% false discovery rate (FDR) cutoff. Positive casTLE effect (yellow) represents genes targeted by sgRNAs enriched in the eating fraction. Negative casTLE effect (blue) represents genes targeted by sgRNAs enriched in the non-eating population. (c), Histograms of surface *Sambucus nigra* agglutinin (SNA) reactivity (left, α2-6-linked sialic acid) and *Maackia amurensis* agglutinin (MAA) reactivity (right, α2-3-linked sialic acid and sulfatyl-GalNAc) in wild-type (orange), wild-type cells treated with sialidase (blue), and CMAS knockout cells (red) assessed by flow cytometry. (d), Phagocytosis of pH-dependent fluorescent particles monitored over 24 hours. Control BV2 cells infected with a "safe-targeting" sgRNA or knockout BV2 cells infected with a sgRNA targeting CMAS were treated with no serum or young serum prior to feeding. (e), Representative images of control or CMAS knockout cells treated with no serum, fed pH-dependent fluorescent beads (red signal), and incubated with calcein AM fluorescent dye (green signal) to visualize live cells. (f), Phagocytosis of pH-dependent fluorescent particles by BV2 cells treated with no serum or young serum and with a vehicle control or a sialic acid metabolic inhibitor. (g), Phagocytosis of pH-dependent fluorescent particles by BV2 cells treated with no serum or young serum and with or without sialidase for 1 hour prior to feeding. (h), Phagocytosis of pH-dependent fluorescent particles by CMAS knockout cells decorated with no polymer (black line), α2-3-linked sialic acid (blue line), or α2-6-linked sialic acid (orange line). Each phagocytosis experiment was performed three independent times in technical triplicate. Data represent mean+/−S.E.M. Scale bar, 100 um.
Figure 2:
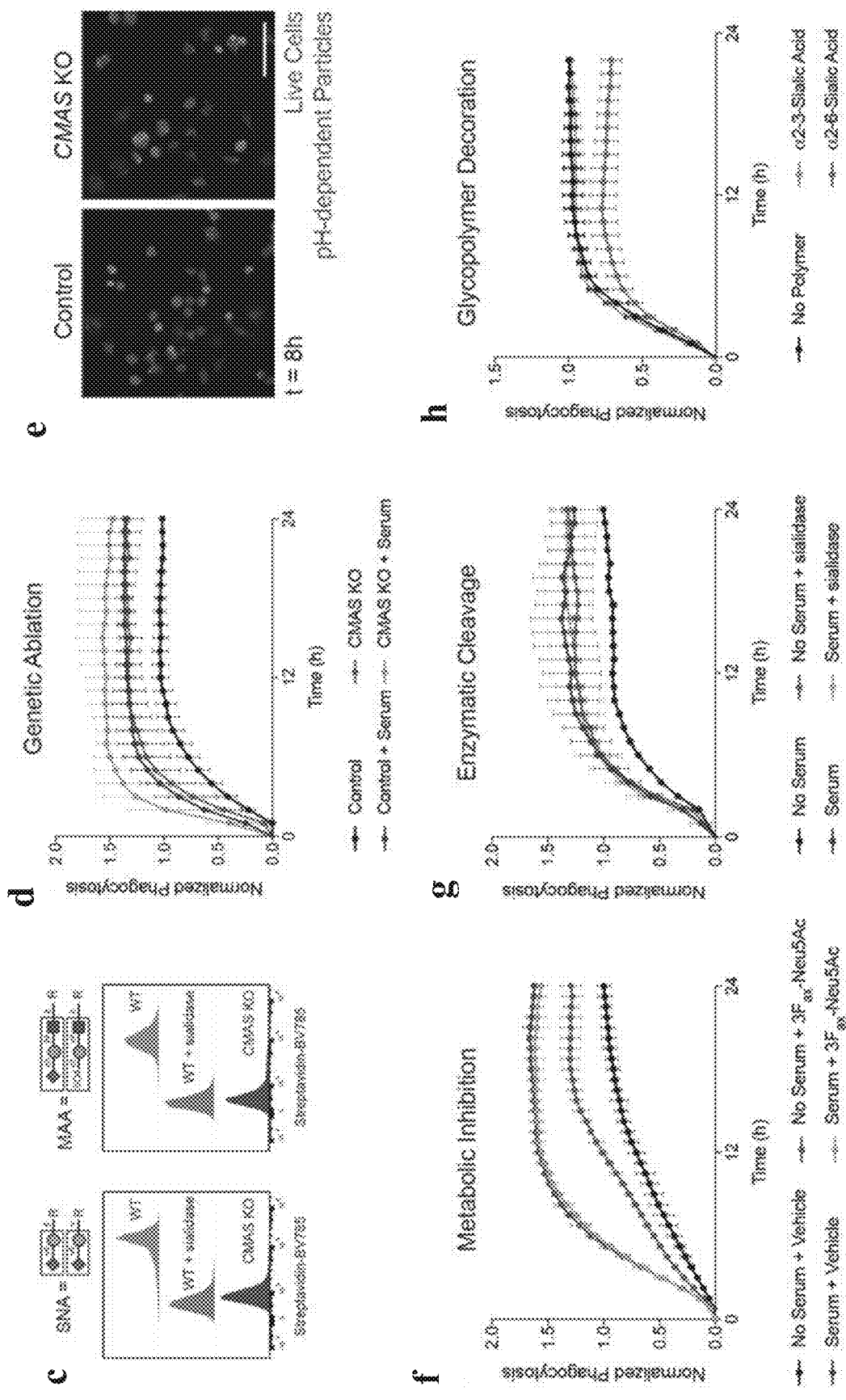

Multiple glycosylation enzymes were among the top hits that regulated phagocytosis in a young serum-specific manner (FIGS. 2a,b). In particular, knocking out CMAS, that codes for the bottleneck enzyme in sialic acid synthesis[28], strongly promoted phagocytosis in the no serum condition but had no significant effect in the young serum condition. This effect pattern aligns with the aforementioned category of hits that recapitulate the pro-phagocytic effect of young serum.

Sialic acid is a glycan modification that negatively regulates the immune system in multiple contexts through both steric hindrance, and as a ligand for a conserved family of sialic acid-binding immunoglobulin-like lectins termed Siglecs[29]. During phagocytosis, sialic acid participates in the acquisition of phagocytic potential during the differentiation of monocytes to mature macrophages[30]. In the central nervous system (CNS), sialic acid ligand expression on neurons protects them from microglia-mediated phagocytosis via Siglec-dependent signaling[31]. BV2 cells, the cell line used in the present CRISPR102 Cas9 screen, de-sialylate neurons in vitro thereby enabling opsonization and engulfment[32]. The present screen interrogated genes in the phagocyte rather than in the phagocytic target, showing that sialic acid expression on microglia inhibits phagocytosis.

Figure 6:
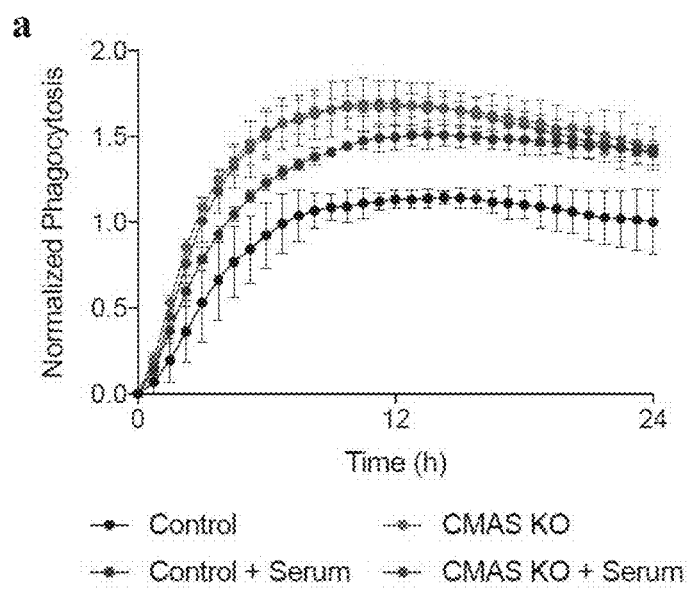
FIG. 6 shows that inhibition of sialic acid promotes phagocytosis of myelin. (a), Phagocytosis of myelin conjugated to a pH-dependent fluorescent dye monitored over 24 hours. Control BV2 cells or knockout BV2 cells infected with an sgRNA targeting CMAS were treated with no serum or young serum prior to feeding. Data represent mean+/− 95% C.I.

To validate the results of the screen, CMAS in BV2 cells was knocked out, and the absence of cell-surface sialic acid by lectin staining was confirmed (FIG. 2c). Compared to a control cell line infected with an sgRNA targeting an unannotated region of the genome ("safe-targeting")[25], CMAS knockout BV2 cells displayed improved phagocytosis of latex particles (FIG. 2d,e) and myelin (FIG. 6) in the absence of serum, but no phagocytic advantage in the presence of young serum concordant with the screen result. Similarly, treatment of wild-type BV2 cells with a global metabolic inhibitor of sialic acid synthesis, 3Fax-Neu5Ac[33], promoted phagocytosis in the no serum condition only (FIG. 2f). Because sialylated proteins are found in a variety of cellular compartments, wild-type BV2 cells were treated with sialidase from *Vibrio cholerae* to specifically remove sialic acid from the cell-surface (FIG. 2e). Enzymatic cleavage of cell-surface sialic acid was able to fully recapitulate the pro-phagocytic effect of CMAS knockout and promote phagocytosis in the absence of young serum (FIG. 2g).

Sialic acids are present in both N-linked and κ-linked glycans on the cell surface, and are attached to underlying glycan chains in a diversity of configurations. Two common linkages include a bond between the C-2 anomeric carbon on sialic acid to the C-3 or C-6 positions of galactose, termed α2-3- and α2-6-linked sialic acid respectively[34]. These linkages confer sialic acid with different binding specificities and biological functions. CMAS knockout cells devoid of endogenous cell surface sialic acid were decorated with synthetic glycopolymers bearing α2-3- or α2-6-linked sialic acid, and a phospholipid tail for membrane insertion[35]. Addition of α2-6-linked sialic acid, but not α2-3-linked sialic acid, to the naked surface of CMAS knockout cells inhibited phagocytosis (FIG. 2h). These results indicate that cell-surface sialic acid impairs phagocytosis in the absence of young serum, and that α2-6-linked sialic acid is at least partially responsible for this impairment.

Figure 3:
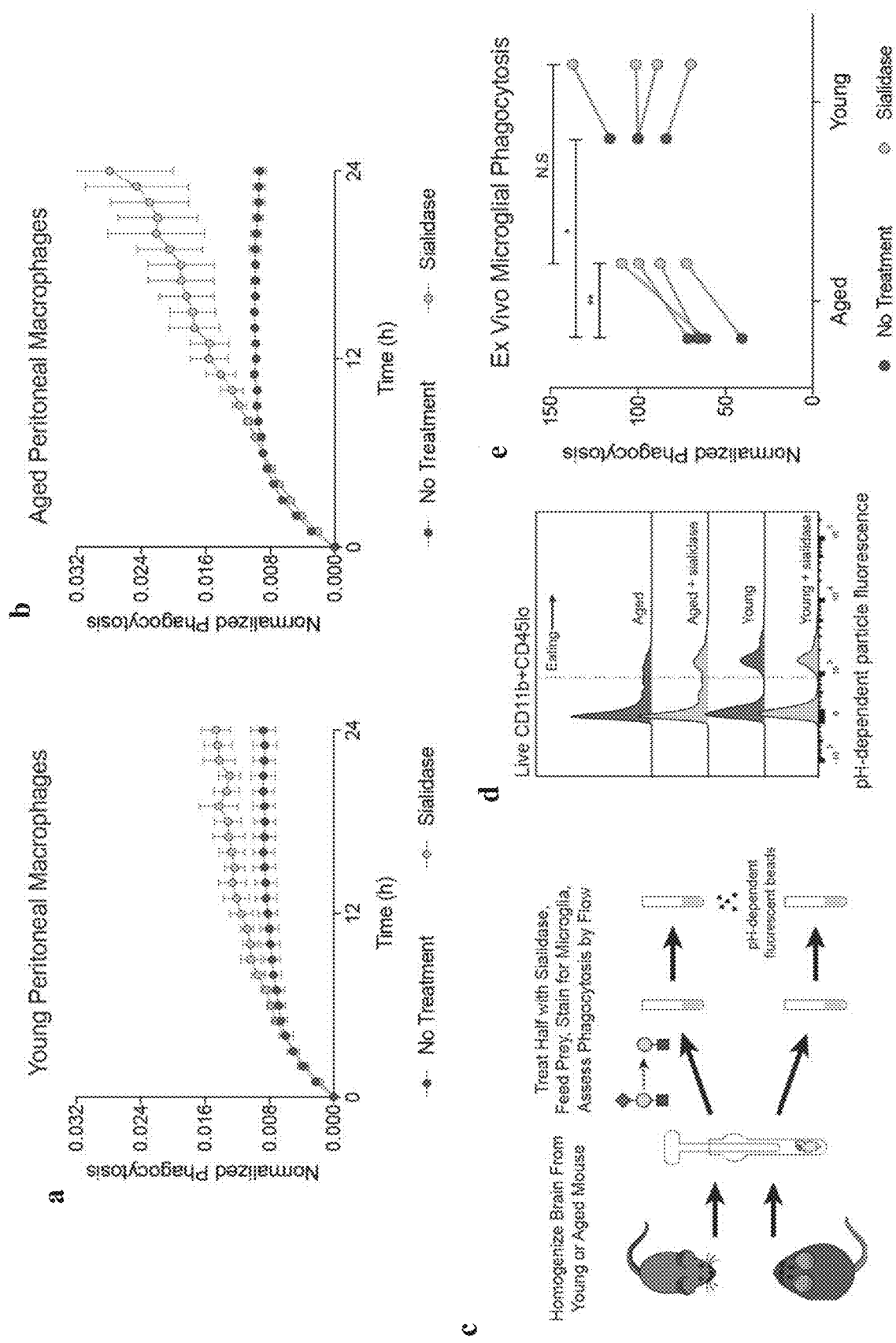
FIG. 3 shows that removal of cell-surface sialic acid restores aged macrophage and microglia phagocytosis. (a,b), Peritoneal macrophages isolated from 2-month-old (a) or 20-month-old (b) mice were treated with or without sialidase and fed pH-dependent fluorescent particles. Phagocytosis was monitored by microscopy for 24 hours. N=3 per group. (c), Experimental schematic of ex vivo microglial phagocytosis assay. (d), Representative histogram showing pH-dependent bead fluorescence in untreated (purple) and sialidase (yellow) treated young (2-month-old) and aged (18-month-old) microglia. (e), Quantification of phagocytosis by aged or young microglia treated with (yellow) or without (purple) sialidase. N=4 animals per group. Lines represent paired samples harvested from the same mouse, split into two separate tubes, and treated in parallel accordingly. *P<0.05, **P<0.005, N.S.=no significance; Two-way ANOVA with matching and Sidak's multiple comparisons test. Data represent mean+/−S.E.M.

Peritoneal macrophages maintain age-related phagocytic deficits in vitro[5]. To test whether screen hits that recapitulate the pro-phagocytic effect of young serum, such as inhibition of cell-surface sialic acid, rescue phagocytosis in primary aged macrophages but do not enhance phagocytosis in already competent young macrophages, peritoneal macrophages from young and aged mice were treated with sialidase, and then fed pH-dependent fluorescent latex particles. Cleavage of cell-surface sialic acid increased phagocytosis dramatically in aged macrophages (FIG. 3b) compared to young macrophages (FIG. 3a). To determine whether age-dependent phagocytic impairment by sialic acid occurs in CNS microglia in view of constraints of studying phagocytosis by primary microglia in vitro[36,37] an ex vivo assay was developed to measure phagocytosis of acutely isolated microglia without long-term culturing (FIG. 3c). Microglia retained their phagocytic potential and displayed an age-dependent defect in phagocytosis ex vivo (FIGS. 3d,e). Removal of cell-surface sialic acid rescued phagocytosis in aged microglia, but did not enhance phagocytosis in already competent young microglia (FIGS. 3d,e).

Figure 4:
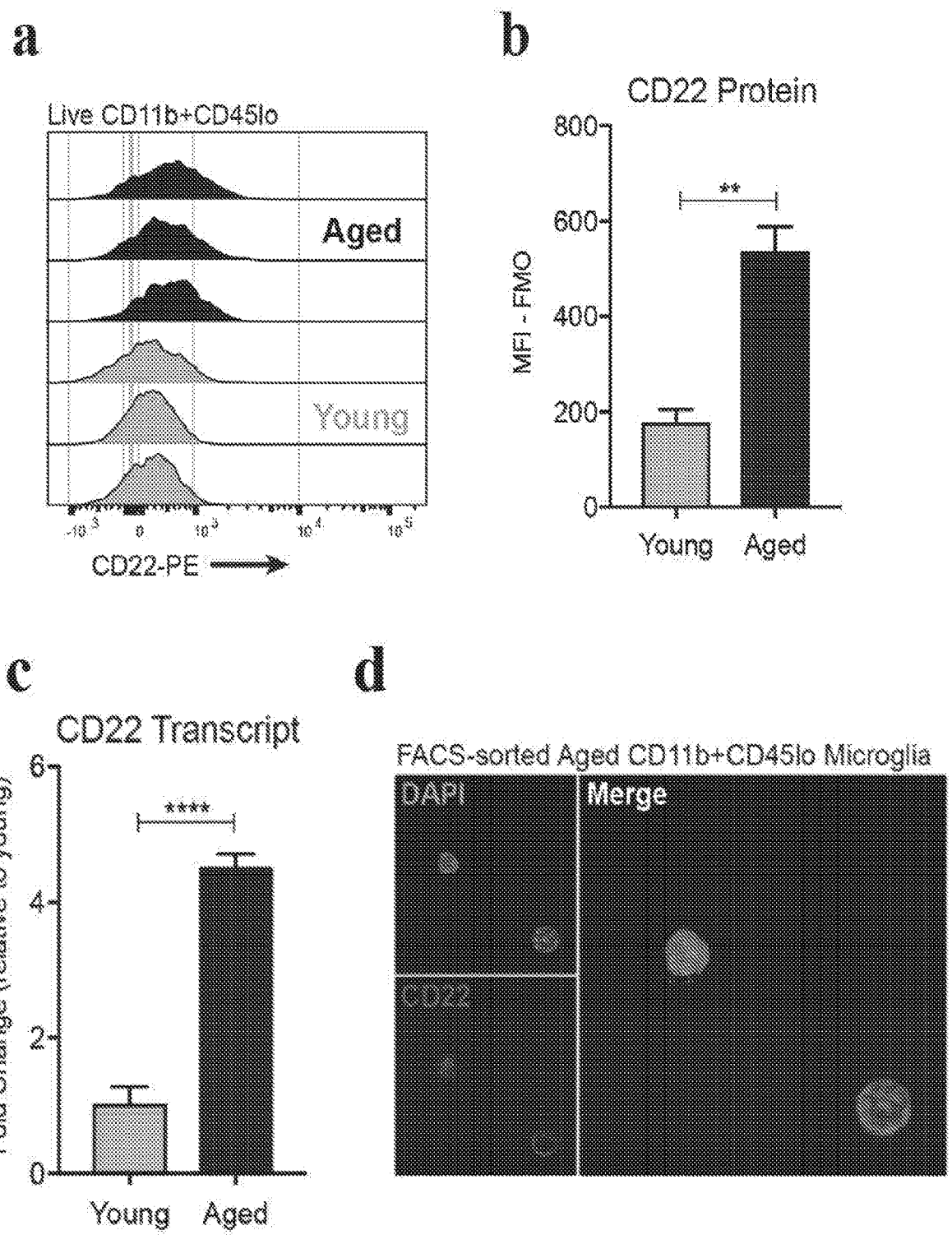
FIG. 4 shows that CD22 is upregulated on aged microglia and inhibits phagocytosis. (a), Representative histogram showing expression of CD22 on microglia from three young (2-month-old), gray or aged (18-month-old, black) mice assessed by flow cytometry. (b), Quantification of mean fluorescence intensity (MFI)-fluorescence minus one (FMO) background intensity of young (gray) and aged (black) microglia assessed by flow cytometry. N=4 animals per group. (c), CD22 transcript levels normalized to a housekeeping gene transcript (β-actin): data represent fold change relative to young microglia. N=4 animals per group. (d), Representative image of FACS-sorted microglia from an aged mouse stained for DAPI (blue) and CD22 (red). (e), Phagocytosis of pH-dependent fluorescent particles by aged microglia treated with sialidase (yellow), a CD22 blocking antibody (red), or no treatment (purple) for one hour prior to feeding. N=4 animals per group. Lines represent paired samples harvested from the same mouse, split into three separate tubes, and treated in parallel accordingly. f, Phagocytosis of pH-dependent fluorescent particles by microglia from WT or CD22−/− animals were treated with (yellow) or without (purple) sialidase. N=6 animals per group. Lines represent paired samples harvested from the same mouse, split into two separate tubes, and treated in parallel accordingly. (g), Representative images of hippocampi from 12-month-old CD22−/− mice or age-matched wild-type mice stained for Iba1 (green, microglial marker) and CD68 (red, lysosomal marker). Percentage of Iba1+ microglia containing high levels of CD68 in CD22−/− and wild-type mice. N=7 animals per group. *P<0.05, P<0.005, **P<0.00005, N.S.=no significance; Student's t-test, one-way, or two-way ANOVA with matching as appropriate. Data represent mean+/−S.E.M. Scale bar, 100 um.
Figure 4:
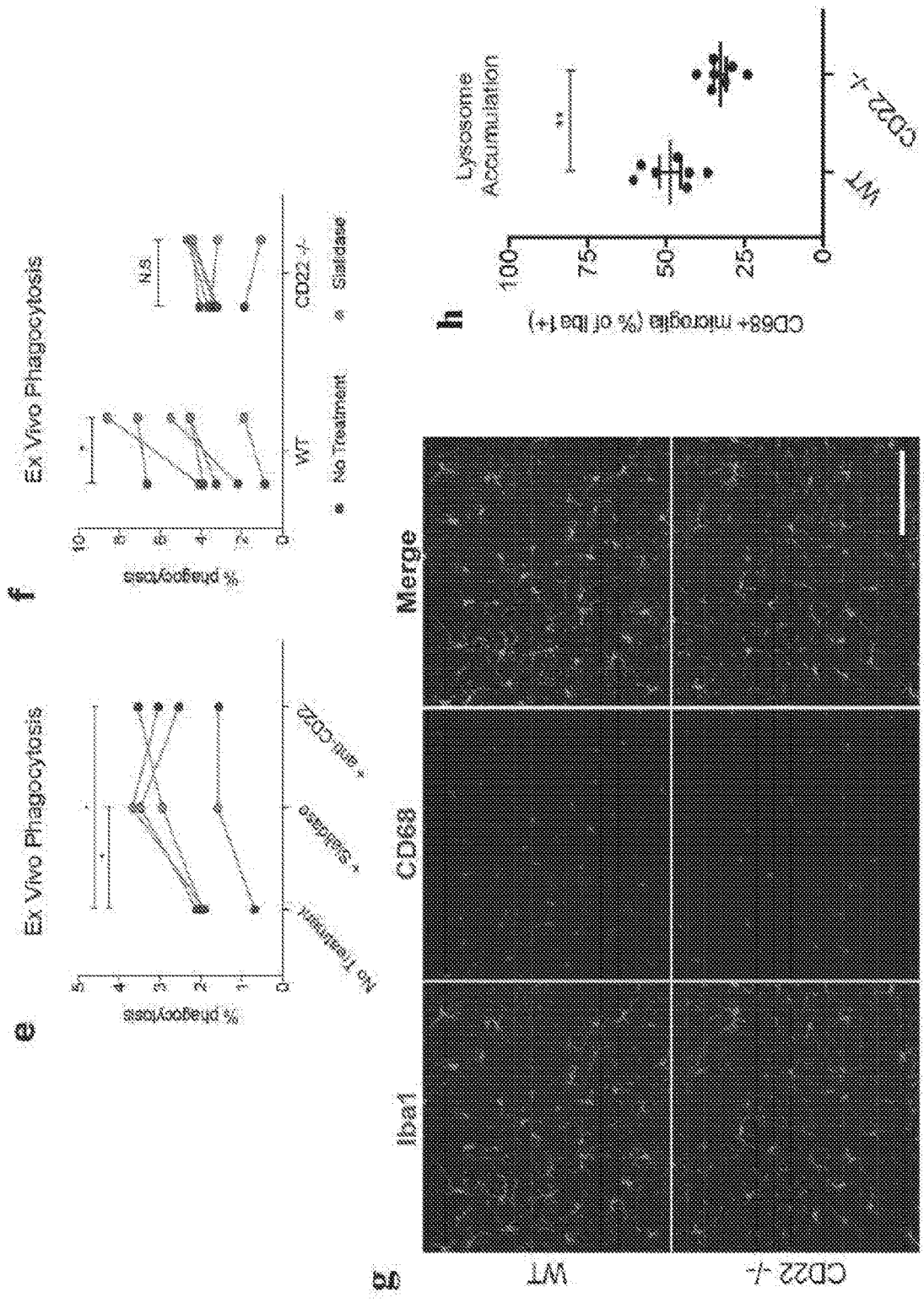
Figure 5:
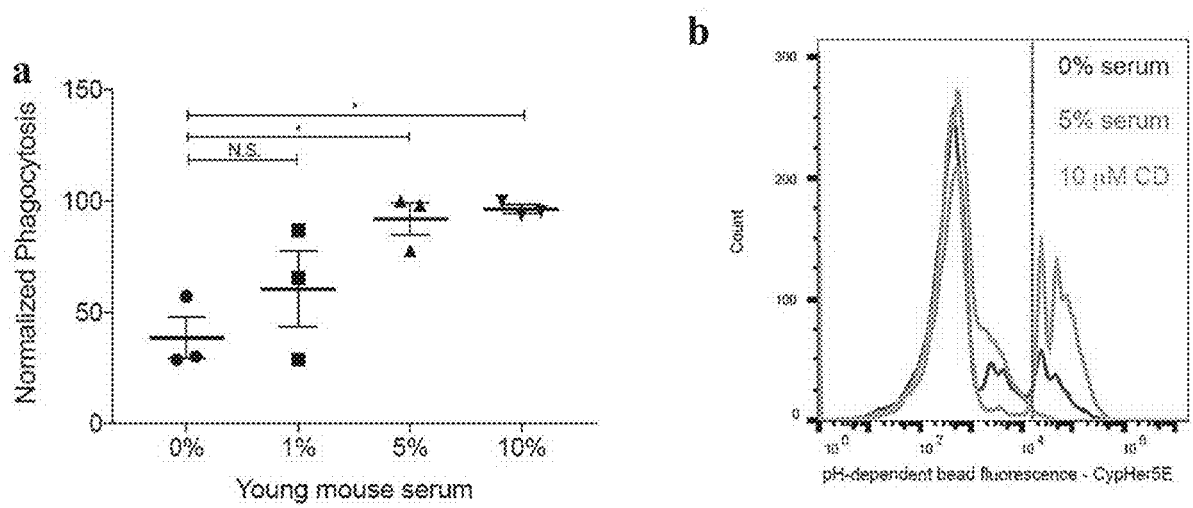
FIG. 5 shows that young mouse serum promotes phagocytosis in BV2 cells. (a), Phagocytosis of pH-dependent fluorescent particles by BV2 cells treated with increasing doses of young mouse serum. (b), Representative histogram showing pH-dependent bead fluorescence of BV2s assessed by flow cytometry following serum-free (red) or 5% young mouse serum treatment (blue) and 1 hour of feeding. Eating gate (dashed line) is defined based on cytochalasin D (CD) treated cells (orange) in which actin polymerization is blocked preventing engulfment. Normalized Phagocytosis=% of maximum phagocytosis within independent experiments. *P<0.05, N.S.=no significance; one-way ANOVA with Dunnett's multiple comparisons test. Phagocytosis experiment was performed three independent times in technical triplicate. Data represent mean+/−S.E.M.
Figure 7:
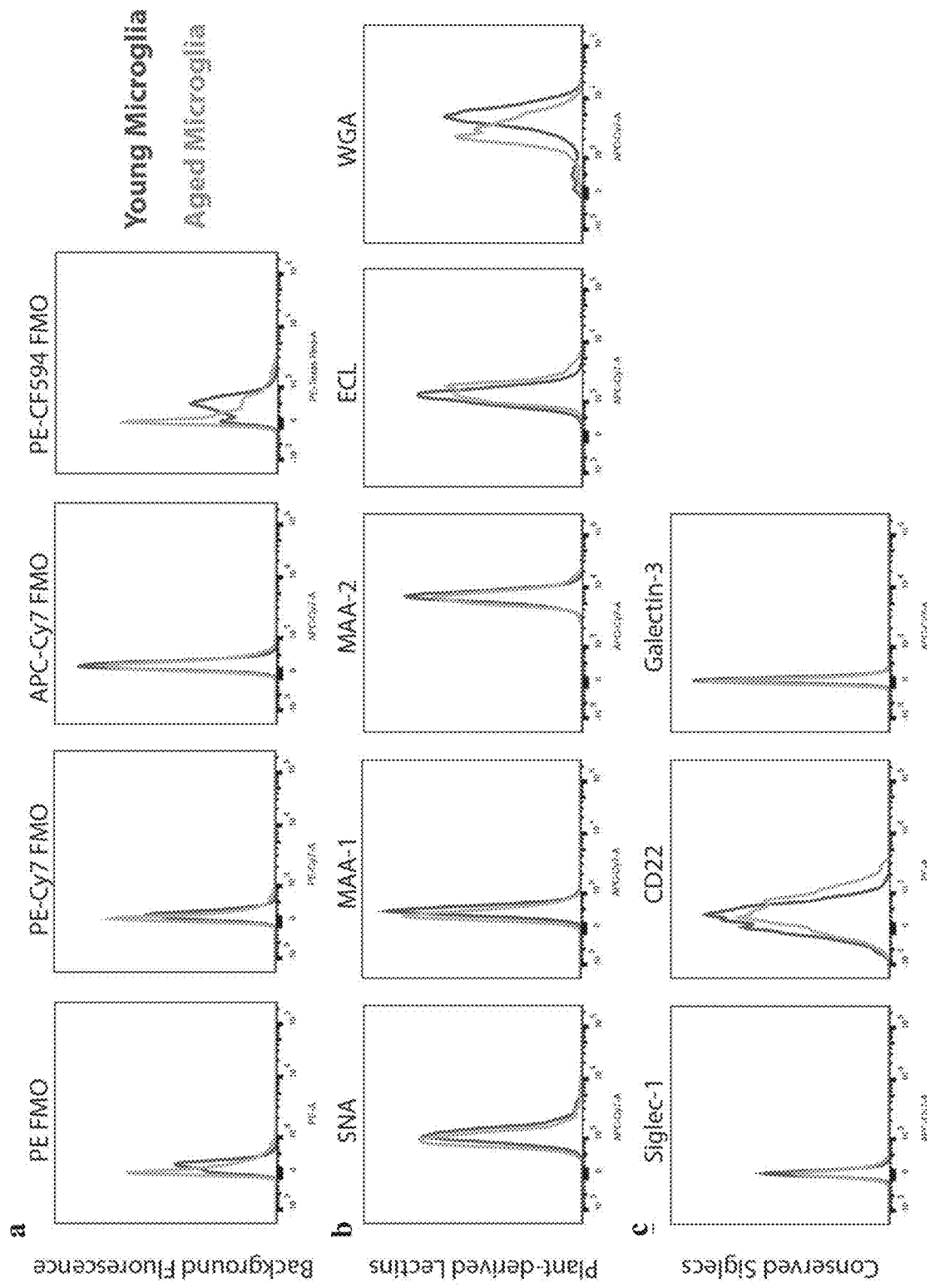
FIG. 7 shows differences of sialic acid-related molecule expression between young and aged microglia. (a), Fluorescence minus one (FMO) background fluorescence of young (red) and aged (blue) microglia in the channels used for subsequent surface phenotyping. (b,c,d,e), Flow cytometry analysis of young (red) and aged (blue) microglia for expression of plant-derived lectin ligands (b), conserved Siglecs (c), mouse-specific CD33-related Siglecs (d), and recombinant Siglec ligands (e). (f), Gating strategy to immunophenotype microglia to minimize signal contribution of autofluorescent cells.
Figure 7:
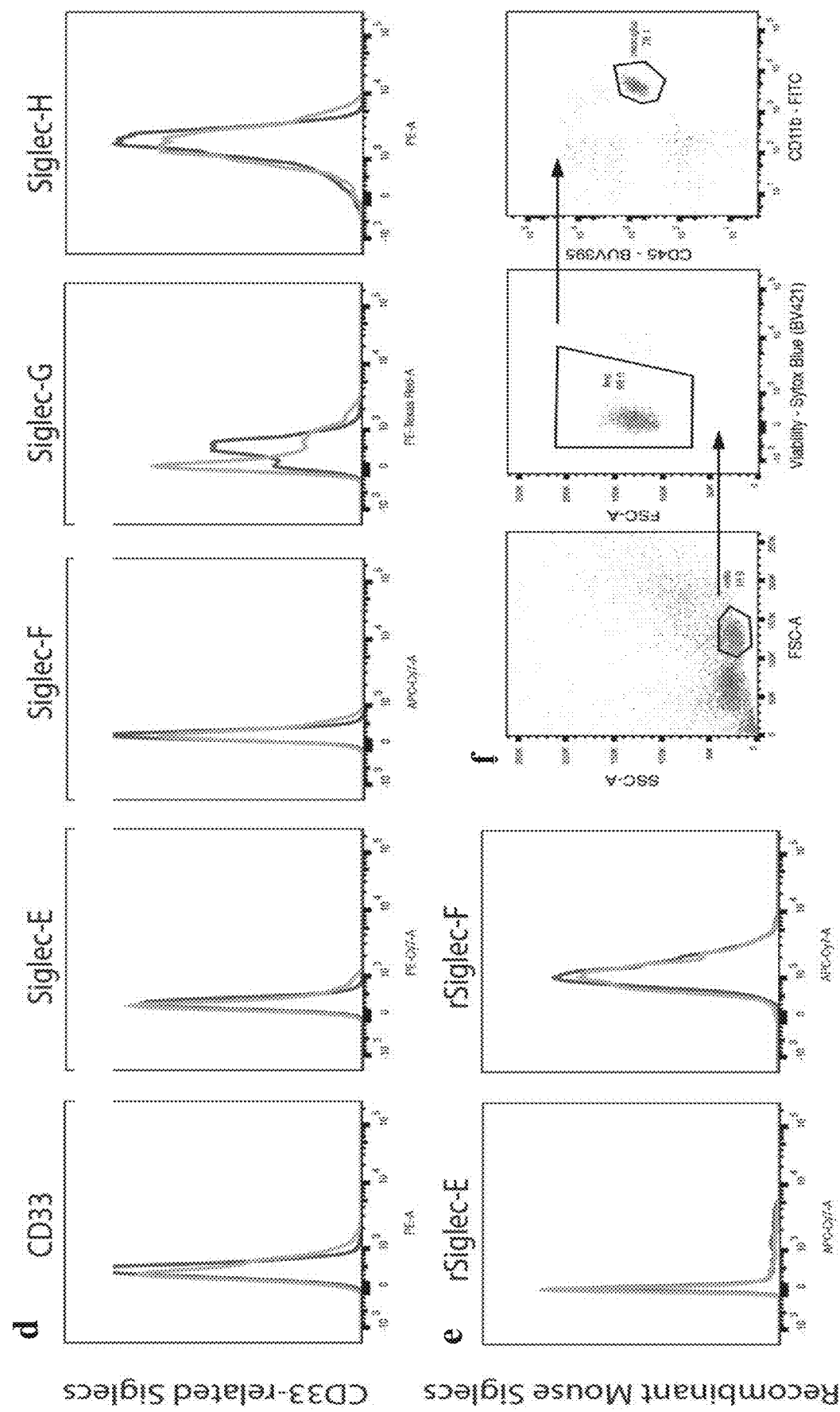
Figure 8:
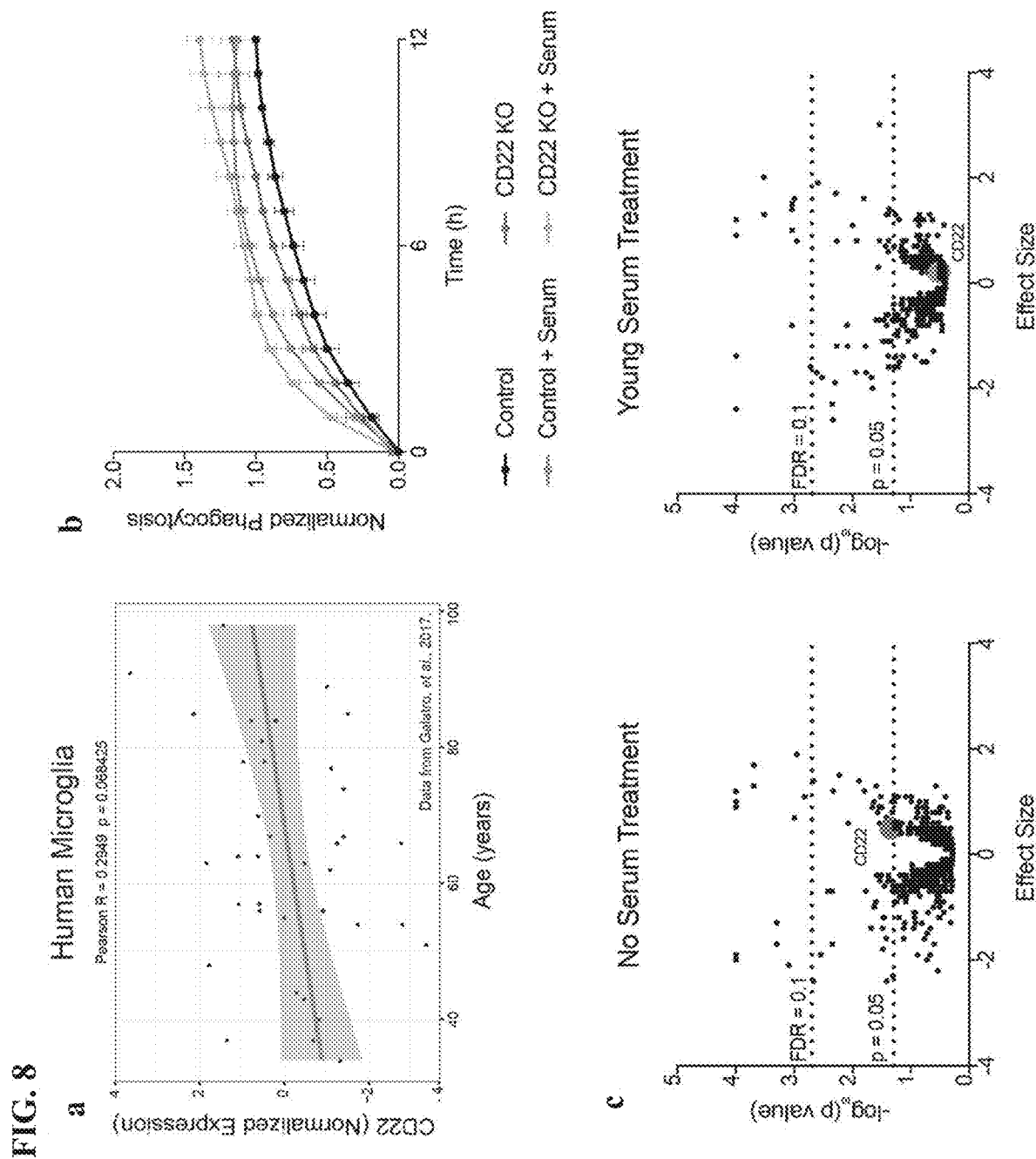
FIG. 8 shows that human CD22 is upregulated in microglia with age, and that knocking out CD22 promotes phagocytosis in BV2 cell line. (a), Analysis of previously published human microglia transcriptome dataset reveals positive correlation of CD22 with age. (b), Phagocytosis of pH-dependent fluorescent particles monitored over 12 hours by control or CD22 knockout BV2 cells treated with no serum or young serum prior to feeding. Data represent mean+/−S.E.M. (c), Volcano plot of hits from membrane proteins screen in the no serum-treated (left) and the young serum-treated (right) BV2s. Knocking out CD22 has no effect in the presence of young serum, but promotes phagocytosis in the absence of young serum. FDR, false discovery rate; p-value calculated using a Student's t-test.
Figure 9:
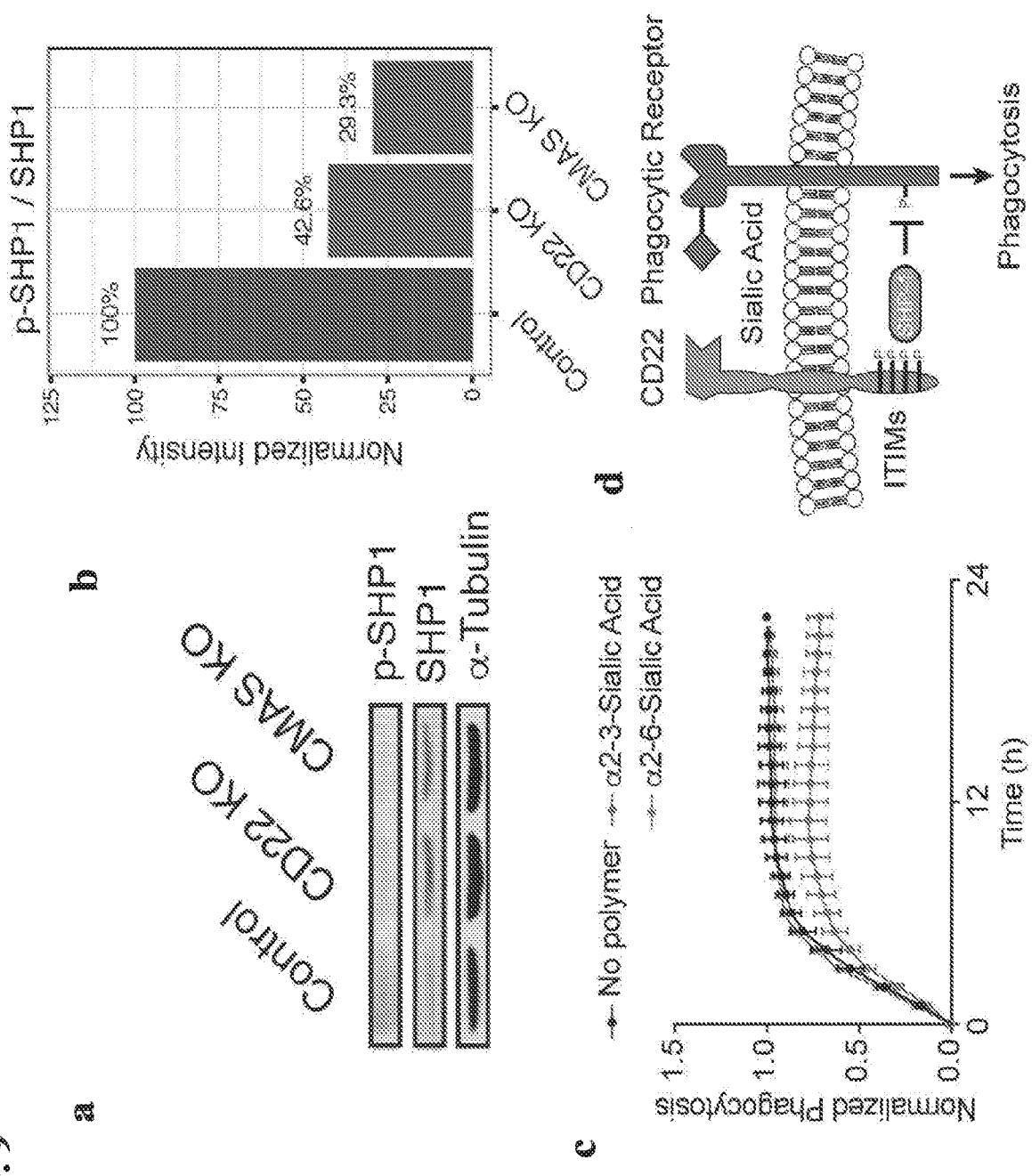
FIG. 9 shows that CD22 mediates inhibitory signaling downstream of sialic acid. (a), Western blot for phospho-SHP-1 (active), SHP-1 (total), and α-tubulin (loading control) of BV2 lysates. (b), Ratio of active (inhibitory) to total SHP1 is reduced in CD22 and CMAS knockout cells. (c), Phagocytosis of latex particles by CMAS-knockout BV2s decorated with glycopolymers bearing various sialic acid linkages monitored over 24 hours using a time-lapse fluorescence microscope. (d), Schematic diagram of model CD22/sialic acid-mediated inhibition of phagocytosis.
Figure 10:
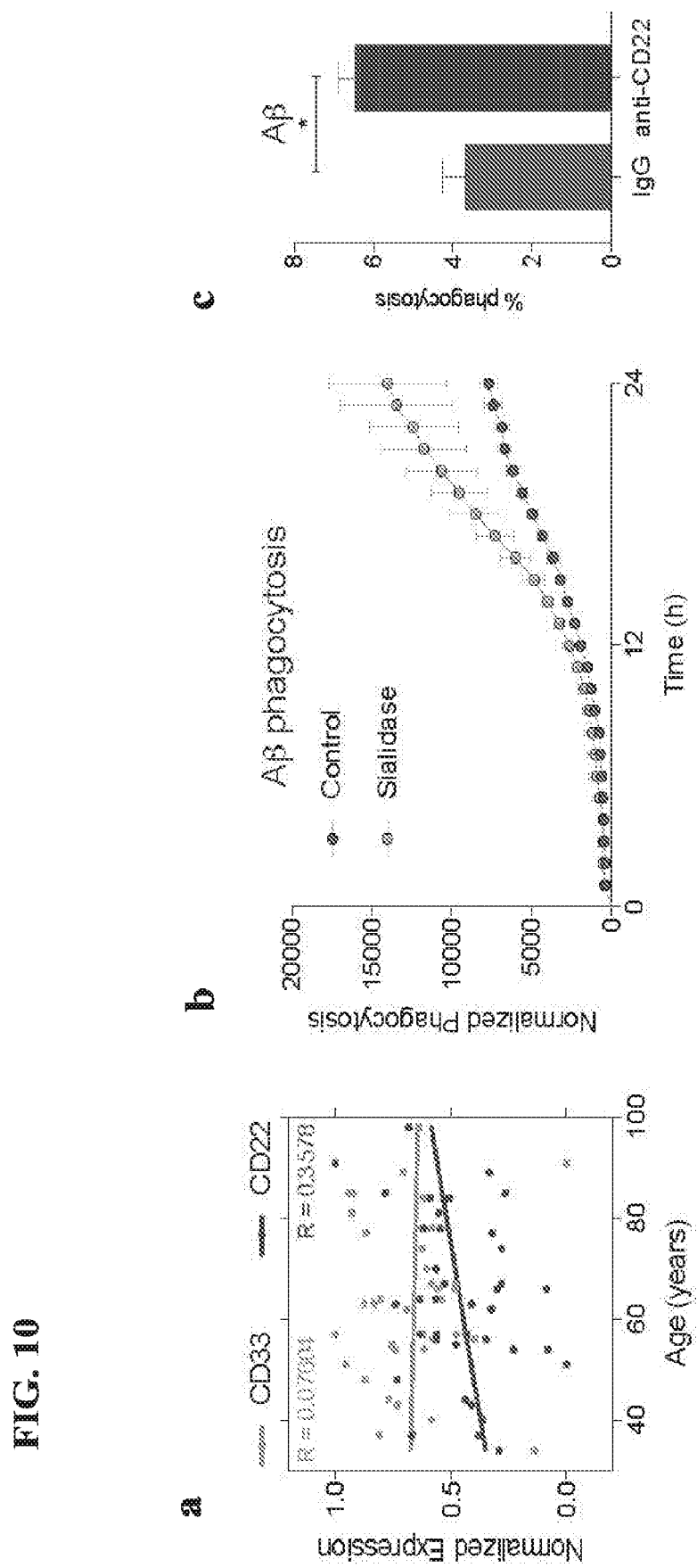
FIG. 10 shows that human microglia upregulate CD22 with age and genetic ablation of CD22 restores homeostatic phagocytosis. (a), Analysis of a published human microglia transcriptome dataset reveals no correlation of CD33 with age, but positive correlation of CD22 with age. While gain-of-function mutations in CD33 are associated with increased risk of developing Alzheimer's disease and inhibit microglial uptake of Aβ, loss-of-function CD33 mutations are protective, conveying that blocking inhibitory Siglec signaling ameliorates Alzheimer's disease by improving microglial phagocytosis. CD33 expression does not correlate with age in mice or humans, but CD22 is upregulated on aged mouse microglia and is transcriptionally correlated with age in human microglia. (b), Phagocytosis of Aβ oligomers by BV2 treated with vehicle or sialidase. (c), Ex vivo phagocytosis of Aβ oligomers by primary aged microglia treated with a control antibody or anti-CD22.
Figure 11:
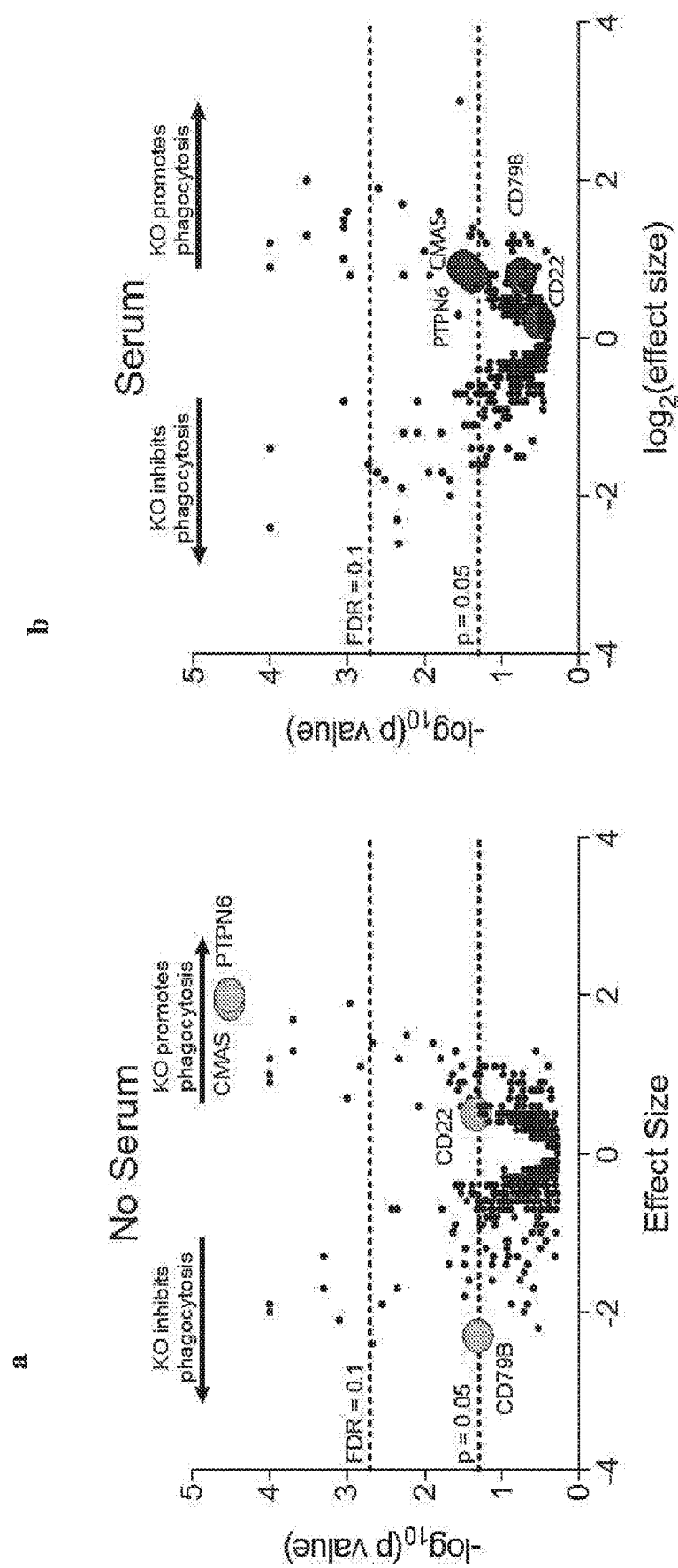
FIG. 11 shows that cell-surface sialic acid inhibits phagocytosis. Volcano plots show significant glycosylation hits from screening of the no serum-treated (a) and the young serum-treated (b) cells. The dashed line represents the 10% false discovery rate (FDR) cutoff. The positive casTLE effect (green) represents genes targeted by sgRNAs enriched in the eating fraction. The negative casTLE effect (red) represents genes targeted by sgRNAs enriched in the non-eating population.
Figure 12:
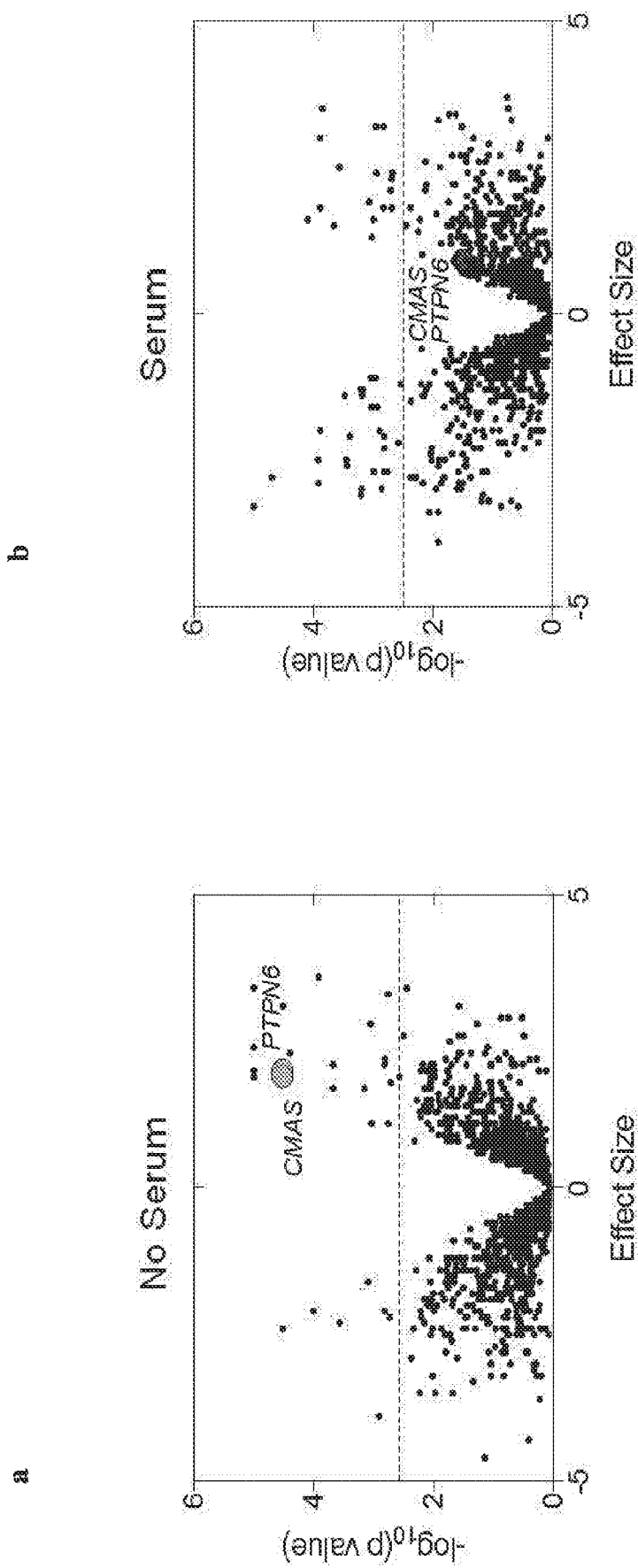
FIG. 12 shows that cell-surface sialic acid inhibits phagocytosis in a first screen composed of an sgRNA sublibrary that knocks out drug targets, kinases and phosphatases. Volcano plots show significant glycosylation hits from screening of the no serum-treated (a) and the young serum-treated (b) BV2 cells. The dashed lines represent the 10% false discovery rate (FDR) cutoff. Green indicates a significant hit, and red indicates "does not pass significance" by the Benjamin-Hochberg cutoff. Knocking out sialic acid synthesis and signaling replicates the pro-phagocytic effect of serum. (Storey J D and Tibshirani R. Statistical significance for genomewide studies. *Proc Natl Acad Sci USA* 2003 Aug. 5; 100(16):9440-5.)
Figure 14:
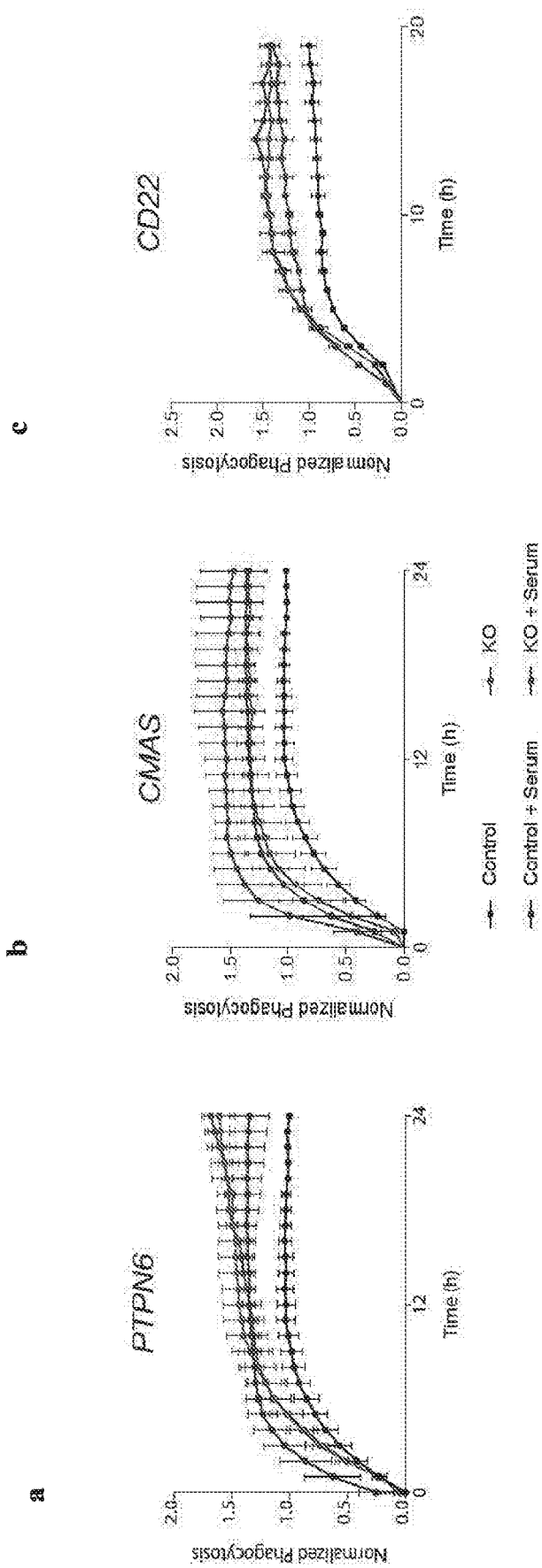
FIG. 14 shows that genetic ablation of components of the CD22-sialic acid signaling axis replicates the pro-phagocytic effects of young serum, and that the components are targets for restoration of phagocytosis in aged microglia. Phagocytosis of pH-dependent fluorescent particles was monitored over 24 hours. Control BV2 cells infected with a "safe-targeting" sgRNA, or knockout BV2 cells infected with a sgRNA targeting CMAS, were treated with no serum or young serum prior to feeding.
Figure 15:
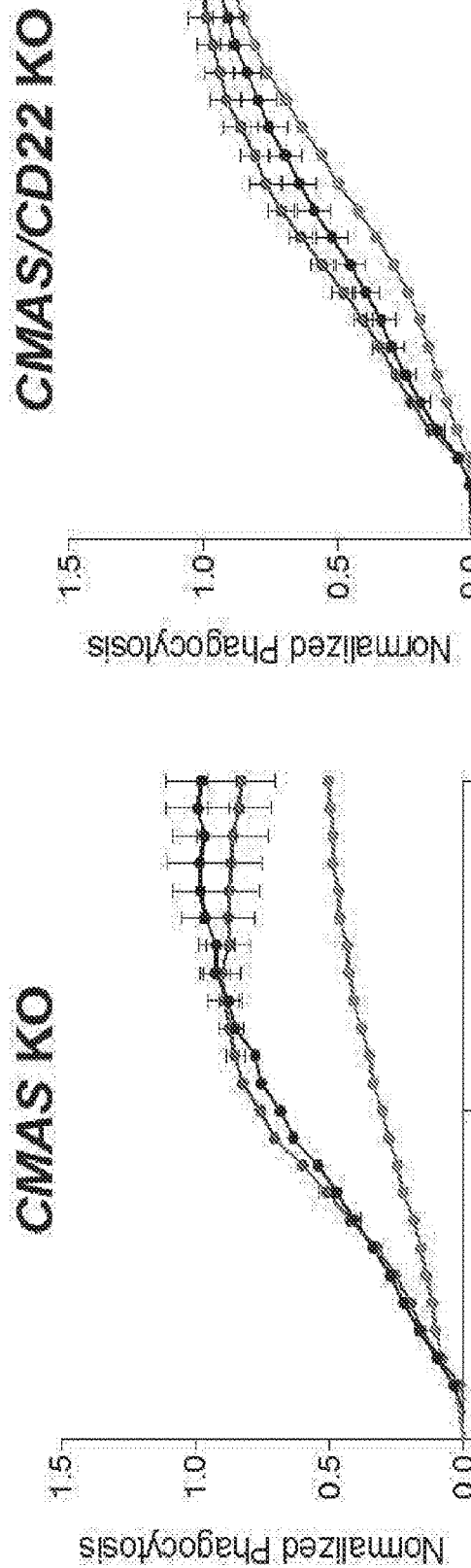
FIG. 15 shows the effects of α2-3-sialic acid and α2-6-sialic acid on normalized phagocytosis in CMAS single knock-out and CMAS/CD22 knockout BV2 cells. Absence of CD22 abrogates the anti-phagocytic effects of the glycopolymer. These results show that α2-6-sialic-acid inhibits phagocytosis in a CD22-dependent manner. Coating the surface of CMAS KO BV2 cells that are devoid of endogenous sialic acid with synthetic α2-6-linked sialic acid, the ligand for CD22, inhibits phagocytosis (a). No phagocytic inhibition was observed when α2-6-linked sialic acid was added to CMAS/CD22 double KO cells (b). These data indicate that CD22 on aged microglia binds α2-6-linked sialic acid in cis, and thereby recruit active SHP-1, and subsequently self-inhibit phagocytosis.
Figure 16:
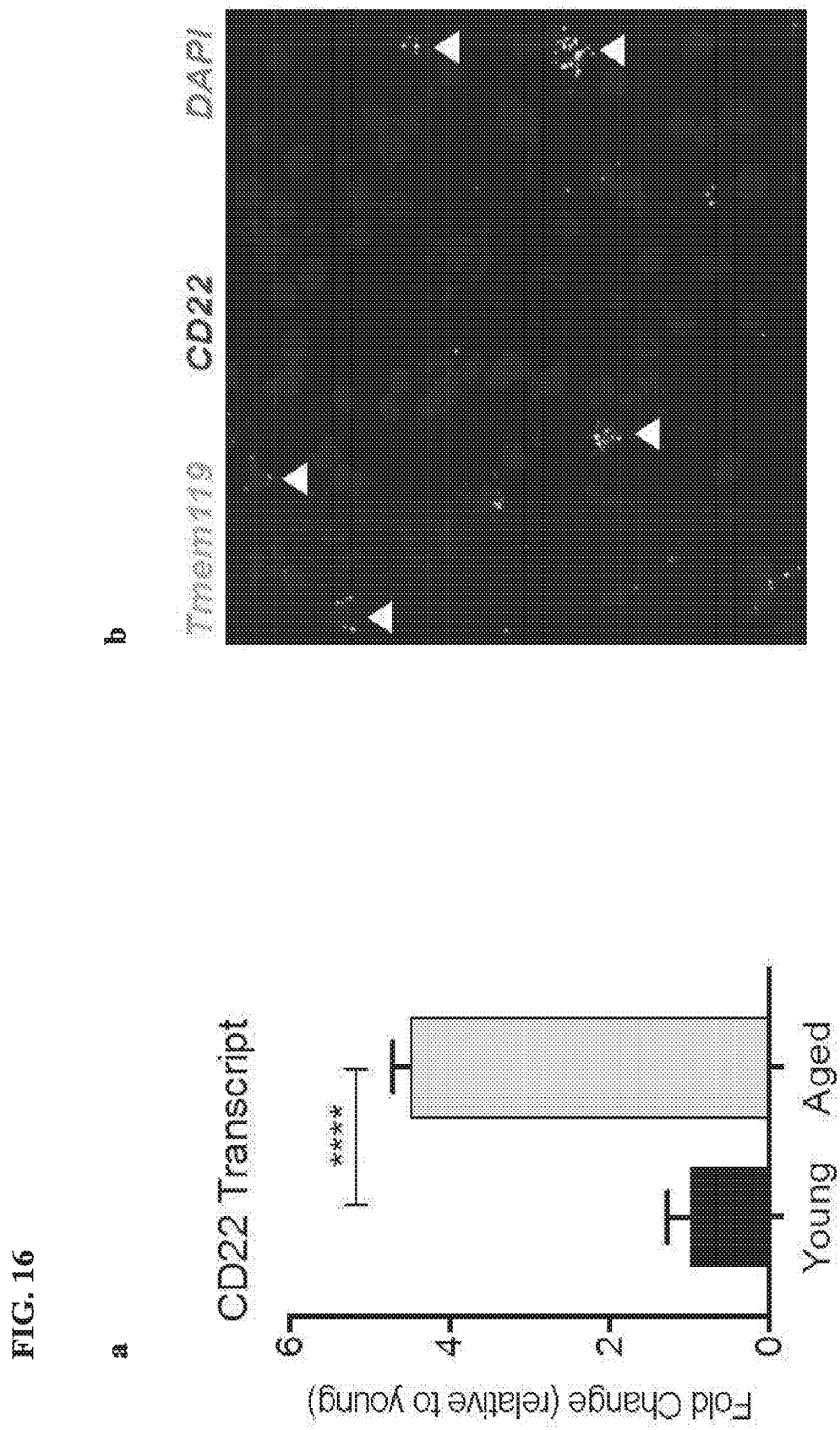
FIG. 16 shows that CD22 is transcriptionally upregulated on aged microglia. Oligonucleotides specific for a transcript of the microglia-specific gene Tmem119 and a transcript of CD22 were hybridized to aged brain tissue, and fluorescent probes were used after amplification of the signal to observe single molecule resolution with a confocal microscope using RNAScope RNA in situ hybridization technology. DAPI provides a generic nuclear stain. White triangles indicate cells that express both Trem119 and CD22 transcripts, and are indicative of CD22+ microglia. These results show that CD22 transcripts overlap with Tmem119 transcripts in the aged brain, whereas there is no overlap of the CD22 transcript in the young brain.

The selective sensitivity of aged microglia to sialidase-induced phagocytosis indicates that young and aged microglia comprise intrinsic differences in sialic acid-related biology at the cell-surface. To test whether sialic acid ligands, or their corresponding inhibitory receptors, are overexpressed on aged microglia expression of a large panel of sialic acid ligands and receptors were compared in young and aged microglia by flow cytometry. The panel included plant-derived lectins and recombinant mouse Siglecs to probe for ligand differences, and antibodies to almost every known mouse Siglec[38] to probe for receptor differences. Very few differences in sialic acid-related molecules between young and aged microglia were observed (FIG. 7). Surprisingly, CD22, a Siglec canonically restricted to expression on B-cells, was upregulated on aged microglia compared to young microglia (FIG. 4a). Overexpression was confirmed at both the protein (FIGS. 4b,d) and transcript level (FIG. 4c). These results align with a transcriptome dataset comparing young and aged mouse microglia[39]. Analysis of a published human microglia transcriptome dataset[40] indicates that CD22 expression is positively correlated with age in humans (FIG. 8a).

Known for its role in negative regulation of B-cell receptor signaling[41], CD22 is a highly conserved Siglec with a strong preference for α2-6-linked sialic acid ligands comprising multiple cytoplasmic immunoreceptor tyrosine-based inhibitory motifs (ITIMs)[42]. Upon BCR activation, Lyn and Syk kinases phosphorylate these ITIM domains, recruiting SHP-1 phosphatase to dephosphorylate active BCR signaling molecules[41]. The role of CD22 on phagocytic cells is hitherto unrecognized[43]. Knocking out PTPN6, which codes for SHP-1, the downstream signaling partner of CD22, promotes phagocytosis in the absence of young serum (FIG. 1h), and α2-6-linked sialic acid, the preferred ligand for CD22, inhibits phagocytosis (FIG. 2h), thereby denoting that CD22 transduces the anti-phagocytic effect of cell-surface sialic acid. Concordant with the results of the CRISPR-Cas9 screen, knocking out CD22 in BV2 cells moderately promoted phagocytosis (FIGS. 8b,c). To test whether CD22 regulates phagocytosis on aged primary microglia, an antibody targeting the sialic-acid binding domain of CD22 was used. Blocking CD22 on aged microglia promotes phagocytosis of latex particles ex vivo comparable to sialidase rescue (FIG. 4e). Microglia from middle-aged, 12-month-old CD22−/− mice display a reduced pro-phagocytic response to sialidase relative to age-matched wild-type control microglia (FIG. 4f). These data indicate that CD22 negatively regulates phagocytosis on aged microglia in a sialic-acid dependent manner. A higher level of baseline phagocytosis by microglia from CD22−/− mice was not observed, suggesting that differences in baseline phagocytosis are only detectable by this ex vivo assay in older CD22−/− mice (e.g., 18-months-old) which are not readily available.

Among the histological hallmarks of brain ageing, increased expression of CD68, a lysosome-associated protein, in microglia may indicate impaired degradation of phagocytic prey[44,45]. To test whether CD22 is participates in microglial phagocytosis in vivo, the accumulation of CD68+ microglia in the hippocampus of middle-aged CD22−/− mice and wild-type age-matched control mice by were compared by immunofluorescence (FIG. 4g). Fewer CD68+ microglia in the knockout background (FIG. 4h) were detected, indicating that microglia in the absence of inhibitory CD22 signaling are more capable of degrading lysosomal debris with age. Because disruption of CD22-signaling mimics exposure to young serum and rescues phagocytosis in aged but not young microglia, targeting the CD22 axis promotes homeostatic eating rather than a pro-inflammatory hyperphagic state. Although insufficient clearance of Aβ contributes to Alzheimer's disease pathogenesis, early synapse loss due to excessive microglial phagocytosis also drives cognitive decline, indicating that modulating homeostatic phagocytosis is a critical objective. Microglia in aged CD22−/− mice contain fewer accumulations of CD68, a lysosomal protein that increases with age compared to age-matched, wild-type control mice (FIGS. 4g and 4h). In the absence of inhibitory CD22 signaling, microglia are more capable of maintaining homeostats and degrading lysosomal debris with age, indicating that blockade of CD22-sialic acid signaling in Alzheimer's disease improves the clearance of Aβ while sparing synapses to ameliorate cognitive decline.

Although the invention is not confined to a specific mechanism, results of the experimental examples herein suggest that CD22 on aged microglia binds an unknown sialylated pro-phagocytic receptor in cis, thereby self-inhibiting phagocytosis, and that endogenous sialidases[46] present in a young circulation disinhibit aged phagocytes in the heterochronic parabiosis model. Phagocytosis in the CNS is a tightly regulated process that enables efficient clearance of potentially inflammatory material, with sparing of the interlaced network of vital and delicately woven circuitry. Sialic acid on the surface of microglia and macrophages contributes to the reversible age-related impairment in phagocytosis. CRISPR-Cas9 knockout screens used as a drug target identification platform identify genes necessary for the pro-phagocytic effect of young serum, and indicate that the sialic acid biosynthesis pathway in young serum modulates phagocytosis. Knocking out a key enzyme in sialic acid synthesis, cytidine monophosphate N-acetylneuraminic acid synthetase (CMAS), recapitulates the pro-phagocytic effect of young serum, and α2-6-linked cell-surface sialic acid is sufficient to inhibit phagocytosis. Surprisingly, CD22, a receptor typically expressed on B-cells, is upregulated on aged microglia where it inhibits phagocytosis in a sialic acid dependent manner. Because removal of cell-surface sialic acid, or blockade of CD22, restores phagocytosis in aged but not young microglia, targeting this axis promotes homeostatic eating rather than a pro-inflammatory hyperphagic state. Sialic acid inhibits macrophage and microglial phagocytosis with age, removal of cell-surface sialic acid rejuvenates macrophage and microglial cells, and CD22 mediates the sialic-acid dependent impairment of microglia in the ageing brain.

In some embodiments, methods and compositions of the present invention comprise inhibition of one or more sialotransferases including, for example, sialotransferase ST6GAL1 with inhibition by, for example, an antibody, a small molecule, and/or a peptide. Methods and compositions for sialotransferase inhibition are provided, for example, by Manhardt C. T. et al. J Biol Chem 2017:292; 13524-13520, and Lee M. M. et al. J Biol Chem 2014:289; 8742-8748, each which is incorporated by reference herein in its entirety.

In some embodiments, methods and compositions of the present invention comprise de novo peptide targeted therapeutics as described, for example, by Chevalier A. et al. Nature Publishing Group 2017:550; 74-79 incorporated by reference herein in its entirety.

In some embodiments, compositions comprising oligomeric antisense compounds, particularly oligonucleotides are used to modulate the function of nucleic acid molecules encoding CD22, ultimately modulating the amount of CD22 expressed. This is accomplished by providing antisense compounds that specifically hybridize with one or more nucleic acids encoding CD22. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of CD22. In the context of the present disclosure, "modulation" means either an increase (stimulation) or a decrease (inhibition) in the expression of a gene. For example, CD22 expression may be inhibited to treat or prevent a dementia, atherosclerosis or cancer. Exemplary antisense compounds comprise CMAS sgRNAs: 5-GTT TCA GAA CTT CTT CGA-3' (SEQ ID NO. 1), and 5'-GAG GCG CCA TCA GTT TCG A-3' (SEQ ID NO. 2), and CD22 sgRNAs: 5'-GAC ACG TGG CTT CGG CT-3' (SEQ ID NO. 3) and 5'-GGT GAT GGA GGT GAC AGA AG-3' (SEQ ID NO. 4).

In some embodiments, nucleic acids are small RNAs, for example, siRNAs. "RNA interference (RNAi)" is the process of sequence-specific, post-transcriptional gene silencing initiated by a small interfering RNA (siRNA). During RNAi, siRNA induces degradation of target mRNA with consequent sequence-specific inhibition of gene expression.

An "RNA interference," "RNAi," "small interfering RNA" or "short interfering RNA" or "siRNA" or "short hairpin RNA" or "shRNA" molecule, or "miRNA" is a RNA duplex of nucleotides that is targeted to a nucleic acid sequence of interest, for example, CD22. As used herein, the term "siRNA" is a generic term that encompasses all possible RNAi triggers. An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. certain embodiments, the siRNAs are targeted to the sequence encoding CD22. In some embodiments, the length of the duplex of siRNAs is less than 30 base pairs. In some embodiments, the duplex can be 32, 31, 30, 29, 28, 27, 26, 25, 24, 23, 22, 21, 20, 19, 18, 17, 16, 15, 14, 13, 12, 11 or 10 base pairs in length. In some embodiments, the length of the duplex is 19 to 32 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24, 25, 26 or 27 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

As used herein, Dicer-substrate RNAs (DsiRNAs) are chemically synthesized asymmetric 25-mer/27-mer duplex RNAs that have increased potency in RNA interference compared to traditional siRNAs. Traditional 21-mer siRNAs are designed to mimic Dicer products and therefore bypass interaction with the enzyme Dicer. Dicer has been recently shown to be a component of RISC and involved with entry of the siRNA duplex into RISC. Dicer-substrate siRNAs are designed to be optimally processed by Dicer and show increased potency by engaging this natural processing pathway. Using this approach, sustained knockdown has been regularly achieved using sub-nanomolar concentrations. (U.S. Pat. No. 8,084,599; Kim et al., Nature Biotechnology 23:222 2005; Rose et al., Nucleic Acids Res., 33:4140 2005).

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional siRNAs. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional miRNAs or siRNAs. "Artificial miRNA" or an "artificial miRNA shuttle vector", as used herein interchangeably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (about 35 nucleotides upstream and about 40 nucleotides downstream) arise from restriction enzyme sites within the multiple cloning site of the siRNA. As used herein the term "miRNA" encompasses both the naturally occurring miRNA sequences as well as artificially generated miRNA shuttle vectors.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

The present disclosure contemplates the use of any genetic manipulation for use in modulating the expression of CD22. Examples of genetic manipulation include, but are not limited to, gene knockout (e.g., removing the CD22 gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Exemplary methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present disclosure, vectors are administered into tumors or tissue associated with tumors using direct injection. In other embodiments, administration is via the blood or lymphatic circulation (See e.g., PCT publication 1999/02685 herein incorporated by reference in its entirety). Exemplary dose levels of adenoviral vector are preferably $10^8$ to $10^{11}$ vector particles added to the perfusate.

In some embodiments, the present disclosure provides antibodies that inhibit CD22. Any suitable antibody (e.g., monoclonal, polyclonal, or synthetic) may be utilized in the therapeutic methods disclosed herein. In some embodiments, the antibodies are humanized antibodies. Methods for humanizing antibodies are well known in the art (See e.g., U.S. Pat. Nos. 6,180,370, 5,585,089, 6,054,297, and 5,565,332; each of which is herein incorporated by reference).

The present invention is not limited to the use of any particular antibody configuration. In some preferred embodiments, the targeting unit is an antigen binding protein. Preferred antigen binding proteins include, but are not limited to an immunoglobulins, a Fab, F(ab')2, Fab' single chain antibody, Fv, single chain (scFv), mono-specific antibody, bi-specific antibody, tri-specific antibody, multivalent antibody, chimeric antibody, humanized antibody, human antibody, CDR-grafted antibody, shark antibody, an immunoglobulin single variable domain (e.g., a nanobody or a single variable domain antibody), minibody, camelid antibody (e.g., from the Camelidae family) microbody, intrabody (e.g., intracellular antibody), and/or de-fucosylated antibody and/or derivative thereof. Mimetics of binding agents and/or antibodies are also provided.

In some embodiments, scFv polypeptides described herein are fused to Fc regions to generate minibodies. As used herein, the term "fragment crystallizable region (Fc region)" refers to the tail region of an antibody that interacts with cell surface receptors called Fc receptors and some proteins of the complement system. This property allows antibodies to activate the immune system. In IgG, IgA and IgD antibody isotypes, the Fc region is composed of two identical protein fragments, derived from the second and third constant domains of the antibody's two heavy chains; IgM and IgE Fc regions contain three heavy chain constant domains (CH domains 2-4) in each polypeptide chain. The Fc regions of IgGs bear a highly conserved N-glycosylation site.

In some embodiments, the Fc region is derived from an IgG. In some embodiments, the IgG is human IgG1, although other suitable Fc regions derived from other organisms or antibody frameworks may be utilized.

In some embodiments, scFv polypeptides described herein are fused to chimeric antigen receptors. Chimeric antigen receptors (CARs), (also known as chimeric immunoreceptors, chimeric T cell receptors, artificial T cell receptors or CAR-T) are engineered receptors, which graft an arbitrary specificity onto an immune effector cell (T cell). Typically, these receptors are used to graft the specificity of an antibody (e.g., an scFv described herein) onto a T cell, with transfer of their coding sequence facilitated by retroviral vectors. The receptors are called chimeric because they are composed of parts from different sources.

Further, the present invention also envisages expression vectors comprising nucleic acid sequences encoding any of the above polypeptides or fusion proteins thereof or functional fragments thereof, as well as host cells expressing such expression vectors. Suitable expression systems include constitutive and inducible expression systems in bacteria or yeasts, virus expression systems, such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris*, and the like. Suitable animal host cells include HEK 293, COS, S2, CHO, NSO, DT40 and the like. The cloning, expression and/or purification of the antibodies can be done according to techniques known by the skilled person in the art.

It will be understood that polypeptides described herein may be identified with reference to the nucleotide and/or amino acid sequence corresponding to the variable and/or complementarity determining regions ("CDRs") thereof.

Also within the scope of the invention are natural or synthetic analogs, mutants, variants, alleles, homologs and orthologs (herein collectively referred to as "variants") of the immunoglobulin single variable domains of the invention as defined herein. Thus, according to one embodiment of the invention, the term "immunoglobulin single variable domain of the invention" in its broadest sense also covers such variants, in particular variants of the antibodies described herein. Generally, in such variants, one or more amino acid residues may have been replaced, deleted and/or added compared to the antibodies of the invention as defined herein. Such substitutions, insertions or deletions may be made in one or more of the framework regions and/or in one or more of the CDRs. Variants, as used herein, are sequences wherein each or any framework region and each or any complementarity determining region shows at least 80% identity, preferably at least 85% identity, more preferably 90% identity, even more preferably 95% identity or, still even more preferably 99% identity with the corresponding region in the reference sequence (i.e., FR1_variant versus FR1_reference, CDR1_variant versus CDR1_reference, FR2_variant versus FR2_reference, CDR2_variant versus CDR2_reference, FR3_variant versus FR3_reference, CDR3_variant versus CDR3_reference, FR4_variant versus FR4_reference), as can be measured electronically by making use of algorithms such as PILEUP and BLAST. (See, e.g., Higgins & Sharp, CABIOS 5:151 (1989); Altschul S. F., W. Gish, W. Miller, E. W. Myers, D. J. Lipman. Basic local alignment search tool. J. Mol. Biol. 1990; 215:403-10.) Software for performing BLAST analyses is publicly available through the National Center for Biotechnology Information (on the worldwide web at ncbi.nlm.nih.gov/). Such variants of immunoglobulin single variable domains may be of particular advantage since they may have improved potency or other desired properties.

A "deletion" is defined here as a change in either amino acid or nucleotide sequence in which one or more amino acid or nucleotide residues, respectively, are absent as compared to an amino acid sequence or nucleotide sequence of a parental polypeptide or nucleic acid. Within the context of a protein, a deletion can involve deletion of about two, about five, about ten, up to about twenty, up to about thirty or up to about fifty or more amino acids. A protein or a fragment thereof may contain more than one deletion.

An "insertion" or "addition" is that change in an amino acid or nucleotide sequences which has resulted in the addition of one or more amino acid or nucleotide residues, respectively, as compared to an amino acid sequence or nucleotide sequence of a parental protein. "Insertion" generally refers to addition to one or more amino acid residues within an amino acid sequence of a polypeptide, while "addition" can be an insertion or refer to amino acid residues added at an N- or C-terminus, or both termini. Within the context of a protein or a fragment thereof, an insertion or addition is usually of about one, about three, about five, about ten, up to about twenty, up to about thirty or up to about fifty or more amino acids. A protein or fragment thereof may contain more than one insertion.

A "substitution," as used herein, results from the replacement of one or more amino acids or nucleotides by different amino acids or nucleotides, respectively as compared to an amino acid sequence or nucleotide sequence of a parental protein or a fragment thereof. It is understood that a protein or a fragment thereof may have conservative amino acid substitutions which have substantially no effect on the protein's activity. By conservative substitutions is intended combinations such as gly, ala; val, ile, leu, met; asp, glu; asn, gln; ser, thr; lys, arg; cys, met; and phe, tyr, trp.

By means of non-limiting examples, a substitution may, for example, be a conservative substitution (as described herein) and/or an amino acid residue may be replaced by another amino acid residue that naturally occurs at the same position in another variable domain. Thus, any one or more substitutions, deletions or insertions, or any combination thereof, that either improve the properties of the antibody of the invention or that at least do not detract too much from the desired properties or from the balance or combination of desired properties of the antibody of the invention (i.e., to the extent that the antibody is no longer suited for its intended use) are included within the scope of the invention. A skilled person will generally be able to determine and select suitable substitutions, deletions or insertions, or suitable combinations of thereof, based on the disclosure herein and optionally after a limited degree of routine experimentation, which may, for example, involve introducing a limited number of possible substitutions and determining their influence on the properties of the antibodies thus obtained.

Further, depending on the host organism used to express the immunoglobulin single variable domain of the invention, such deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example, to allow site-specific pegylation.

Examples of modifications, as well as examples of amino acid residues within the immunoglobulin single variable domain, that can be modified (i.e., either on the protein backbone but preferably on a side chain), methods and techniques that can be used to introduce such modifications and the potential uses and advantages of such modifications will be clear to the skilled person. For example, such a modification may involve the introduction (e.g., by covalent linking or in another suitable manner) of one or more functional groups, residues or moieties into or onto the immunoglobulin single variable domain of the invention, and in particular of one or more functional groups, residues or moieties that confer one or more desired properties or functionalities to the immunoglobulin single variable domain of the invention. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFvs and single domain antibodies), for which reference is, for example, made to Remington's Pharmaceutical Sciences, 16th ed., Mack Publishing Co., Easton, Pa. (1980). Such functional groups may, for example, be linked directly (for example, covalently) to an immunoglobulin single variable domain of the invention, or optionally via a suitable linker or spacer, as will again be clear to the skilled person. One of the most widely used techniques for increasing the half-life and/or reducing immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFvs); reference is made to, for example, Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO04060965. Various reagents for pegylation of proteins are also commercially available, for example, from Nektar Therapeutics, USA. Preferably, site-directed pegylation is used, in particular via a cysteine-residue (see, for example, Yang et al., Protein Engineering, 16, 10, 761-770 (2003). For example, for this purpose, PEG may be attached to a cysteine residue that naturally occurs in an antibody of the invention, an antibody of the invention may be modified so as to suitably introduce one or more cysteine residues for attachment of PEG, or an amino acid sequence comprising one or more cysteine residues for attachment of PEG may be fused to the N- and/or C-terminus of a antibody of the invention, all using techniques of protein engineering known per se to the skilled person. Preferably, for the immunoglobulin single variable domains and proteins of the invention, a PEG is used with a molecular weight of more than 5000, such as more than 10,000 and less than 200,000, such as less than 100,000; for example, in the range of 20,000-80,000. Another, usually less preferred modification comprises N-linked or O-linked glycosylation, usually as part of co-translational and/or post-translational modification, depending on the host cell used for expressing the immunoglobulin single variable domain or polypeptide of the invention. Another technique for increasing the half-life of an immunoglobulin single variable domain may comprise the engineering into bifunctional constructs or into fusions of immunoglobulin single variable domains with peptides (for example, a peptide against a serum protein such as albumin).

Yet another modification may comprise the introduction of one or more detectable labels or other signal-generating groups or moieties, depending on the intended use of the labeled antibody. Suitable labels and techniques for attaching, using and detecting them will be clear to the skilled person and, for example, include, but are not limited to, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person and, for example, include moieties that can be detected using NMR or ESR spectroscopy. Such labeled antibodies and polypeptides of the invention may, for example, be used for in vitro, in vivo or in situ assays (including immunoassays known per se such as ELISA, RIA, EIA and other "sandwich assays," etc.), as well as in vivo diagnostic and imaging purposes, depending on the choice of the specific label. As will be clear to the skilled person, another modification may involve the introduction of a chelating group, for example, to chelate one of the metals or metallic cations referred to above. Suitable chelating groups, for example, include, without limitation, diethylenetriaminepentaacetic acid (DTPA) or ethylenediaminetetraacetic acid (EDTA). Yet another modification may comprise the introduction of a functional group that is one part of a specific binding pair, such as the biotin-(strept)avidin binding pair. Such a functional group may be used to link the antibody of the invention to another protein, polypeptide or chemical compound that is bound to the other half of the binding pair, i.e., through formation of the binding pair. For example, an antibody of the invention may be conjugated to biotin, and linked to another protein, polypeptide, compound or carrier conjugated to avidin or streptavidin. For example, such a conjugated antibody may be used as a reporter, for example, in a diagnostic system where a detectable signal-producing agent is conjugated to avidin or streptavidin. Such binding pairs may, for example, also be used to bind the antibody of the invention to a carrier, including carriers suitable for pharmaceutical purposes. One non-limiting example are the liposomal formulations described by Cao and Suresh, Journal of Drug Targeting, 8, 4, 257 (2000). Such binding pairs may also be used to link a therapeutically active agent to the antibody of the invention.

In some embodiments, the immunoglobulin single variable domain of the present invention is fused to a detectable label, either directly or through a linker. Preferably, the detectable label is a radio-isotope or radioactive tracer, which is suitable for medical applications, such as in in vivo nuclear imaging. Examples include, without the purpose of being limitative, $^{99}$mTc, $^{123}$I, $^{125}$I, $^{111}$In, $^{18}$F, $^{64}$Cu, $^{67}$Ga, $^{68}$Ga, and any other radio-isotope which can be used in animals, in particular mouse or human.

In still another embodiment, the immunoglobulin single variable domain of the present invention is fused to a moiety selected from the group consisting of a toxin, or to a cytotoxic drug, or to an enzyme capable of converting a prodrug into a cytotoxic drug, or to a radionuclide, or coupled to a cytotoxic cell, either directly or through a linker.

In some embodiments, the present invention provides an antibody-drug conjugate and/or an antibody-enzyme conjugate comprising, for example, a CD22 antibody linked to 3Fax-NeuAc, and/or a CD22 antibody linked to a sialidase. In certain embodiments, the antibody drug conjugates are administered to cells expressing CD22.

As used herein, "linkers" are peptides of 1 to 50 amino acids length and are typically chosen or designed to be unstructured and flexible. These include, but are not limited to, synthetic peptides rich in Gly, Ser, Thr, Gln, Glu or further amino acids that are frequently associated with unstructured regions in natural proteins. (See, e.g., Dosztanyi Z., V. Csizmok, P. Tompa, and I. Simon (2005). IUPred: web server for the prediction of intrinsically unstructured regions of proteins based on estimated energy content. Bioinformatics (Oxford, England), 21(16), 3433-4.)

In some embodiments, the therapeutic polypeptide is an immunoglobulin or fragment thereof. Examples include, but are not limited to, aptamers and immunoglobulins. Immunoglobulins (antibodies) are proteins generated by the immune system to provide a specific molecule capable of complexing with an invading molecule commonly referred to as an antigen. Natural antibodies have two identical antigen-binding sites, both of which are specific to a particular antigen. The antibody molecule recognizes the antigen by complexing its antigen-binding sites with areas of the antigen termed epitopes. The epitopes fit into the conformational architecture of the antigen-binding sites of the antibody, enabling the antibody to bind to the antigen.

The immunoglobulin molecule is composed of two identical heavy and two identical light polypeptide chains, held together by interchain disulfide bonds. Each individual light and heavy chain folds into regions of about 110 amino acids, assuming a conserved three-dimensional conformation. The light chain comprises one variable region (termed $V_L$) and one constant region ($C_L$), while the heavy chain comprises one variable region ($V_H$) and three constant regions ($C_H1$, $C_H2$ and $C_H3$). Pairs of regions associate to form discrete structures. In particular, the light and heavy chain variable regions, $V_L$ and $V_H$, associate to form an "Fv" area that contains the antigen-binding site.

The variable regions of both heavy and light chains show variability in structure and amino acid composition from one antibody molecule to another, whereas the constant regions show little variability. Each antibody recognizes and binds an antigen through the binding site defined by the association of the heavy and light chain, variable regions into an Fv area. The light-chain variable region $V_L$ and the heavy-chain variable region $V_H$ of a particular antibody molecule have specific amino acid sequences that allow the antigen-binding site to assume a conformation that binds to the antigen epitope recognized by that particular antibody.

Within the variable regions are found regions in which the amino acid sequence is extremely variable from one antibody to another. Three of these so-called "hypervariable" regions or "complementarity-determining regions" (CDR's) are found in each of the light and heavy chains. The three CDRs from a light chain and the three CDRs from a corresponding heavy chain form the antigen-binding site.

Cleavage of naturally occurring antibody molecules with the proteolytic enzyme papain generates fragments that retain their antigen-binding site. These fragments, commonly known as Fab's (for Fragment, antigen binding site) are composed of the $C_L$, $V_L$, $C_H1$ and $V_H$ regions of the antibody. In the Fab the light chain and the fragment of the heavy chain are covalently linked by a disulfide linkage.

Monoclonal antibodies against target antigens (e.g., CD22, CMAS) are produced by a variety of techniques including conventional monoclonal antibody methodologies such as the somatic cell hybridization techniques of Kohler and Milstein, Nature, 256:495 (1975). Although in some embodiments, somatic cell hybridization procedures are preferred, other techniques for producing monoclonal antibodies are contemplated as well (e.g., viral or oncogenic transformation of B lymphocytes).

A preferred animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

Human monoclonal antibodies (mAbs) directed against human proteins can be generated using transgenic mice carrying the complete human immune system rather than-the mouse system. Splenocytes from the transgenic mice are immunized with the antigen of interest, which are used to produce hybridomas that secrete human mAbs with specific affinities for epitopes from a human protein. (See e.g., Wood et al., WO 91/00906, Kucherlapati et al., WO 91/10741; Lonberg et al., WO 92/03918; Kay et al., WO 92/03917 (each of which is herein incorporated by reference in its entirety); N. Lonberg et al., Nature, 368:856-859 [1994]; L. L. Green et al., Nature Genet., 7:13-21 [1994]; S. L. Morrison et al., Proc. Nat. Acad. Sci. USA, 81:6851-6855 [1994]; Bruggeman et al., Immunol., 7:33-40 [1993]; Tuaillon et al., Proc. Nat. Acad. Sci. USA, 90:3720-3724 [1993]; and Bruggernan et al. Eur. J. Immunol., 21:1323-1326 [1991]).

Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies. (See e.g., Sastry et al., Proc. Nat. Acad. Sci. USA, 86:5728 [1989]; Huse et al., Science, 246:1275 [1989]; and Orlandi et al., Proc. Nat. Acad. Sci. USA, 86:3833 [1989]). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and the PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies. (See e.g., Larrick et al., Biotechniques, 11:152-156 [1991]). A similar strategy can also be used to amplify human heavy and light chain variable regions from human antibodies (See e.g., Larrick et al., Methods: Companion to Methods in Enzymology, 2:106-110 [1991]).

The term modified antibody is also intended to include antibodies, such as monoclonal antibodies, chimeric antibodies, and humanized antibodies which have been modified by, for example, deleting, adding, or substituting portions of the antibody. For example, an antibody can be modified by deleting the hinge region, thus generating a monovalent antibody. Any modification is within the scope of the invention so long as the antibody has at least one antigen binding region specific.

Chimeric mouse-human monoclonal antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (See e.g., Robinson et al., PCT/US86/02269; European Patent Application 184,187; European Patent Application 171,496; European Patent Application 173,494; WO 86/01533; U.S. Pat. No. 4,816,567; European Patent Application 125,023 (each of which is herein incorporated by reference in its entirety]); Better et al., Science, 240:1041-1043 (1988); Liu et al., Proc. Nat. Acad. Sci. USA, 84:3439-3443 (1987); Liu et al., J. Immunol., 139:3521-3526 (1987); Sun et al., Proc. Nat. Acad. Sci. USA, 84:214-218 (1987); Nishimura et al., Canc. Res., 47:999-1005 (1987); Wood et al., Nature, 314: 446-449 (1985); and Shaw et al., J. Natl. Cancer Inst., 80:1553-1559 (1988)).

The chimeric antibody can be further humanized by replacing sequences of the Fv variable region that are not directly involved in antigen binding with equivalent sequences from human Fv variable regions. General reviews of humanized chimeric antibodies are provided by S. L. Morrison, Science, 229:1202-1207 (1985) and by Oi et al., Bio. Techniques, 4:214 (1986). Those methods include isolating, manipulating, and expressing the nucleic acid sequences that encode all or part of immunoglobulin Fv variable regions from at least one of a heavy or light chain. Suitable humanized antibodies can alternatively be produced by CDR substitution (e.g., U.S. Pat. No. 5,225,539 (incorporated herein by reference in its entirety); Jones et al., Nature, 321:552-525 (1986); Verhoeyan et al., Science, 239:1534 (1988); and Beidler et al., J. Immunol., 141:4053 (1988)). All of the CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method that is capable of replacing at least a portion of a CDR of a human antibody with a CDR derived from a non-human antibody. The human CDRs may be replaced with non-human CDRs; using oligonucleotide site-directed mutagenesis.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances.

The antibodies can be of various isotypes, including, but not limited to: IgG (e.g., IgG1, IgG2, IgG2a, IgG2b, IgG2c, IgG3, IgG4); IgM; IgA1; IgA2; IgA$_{sec}$; IgD; and IgE. In some preferred embodiments, the antibody is an IgG isotype. In other preferred embodiments, the antibody is an IgM isotype. The antibodies can be full-length (e.g., an IgG1, IgG2, IgG3, or IgG4 antibody) or can include only an antigen-binding portion (e.g., a Fab, F(ab')$_2$, Fv or a single chain Fv fragment).

In preferred embodiments, the immunoglobulin is a recombinant antibody (e.g., a chimeric or a humanized antibody), a subunit, or an antigen binding fragment thereof (e.g., has a variable region, or at least a complementarity determining region (CDR)).

In some embodiments, the immunoglobulin is monovalent (e.g., includes one pair of heavy and light chains, or antigen binding portions thereof). In other embodiments, the immunoglobulin is a divalent (e.g., includes two pairs of heavy and light chains, or antigen binding portions thereof).

In some embodiments, recombinant CD22 fusion proteins that block sialosides are provided. Where clinical applications are contemplated, in some embodiments of the present invention, the fusion proteins are prepared as part of a pharmaceutical composition in a form appropriate for the intended application. Generally, this entails preparing compositions that are essentially free of pyrogens, as well as other impurities that could be harmful to humans or animals. However, in some embodiments of the present invention, a fusion protein composition formulation may be administered using one or more of the routes described herein.

In some embodiments, the fusion protein compositions are used in conjunction with appropriate salts and buffers to render delivery of the compositions in a stable manner to allow for uptake by target cells. Buffers also are employed when the compositions are introduced into a patient. Aqueous compositions comprise an effective amount of composition dispersed in a pharmaceutically acceptable carrier or aqueous medium. Such compositions also are referred to as inocula. In some embodiments, candidate CD22 inhibitors are screened for activity (e.g., using the methods described in the experimental methods or another suitable assay). In certain embodiments, the CD22 inhibitor is a sialoside. In particular embodiments, the sialoside is a high affinity synthetic sialic acid analog and/or selective Siglec glycan ligand including, for example, A 2,3-Dichlorobenzyl derivative, a o-nosyl (ortho-nitrophenylsulfonyl) derivative, a sialoside that contains a dichlorobenzyl substituent at the anomeric position, an ortho-nitrobenzylsulfonamide at the 5-position, and a 4'-hydroxy-4-biphenylcarboxamide at the 9-position, a α-9-N-(biphenyl-4-carbonyl)-amino-9-deoxy-Neu5Ac (BPC-Neu5Ac), a 9-BPC-Neu5Acα2-6Galβ1-4GlcNAc (BPC-Neu5Ac-LacNAc), or a benzyl-Neu5Acα (See, e.g., Mesch et al. Chem Med Chem 7:134-143, 2012, Angata et al. Trends Pharmacological Science 36:645-660, 2015, and Bull et al. Trends in Biochemical Sciences 41:519-531, 2016.) In particular embodiments, cell permeation is enhanced by administration of a high affinity and selectivity glycan ligand as a prodrug, by replacing, for example, the carboxylate with a bioisostere, or by administering high affinity CD22 ligands on the surface of liposomal nanoparticles. Additional CD22 in inhibitors comprise those described by Kelm, S. et al. J Exp Med 2002: 195, 1207-1213, Duong, B. H. et al. J Exp Med 2010:207, 173-187, Collins, B. E. et al. The Journal of Immunology 2006:177, 2994-3003, Kelm, S. et al. Angew. Chem. Int. Ed. 2013:52, 3616-3620, Rillahan, C. D. et al. Chem. Sci. 2014:5, 2398-17, and Mesch, S. et al. Chem Med Chem 2011: 7, 134-143, each of which is incorporated herein in its entirety.

In some embodiments, the CD22 inhibitors and agents that decrease cell surface sialic acid are delivered to the CNS by methods and compositions that promote transfer across the blood brain barrier (BBB). In certain embodiments, the methods and compositions comprise one or more bi-specific antibodies comprising, for example, antibodies to highly expressed proteins, including basigin, Glut1, and CD98hc. Antibodies to these targets are significantly enriched in the brain after administration in vivo. In particular, antibodies against CD98hc show robust accumulation in brain after systemic dosing. Accordingly, in specific embodiments, methods and compositions of the present invention comprise, for example, use of CD98hc as a robust receptor-mediated transcytosis pathway for antibody delivery to the brain. (Zuchero et al. Neuron 89; 70-82, 2016.) In further embodiments, transfer across the BBB is enhanced by transient disruption, for example, osmotic or pharmacologic disruption, and/or by other membrane protein pathways using receptor-mediate transcytosis comprising, for example, antibodies against the transferrin receptor.

In some embodiments, the present invention provides methods and compositions for inhibiting CMAS activity comprising, for example, methods and compositions that inhibit CMAS transcription, translation, and expression, that promote CMAS degradation, and/or that antagonize CMAS activity comprising, for example, a nucleic acid (of use, for example, in CMAS RNA inhibition), an antibody, a small molecule or a combination thereof. In particular embodiments, two or more methods and compositions that inhibit CMAS, that inhibit CD22 and that inhibit sialidase activity are provided in combination.

The present disclosure further provides pharmaceutical compositions (e.g., comprising the compounds described above). The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. In certain embodiments, CD22 inhibitors and agents that decrease cell surface sialic acid are administered by methods that bypass the BBB including, for example, direct application to the surface of the CNS, to the parenchyma of the CNS, to the ventricles of the CNS, and to the cerebrospinal fluid (CSF) of the CNS. In particular, intrathecal and epidural administration may be achieved by single shot, a series of single shots, and/or by continuous administration to the CSF. In certain embodiments, continuous administration to the CSF is provided by a programmable external pump. In other embodiments, continuous administration is provided by a programmable implantable pump.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, liquid syrups, soft gels, suppositories, and enemas. The compositions of the present disclosure may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Agents that enhance uptake of oligonucleotides at the cellular level may also be added to the pharmaceutical and other compositions of the present disclosure. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present disclosure may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present disclosure, such as dyes, flavoring agents, preservatives, antioxidants, opacifiers, thickening agents and stabilizers. However, such materials, when added, should not unduly interfere with the biological activities of the components of the compositions of the present disclosure. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on EC50s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

EXPERIMENTAL METHODS

The following examples are provided in order to demonstrate and further illustrate certain embodiments and aspects of the present disclosure and are not to be construed as limiting the scope thereof. In particular, experimental methods described herein may be configured for research use to investigate cellular phagocytosis and cellular ageing including, for example, the ageing of cells that participate in phagocytosis.

Animals

Aged male C57BL/6 mice were obtained from the National Institute on Aging rodent colony. Young male C57BL/6 mice were obtained from Jackson Laboratories or Charles River Laboratories. CD22−/− mice were generated by L. Nitschke (University of Erlangen). All animal care and procedures complied with the Animal Welfare Act and were in accordance with institutional guidelines and approved by the V. A. Palo Alto Committee on Animal Research and the institutional administrative panel of laboratory animal care at Stanford University.

Cell Culture

BV2 cells were originally obtained from E. Blasi (Università di Modena e Reggio Emilia) and expanded in DMEM supplemented with 10% FBS, penicillin/streptomycin, and GlutaMAX (Thermo Fisher Scientific). For young mouse serum treatments, blood was collected in EDTA and pooled from 1.5-2-month old mice by cardiac puncture and spun down at 1000 g for 15 minutes to isolate plasma. Plasma was dialyzed against PBS at room temperature for 45 minutes then at 4 degrees overnight using 3.5 kDa Slide-a-Lyzer casettes (ThermoFisher). To avoid clotting while minimizing destruction of protein activity, plasma-derived serum was prepared by diluting dialyzed plasma to 5% in room temperature DMEM and allowing the mixture to clot for 15-30 minutes. Clotted plasma was filtered through a 0.22 µm PES membrane to obtain plasma-derived serum. 24 hours prior to phagocytosis assays, BV2 cells were washed twice with PBS and cultured in serum-free DMEM or DMEM containing 5% young mouse serum. HEK293T cells were cultured in DMEM supplemented with 10% FBS, penicillin/streptomycin, and GlutaMAX. All cells were maintained in a humidified incubator containing 5% $CO_2$ at 37° C.

Flow Cytometry

Antibodies to CD11b (clone M1/70, BioLegend) and CD45 (clone 30-F11, Biolegend) were used for microglia identification (CD11b+CD45lo). For primary microglia immunophenotyping, the following lectins and antibodies were used: biotinylated *Sambucus nigra* agglutinin (SNA, Vector Labs), biotinylated *Maackia amurensis* agglutinins (MAA-1 and MAA-2, Vector), biotinylated *Erythrina cristagalli* lectin (ECL, EY Labs), biotinylated wheat germ agglutinin (WGA, Vector), recombinant mouse Siglec-E (R&D), recombinant mouse Siglec-F (R&D), antibodies to mouse Siglec-1 (clone REA197, Miltenyi Biotec), CD22 (clone OX-97, Biolegend), Siglec-E (clone M1304A01, Biolegend), Siglec-F (clone ES22-10D8, Miltenyi Biotec), Siglec-G (clone SH1, BD Biosciences), Siglec-H (clone 551, Biolegend), CD33 (clone 9A11, eBioscience), Galectin-3 (clone M3/38, Biolegend). For immunostaining, cells were passed through a 100 µm strainer, blocked for 10 minutes on ice with mouse Fc-blocking reagent (BD), and stained for 30 minutes on ice in DPBS containing calcium and magnesium supplemented with 1% bovine serum albumin. When biotinylated antibodies or lectins were used, cells were stained with APC-Cy7-conjugated streptavidin (Biolegend) for 15 minutes on ice following primary stain. When recombinant Siglecs were used, they were precomplexed with APC-Cy7-conjugated anti-human IgG Fc (Biolegend) on ice at 10 µg/mL each. The complex was used at 1:2 for a final staining concentration of 5 µg/mL. Live cells were identified using Sytox Blue viability dye. Flow cytometry analysis was performed on a BD LSRFortessa and sorting was performed on a BD FACSAria III. Data was analyzed using FlowJo software (TreeStar).

CRISPR-Cas9 Screen

The 10-sgRNA-per-gene CRISPR/Cas9 deletion library was synthesized, cloned, and infected into Cas9-expressing BV2 cells as previously described[24]. ~12 million (for Membrane Proteins sub-library) or ~24 million (for Drug Targets, Kinases, Phosphatases sub-library) BV2 cells stably expressing EF1alpa-Cas9-BLAST were infected with the 10 guide/gene sgRNA sub-libraries at an MOI<1. Infected cells underwent puromycin selection (1.5 µg/mL) for 5 days after which point puromycin was removed and cells were resuspended in normal growth media without puromycin. After selection, sgRNA infection was confirmed by flow cytometry, which indicated >90% of cells expressed the mCherry reporter. Sufficient sgRNA library representation was confirmed by deep sequencing after selection. At the conclusion of each screen, genomic DNA was extracted for screen populations separately according to the QIAGEN Blood Maxi Kit protocol. Using known universal sequences present in the lentivirally-incorporated DNA, sgRNA sequences were amplified and prepared for sequencing by two sequential PCR reaction as previously described (Morgens et al., 2016). Products were sequenced using an Illumina Nextseq to monitor library composition (30 to 40 million reads per library). Trimmed sequences were aligned to libraries using Bowtie, with zero mismatches tolerated, and all alignments from multi-mapped reads included. Enrichment of individual sgRNAs was calculated as a median-normalized log-ratio of the fraction of counts. Guide composition and comparisons across bound and unbound fractions was analyzed using casTLE (Morgens et al., 2016) version 1.0 at https://bitbucket.org/dmorgens/castle.

Cells were cultured 1 week at 1,000× coverage (~1,000 cells containing each sgRNA) and 1,000× coverage was maintained throughout the screen. Phagocytic screening prey were prepared by labeling 3 µm amino-coated polystyrene particles (Polysciences) with CypHer5E pH-dependent fluorescent dye (GE Life Sciences). At the end of each screen genomic DNA was extracted for all populations separately using a QIAGEN Blood Midi Kit. Deep sequencing of sgRNA sequences on an Illumina Nextseq was used to monitor library composition. Guide composition was analyzed and compared to the plasmid library and between conditions using casTLE27 version 1.0 available at https://bitbucket.org/dmorgens/castle.

In Vitro Phagocytosis Validation

For in vitro phagocytosis assays, cells were split into a 24-well plate 8-24 hours prior to serum treatment at a density of 50,000 cells/well. Following specific treatments, wells were washed twice with PBS and fed pHrodo-labeled 3 µm amino-coated polystyrene particles (Polysciences) at a ratio of 10 particles per cell or crude myelin, isolated as previously described[47], at 1 mg/mL. pHrodo labeling was carried out as previously described to minimize background fluorescence[37]. 4 phase and red fluorescent images per well were acquired every hour for 24 hours using the Incucyte S3 live cell analysis system (Essen Bioscience). For each time point, normalized phagocytosis was calculated using the following formula: red object area/phase confluence. To combine data from independent experiments, phagocytosis was calculated relative to control by setting phagocytosis at zero hours in the no serum control cell condition to 0, and this value at 24 hours to 1. Technical triplicates for each experiment were averaged, and the average of three independent experiments was reported.

Lentivirus Production and Infection

Lentivirus production and infection was performed as previously described[24]. HEK293T cells were transfected with packaging plasmids and sgRNA-containing plasmids. Supernatant was harvested at 48 hours and 72 hours and concentrated with Lenti-X solution (Clontech). BV2 cells stably expressing Cas9 endonuclease under blasticidin (1 µg/mL) selection were spin infected with lentivirus containing sgRNA plasmids under puromycin selection. Puromycin selection (1.5 µg/mL) was started 48 hours after infection and maintained for 7 days. Antibiotic selection was subsequently removed for expansion and freezing. CMAS knockout BV2 cells were sub-cloned by single-cell sorting to obtain a monoclonal `out population. Other single-knockout cell lines were assayed as a polyclonal population.

Sialidase Expression

Sialidase from *Vibrio cholerae* was prepared as previously described[48]. In brief, *Escherichia coli* C600 transfected with the pCVD364 vector were grown in 2×YT media supplemented with ampicillin (100 m/mL) for 12 hours at 37° C. Cells were collected by centrifugation at 4,500×g for 10 minutes. The pellet was resuspended in osmotic shock buffer (20% sucrose, 1 mM EDTA, 30 mM Tris-HCl, pH 8), incubated for 10 min at RT, then spun at 13,000×g for 10 minutes. The pellet was resuspended in ice cold ddH2O, incubated at 4° C. for 10 min, and then spun at 13,000×g. The supernatant was concentrated using a tangential flow filtration system (Pall Corporation). The concentrate was loaded onto a HiTrap Q HP anion exchange column (GE Healthcare Life Sciences) and eluted using a gradient of NaCl in 20 mM Tris, pH 7.6. Fractions containing sialidase were assessed by SDS-PAGE and pooled. Endotoxins were removed using a high capacity endotoxin removal kit (Thermo Fisher Scientific).

Sialic Acid Inhibition

For sialidase treatment, cells were incubated with 400 nM Vibrio cholerae sialidase for 1 hour at 37° C. in serum-free DMEM following serum treatment and prior to feeding. 3Fax-Neu5Ac (R&D) was used as previously described[33]. The inhibitor was used at a concentration of 32 μM serially diluted in DMSO and used at a final concentration of 0.1% DMSO in DMEM. 3Fax-Neu5Ac was added with serum treatments for 48 hours prior to phagocytosis assays, and replaced in the feeding medium.

Glycopolymer Decoration

Aminooxy glycan-conjugated polymers were based on a methyl vinyl ketone backbone coupled to a dipalmitoylphosphatidylethanolamine lipid anchor. Glycopolymers were conjugated at 70-85% of ketone sites to either N-acetylneuraminic acid-α2-3-lactose or N-acetylneuraminic acid-α2-6-lactose through an oxime linkage. Cells were decorated with aminooxy glycan-conjugated polymers as previously described[35]. Cells were harvested and resuspended in PBS at 107 cells/mL. Labeling was carried out by incubating the cell suspension with 1 μM of the specific polymer for 30 minutes at room temperature with constant gentle agitation. Cells were washed with PBS and split into a 24-well plate at 50,000 cells/well for subsequent phagocytosis assays.

Peritoneal Macrophage Culture

Young or aged C57BL/6 mice were euthanized by approved protocols, and the peritoneal cavity was flooded with 10 mLs of ice-cold PBS with a 26-gauge needle. After gentle agitation of the cavity, peritoneal fluid was collected with a 16-gauge needle and filtered through a 100 μm strainer. Cells were pelleted by centrifugation (300×g, 10 minutes) and resuspended in IMDM supplemented with 10% FBS, penicillin/streptomycin, GlutaMAX and 10 ng/mL of recombinant mouse M-CSF (Peprotech). Non-adherent cells were removed after 24 hours and the phagocytosis assay was performed 24 hours later.

Primary Microglia Isolation

Primary mouse microglia were isolated as previously described[49]. Mice were transcardially perfused with ice-cold HBSS containing glucose and HEPES, and brains were removed into the same medium containing DNAse I. On ice, brains were minced with a razor blade and a single cell suspension was obtained by gentle Dounce homogenization. The suspension was filtered through a 100 μm strainer. Myelin was removed by Percoll density gradient or by magnetic myelin removal beads (Miltenyi Biotec). The remaining myelin-depleted cell suspension was stained with antibodies to distinguish microglia by flow cytometry. Previous studies have demonstrated the intense autofluorescent signal of microglia in the ageing brain, likely due to the accumulation of the age-related pigment, lipofuscin[50,51]. To measure the expression of proteins on aged microglia by flow cytometry, a gating scheme was developed (Extended Data FIG. 3F) to exclude autofluorescent cells (~10% of total microglia) from analysis. Specifically, cells with high side-scatter signal which coincided with the autofluorescent population were excluded. When possible, fluorophores with emission spectra in far red channels (e.g., APC-Cy7) were used.

Ex Vivo Microglial Phagocytosis Assay

Whole brain myelin-depleted single-cell suspensions were prepared as described above. Next, a rough estimation of microglia counts from each brain was determined by strictly gating a volume-designated aliquot of the suspensions by forward scatter/side scatter on a flow cytometer (BD Accuri C6). Each suspension was adjusted to contain equal numbers of microglia per unit volume. Then, single cell brain suspensions were treated with sialidase, a CD22 blocking antibody (R&D), or no treatment for 1 hour at 37° C. with periodic agitation. Treatments were washed out and cells were resuspended in FACS buffer containing pHrodo- or CypHer5E-conjugated particles at a ratio of 50 particles per microglia. The cell-particle mixture was incubated for 1-2 hours at 37° C. with periodic agitation. Phagocytosis was stopped by transferring the suspensions to ice, where the cells were stained with antibodies to distinguish microglia. Microglial phagocytosis was assessed by flow cytometry by pre-gating live CD11b+CD45lo cells and assessing pH dependent particle fluorescence within this population. The eating gate was determined using an unfed control, and confirmed by sorting an aliquot of the sample into noneating and eating populations by FACS followed by microscopic assessment.

qPCR

Microglia were isolated by FACS as described above and sorted into Trizol LS. RNA was prepared by chloroform-phenol extraction, treated with RNase-free DNase, and purified with Qiagen RNeasy MinElute columns. RNA quality was assessed by Bioanalyzer RNA integrity number quantification (Agilent Technologies). cDNA synthesis and amplification was performed with a SMART-seq V4 Ultra-Low Input RNA Kit (Clontech). Samples were diluted and mixed with SYBR green master mix before loading as technical triplicates for qPCR on a LightCycler 480 (Roche). DDCT values normalized to b-actin were used to assess relative gene expression between samples. The following validated primer pairs for murine CD22 were used: 5'-CCA CTC CTC AGG CCA GAA ACT-3' (forward) (SEQ ID NO. 5) and 5'-TGC CGA TGG TCT CTG GAC TG-3' (reverse) (SEQ ID NO. 6).

Immunohistochemistry/Immunocytochemistry

Mice were euthanized with 2.5% (v/v) Avertin and transcardially perfused with ice-cold HBSS containing glucose and HEPES. For immunocytochemistry, microglia were sorted by FACS and allowed to adhere onto poly-L-lysine coated glass coverslips prior to fixation in 4% paraformaldehyde (PFA) for 10 minutes at room temperature. For whole tissue immunohistochemistry, hemibrains were fixed in 4% PFA at 4° C. overnight before preservation in 30% sucrose in PBS. Hemibrains were sectioned into 40 μm coronal slices on a microtome and stored in cryoprotective solution at −20° C. Free-floating sections were permeabilized, blocked, and stained overnight at 4° C. with the following primary antibodies at the designated concentrations: goat polyclonal (1:500, Abcam), rat monoclonal anti-CD68 (1:600, BioRad), goat polyclonal anti-CD22 (1:40, R&D). Sections were washed, stained with Alexa Fluor-conjugated secondary antibodies (1:250), mounted and set under a coverslip before imaging on a confocal laser-scanning microscope (Zeiss LSM880).

pHrodo-Labeled A-Beta Preparation

A-beta oligomers were prepared as previously described (Stine W. B. et al. Biological Microarrays, A. Khademhosseini, K.-Y. Suh, and M. Zourob, eds. (Totowa, N. J.: Humana Press), 2010:13-32). Aβ(1-42) was treated with hexafluoroisopropanol (HFIP) to remove pre-existing aggregates and obtain solubilized monomeric peptide. Next, oligomers were assembled by diluting HFIP-treated monomers in ice-cold PBS overnight. To label A-beta, oligomers were incubated with pHrodo Red STP ester at RT for 30 minutes. Unconjugated dye was removed by size exclusion using Micro Spin Bio 6-P gel columns. pHrodo-conjugated A-beta oligomers were used immediately for phagocytosis assays at a concentration of 50 nM.

Western Blots

Cell lysates were prepared by incubating in cell pellets RIPA (150 mM NaCl, 1% Triton X-100, 0.5% Sodium Deoxycholate, 0.1% Sodium dodecyl sulfate, 50 mM Tris, pH 8.0) in the presence of a protease and phosphatase inhibitor (Roche). Protein concentrations were determined using a Bradford assay, and 10 ug of protein was resolved in SDS-PAGE. Blotting was performed using the following antibodies: pSHP-1 (Cell Signaling, clone D1185), a-tubulin (Abcam, clone Y69), SHP-1 (Cell Signaling, clone C14H6). Images were taken using a Licor Odyssey CLx imager.

REFERENCES

1. Arandjelovic, S., and Ravichandran, K. S. (2015). Phagocytosis of apoptotic cells in homeostasis. Nat Immunol 16, 907-917.
2. Aguzzi, A., Barres, B. A., and Bennett, M. L. (2013). Microglia: scapegoat, saboteur, or something else? Science 339, 156-161.
3. Ransohoff, R. M., and El Khoury, J. (2015). Microglia in Health and Disease. Cold Spring Harb Prospect Biol 8, a020560-16.
4. Aprahamian, T., Takemura, Y., Goukassian, D., and Walsh, K. (2008). Ageing is associated with diminished apoptotic cell clearance in vivo. Clinical & Experimental Immunology 152, 448-455.
5. Linehan, E., Dombrowski, Y., Snoddy, R., Fallon, P. G., Kissenpfennig, A., and Fitzgerald, D. C. (2014). Aging impairs peritoneal but not bone marrow-derived macrophage phagocytosis. Aging Cell 13, 699-708.
6. Lui, H., Zhang, J., Makinson, S. R., Cahill, M. K., Kelley, K. W., Huang, H.-Y., Shang, Y., Oldham, M. C., Martens, L. H., Gao, F., et al. (2016). Progranulin Deficiency Promotes Circuit-Specific Synaptic Pruning by Microglia via Complement Activation. Cell 165, 921-935.
7. Salter, M. W., and Stevens, B. (2017). Microglia emerge as central players in brain disease. Nature Medicine 23, 1018-1027.
8. Kawas, C. H., Kim, R. C., Sonnen, J. A., Bullain, S. S., Trieu, T., and Corrada, M. M. (2015). Multiple pathologies are common and related to dementia in the oldest-old: The 90+ Study. Neurology 85, 535-542.
9. Vaughan, D. W. and Peters, A. (1974). Neuroglial cells in the cerebral cortex of rats from young adulthood to old age: an electron microscope study. J Neurocytol. 3, 405-429.
10. Tremblay, M.-È., Zettel, M. L., Ison, J. R., Allen, P. D., and Majewska, A. K. (2012). Effects of aging and sensory loss on glial cells in mouse visual and auditory cortices. Glia 60, 541-558.
11. Hefendehl, J. K., Neher, J. J., Sühs, R. B., Kohsaka, S., Skodras, A., and Jucker, M. (2013). Homeostatic and injury-induced microglia behavior in the aging brain. Aging Cell 13, 60-69.
12. Safaiyan, S., Kannaiyan, N., Snaidero, N., Brioschi, S., Biber, K., Yona, S., Edinger, A. L., Jung, S., Rossner, M. J., and Simons, M. (2016). Age-related myelin degradation burdens the clearance function of microglia during aging. Nature Neuroscience 19, 995-998.
13. Eggel, A., and Wyss-Coray, T. (2014). A revival of parabiosis in biomedical research. Swiss Med Wkly 1-9.
14. Villeda, S. A., Luo, J., Mosher, K. I., Zou, B., Britschgi, M., Bieri, G., Stan, T. M., Fainberg, N., Ding, Z., Eggel, A., et al. (2011). The ageing systemic milieu negatively regulates neurogenesis and cognitive function. Nature 477, 90-94.
15. Katsimpardi, L., Litterman, N. K., Schein, P. A., Miller, C. M., Loffredo, F. S., Wojtkiewicz, G. R., Chen, J. W., Lee, R. T., Wagers, A. J., and Rubin, L. L. (2014). Vascular and Neurogenic Rejuvenation of the Aging Mouse Brain by Young Systemic Factors. Science 344, 630-634.
16. Villeda, S., Plamback, K. E., Middeldorp, J., Castellano, J. M., Mosher, K. I., Luo, J., Smith, L. K., Bieri, G., Lin, K., Berdnik, D., Wabl, R., et al. (2014). Young blood reverses age-related impairments in cognitive function and synaptic plasticity in mice. Nature Medicine 20, 659-663.
17. Castellano, J. M., Mosher, K. I., Abbey, R. J., McBride, A. A., James, M. L., Berdnik, D., Shen, J. C., Zou, B., Xie, X. S., Tingle, M., Hinkson, I. V., Angst, M. S., and Wyss-Coray T. (2017) Human umbilical cord plasma proteins revitalize hippocampal function in aged mice. Nature 544, 488-492.
18. Castellano, J. M., Kirby, E. D., and Wyss-Coray, T. (2015). Blood-borne revitalization of the aged brain. JAMA Neurol 72, 1191-1194.
19. Koike-Yusa, H., Li, Y., Tan, E. P., Velasco-Herrera Mdel, C., and Yusa, K. (2014). Genome-wide recessive genetic screening in mammalian cells with a lentiviral CRISPR-guide RNA library. Nat Biotechnol 32, 267-273.
20. Shalem, O., Sanjana, N. E., Hartenian, E., Shi, X., Scott, D. A., Mikkelson, T., Heckl, D., Ebert, B. L., Root, D. E., Doench, J. G., et al. (2014). Genome-scale CRISPR-Cas9 knockout screening in human cells. Science 343, 84-87.
21. Shalem, O., Sanjana, N. E. and Zhang, F (2015). High-throughput functional genomics using CRISPR-Cas9 Nature Reviews Genetics 16, 299-311.
22. Wang, T., Wei, J. J., Sabatini, D. M., and Lander, E. S. (2014). Genetic screens in human cells using the CRISPR-Cas9 system. Science 343, 80-84.
23. Zhou, Y., Zhu, S., Cai, C., Yuan, P., Li, C., Huang, Y., and Wei, W. (2014). Highthroughput screening of a CRISPR/Cas9 library for functional genomics in human cells. Nature 509, 487-491.
24. Deans, R. M., Morgens, D. W., Okesli, A., Pillay, S., Horlbeck, M. A., Kampmann, M., Gilbert, L. A., Li, A., Mateo, R., Smith, M., Glenn, J. S., Carette, J. E., Khosla, C., and Bassik, M. C. (2016). Parallel shRNA and CRISPR-Cas9 screens enable antiviral drug target identification. Nature Chemical Biology 12, 361-366.
25. Morgens, D. W., Wainberg, M., Boyle, E. A., Ursu, O., Araya, C. L., Tsui, C. K., Haney, M. S., Hess, G. T., Han, K., Jeng, E. E., et al. (2017). Genome-scale measurement of offtarget activity using Cas9 toxicity in high-throughput screens. Nature Communications 8, 1-8.

26. Blasi, E., Barluzzi, R., Bocchini, V., Mazzolla, R., and Bistoni, F. (1990). Immortalization of murine microglial cells by a v-raf/v-myc carrying retrovirus. Journal of Neuroimmunology 27, 229-237.
27. Morgens, D. W., Deans, R. M., Li, A., and Bassik, M. C. (2016). Systematic comparison of CRISPR/Cas9 and RNAi screens for essential genes. Nature Biotechnology 34, 634-636.
28. Sellmeier, M., Weinhold, B., and Münster-Kühnel, A. (2015). CMP-Sialic Acid Synthetase: The Point of Constriction in the Sialylation Pathway. In SialoGlyco Chemistry and Biology I: Biosynthesis, Structural Diversity and Sialoglycopathologies, R. Gerardy-Schahn, P. Delannoy, and M. von Itzstein, eds. (Berlin, Heidelberg: Springer Berlin Heidelberg), pp. 139-167.
29. Macauley, M. S., Crocker, P. R., and Paulson, J. C. (2014). Siglec-mediated regulation of immune cell function in disease. Nat Rev Immunol 14, 653-666.
30. Seyrantepe, V., Iannello, A., Liang, F., Kanshin, E., Jayanth, P., Samarani, S., Szewczuk, M. R., Ahmad, A., and Pshezhetsky, A. V. (2010). Regulation of phagocytosis in macrophages by neuraminidase 1. J. Biol. Chem. 285, 206-215.
31. Claude, J., Linnartz-Gerlach, B., Kudin, A. P., Kunz, W. S., and Neumann, H. (2013). Microglial CD33-Related Siglec-E Inhibits Neurotoxicity by Preventing the Phagocytosis-Associated Oxidative Burst. Journal of Neuroscience 33, 18270-18276.
32. Nomura, K., Vilalta, A., Allendorf, D. H., Hornik, T. C., and Brown, G. C. (2017). Activated Microglia Desialylate and Phagocytose Cells via Neuraminidase, Galectin-3, and Mer Tyrosine Kinase. J. Immunol. 198, 4792-4801.
33. Rillahan, C. D., Antonopoulos, A., Lefort, C.T., Sonon, R., Azadi, P., Ley, K., Dell, A., Haslam, S. M., and Paulson, J. C. (2012). Global metabolic inhibitors of sialyl- and fucosyltransferases remodel the glycome. Nat Chem Biol 8, 662-669.
34. Varki A., Schnaar R. L., Schauer R. Sialic Acids and Other Nonulosonic Acids. 2017. In: Varki A, Cummings R. D., Esko J. D., et al., editors. Essentials of Glycobiology [Internet]. 3rd edition. Cold Spring Harbor (N. Y.): Cold Spring Harbor Laboratory Press; 2015-2017. Chapter 15.
35. Hudak, J. E., Canham, S. M., and Bertozzi, C. R. (2013). Glycocalyx engineering reveals a Siglec-based mechanism for NK cell immunoevasion. Nat Chem Biol 10, 69-75.
36. Stansley, B., Post, J., and Hensley, K. (2012). A comparative review of cell culture systems for the study of microglial biology in Alzheimer's disease. J. Neuroinflammation 9, 115.
37. Bohlen, C. J., Bennett, F. C., Tucker, A. F., Collins, H. Y., Mulinyawe, S. B., and Barres, B. A. (2017). Diverse Requirements for Microglial Survival, Specification, and Function Revealed by Defined-Medium Cultures. Neuron 94, 759-773.
38. Varki A., Schnaar R. L., Crocker P. R. I-Type Lectins. 2017. In: Varki A., Cummings R. D., Esko J. D., et al., editors. Essentials of Glycobiology [Internet]. 3rd edition. Cold Spring Harbor (N. Y.): Cold Spring Harbor Laboratory Press; 2015-2017. Chapter 35.
39. Hickman, S. E., Kingery, N. D., Ohsumi, T. K., Borowsky, M. L., Wang, L., Means, T. K., and El Khoury, J. (2013). The microglial sensome revealed by direct RNA sequencing. Nature neuroscience 16, 1896-1905.
40. Galatro, T. F., Holtman, I. R., Lerario, A. M., Vainchtein, I.D., Brouwer, N., Sola, P. R., Veras, M. M., Pereira, T. F., Leite, R. E. P., Möller, T., et al. (2017). Transcriptomic analysis of purified human cortical microglia reveals age-associated changes. Nat Neurosci 20, 1162-1171.
41. Müller, J., and Nitschke, L. (2014). The role of CD22 and Siglec-G in B-cell tolerance and autoimmune disease. Nature Reviews Rheumatology 10, 422-428.
42. Müller, J., Obermeier, I., Wöhner, M., Brandl, C., Mrotzek, S., Angermüller, S., . . . Nitschke, L. (2013). CD22 ligand-binding and signaling domains reciprocally regulate Bcell Ca2+ signaling. Proc Natl Acad Sci USA 110, 12402-12407.
43. Mott, R. T., Ait-Ghezala, G., Town, T., Mori, T., Vendrame, M., Zeng, J., Ehrhart, J., Mullan, M., and Tan, J. (2004). Neuronal expression of CD22: Novel mechanism for inhibiting microglial proinflammatory cytokine production. Glia 46, 369-379.
44. Wong, A. M., Patel, N. V., Patel, N. K., Wei, M., Morgan, T. E., de Beer, M. C., de Villiers, W. J. S., and Finch, C. E. (2005). Macrosialin increases during normal brain aging are attenuated by caloric restriction. Neuroscience Letters 390, 76-80.
45. Hart, A. D., Wyttenbach, A., Perry, V. H., and Teeling, J. L. (2012). Age related changes in microglial phenotype vary between CNS regions: Grey versus white matter differences. Brain Behavior and Immunity 26, 754-765.
46. Miyagi, T. and Yamaguchi. K. (2012). Mammalian sialidases: Physiological and pathological roles in cellular functions. Glycobiology 22, 880-896.
47. Larocca, J. N., and Norton, W. T. (2007). Isolation of myelin. Curr. Protoc. Cell Biol. Chapter 3, 25.
48. Xiao, H., Woods, E. C., Vukojicic, P., and Bertozzi, C. R. (2016). Precision glycocalyx editing as a strategy for cancer immunotherapy. Proc Natl Acad Sci USA 113, 10304-10309.
49. Bennett, M. L., Bennett, F. C., Liddelow, S. A., Ajami, B., Zamanian, J. L., Fernhoff, N. B., Mulinyawe, S. B., Bohlen, C. J., Adil, A., Tucker, A., Weissman, I. L., Chang, E. F., Li, G., Grant, G. A., Hayden Gephart, M. G. and Barres, B. A. (2016). New tools for studying microglia in the mouse and human CNS. Proc Natl Acad Sci USA 113, E1738-46.
50. Sierra, A., Gottfried-Blackmore, A. C., McEwen, B. S., and Bulloch, K. (2007). Microglia derived from aging mice exhibit an altered inflammatory profile. Glia 55, 412-424.
51. Xu, H., Chen, M., Manivannan, A., Lois, N., and Forrester, J. V. (2008). Age dependent accumulation of lipofuscin in perivascular and subretinal microglia in experimental mice. Aging Cell 7, 58-68.

EXPERIMENTAL EXAMPLES

References cited in the Experimental Examples are provided as the final section of each Experimental Example.

Example 1—CD22 Blockade Restores Homeostatic Microglial Phagocytosis in the Aging Brain Microglia maintain homeostasis in the central nervous system (CNS) through multiple modalities including phagocytic clearance of pathogens, apoptotic cells, and debris[1-4]. This function deteriorates during normal aging and neurodegenerative disease, concomitant with cognitive decline[5]. Targeted restoration of microglial phagocytosis in the aging brain is an attractive therapeutic strategy. We combined CRISPR-Cas9 knockout screens with RNA-sequencing (RNA-seq) analysis to identify genetic modifiers of microglial phagocytosis that are differentially expressed with age. The screens identified CD22, a sialic acid-binding immunoglobulin-like lectin (Siglec) expressed on B-cells, as a negative regulator of phagocytosis that is upregulated and exclusively expressed on aged microglia in the central nervous system (CNS). CD22 mediates the anti-phagocytic effect of sialic acid, and inhibition of CD22 promotes phagocytosis of myelin debris, amyloid beta (Aβ) oligomers, and α-synuclein fibrils in vivo. Long-term CNS-delivery of a CD22 function-blocking antibody reprograms microglia to a homeostatic transcriptional state and improves cognitive function in aged mice.

Microglia are among the longest-lived mammalian cell types, residing in the brains of mice for years[6] and in humans for decades[7]. During this period, microglia peruse the brain parenchyma with ramified processes to sense perturbations[8,9], and respond with specialized compensatory functions. One of the core microglial functions necessary for homeostasis in the CNS is the recognition, engulfment, and degradation of large extracellular material via phagocytosis[2]. While microglial phagocytosis is crucial throughout an organism's lifespan, the targets of engulfment change depending on age. For example, complement-mediated synaptic pruning is necessary for postnatal circuit refinement[10-12], yet inappropriate activation of this pathway in neurodegenerative diseases contributes to deleterious synapse elimination[13-16]. With normal aging and age-related disease, microglia encounter unique perturbations in the CNS including abundant myelin debris[17] and pathological extracellular protein aggregates. A complex system of extrinsic and intrinsic inhibitory molecules normally regulates microglial phagocytosis to support efficient elimination of these targets without damaging surrounding tissue[18]. However, microglia in the aged brain are hypo-motile[19], burdened with lysosomal cargo[17,20,21] and chronically express pro-inflammatory signaling molecules indicative of impaired homeostatic function[23].

Figure 30:
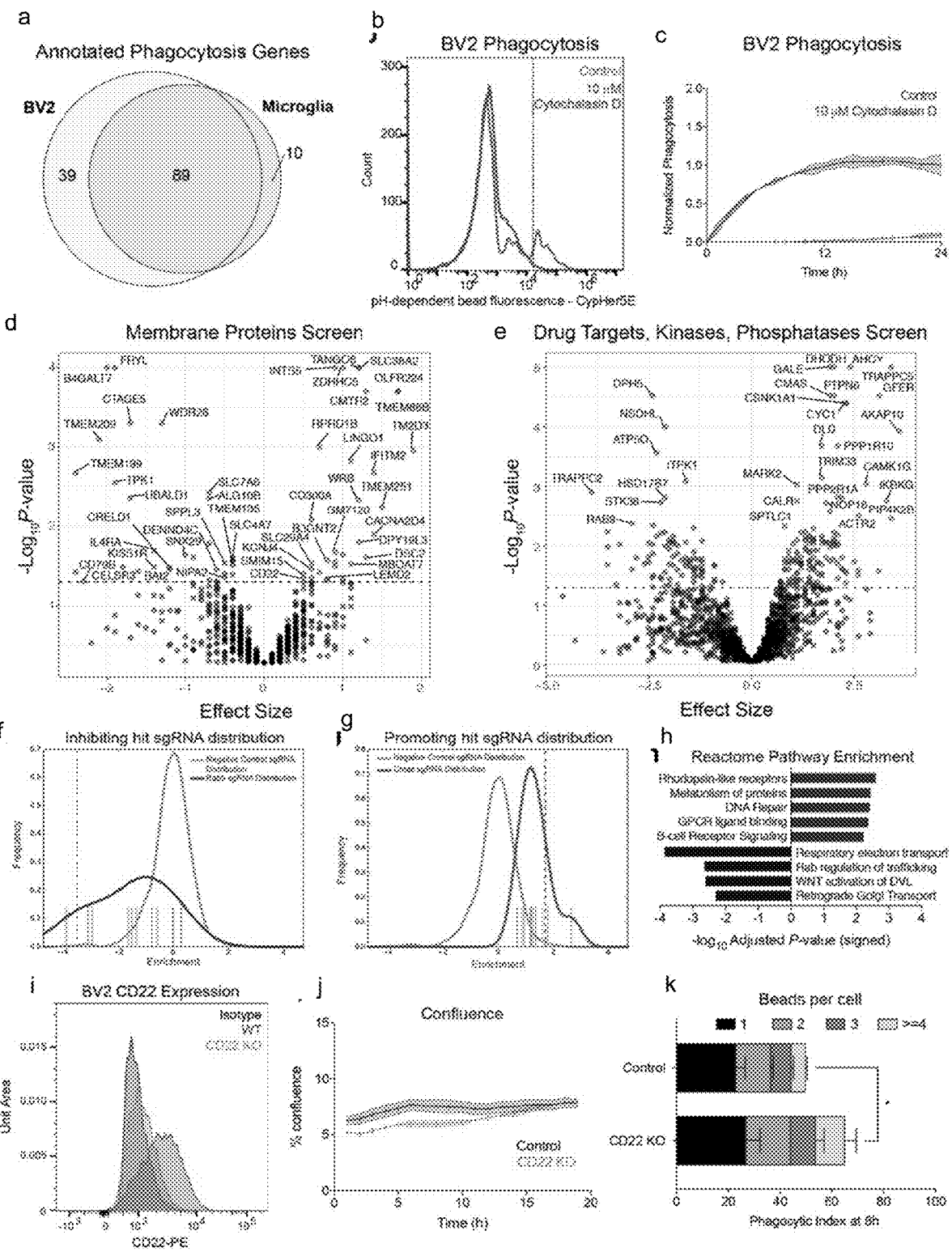
FIG. 30 shows a screen for genetic modifiers of phagocytosis. (a), Venn diagram showing the intersection and disjunction of 138 annotated phagocytosis genes from the mouse genome informatics database (www.informatics.jax.org/go/term/G0:0006909) expressed (FPKM>5) by BV2 cells (GSE103156) and primary microglia. (b), Histogram showing phagocytosis of pH-sensitive fluorescent beads by BV2 cells treated with vehicle (gray) or the actin-polymerization inhibitor, cytochalasin D (red). Dashed line represents gate set for FACS sorting of phagocytic and non-phagocytic cells. (c), Phagocytosis of pH-sensitive fluorescent beads by BV2 cells treated with vehicle (gray) or cytochalasin D (red), assessed by time-lapse microscopy. (n=3, ****P<0.00005, ANOVA with repeated measures; shading, S.E.M.). (d), Volcano plot showing significant hits from CRISPR-Cas9 screen targeting 954 membrane proteins in BV2 cells. Knockouts that promote phagocytosis (red) have a positive effect size and knockouts that inhibit phagocytosis (blue) have a negative effect size (dotted line, P=0.05). (e), Volcano plot showing significant hits from CRISPR-Cas9 screen targeting 2,015 drug targets, kinases, and phosphatases in BV2 cells. Knockouts that promote phagocytosis (red) have a positive effect size and knockouts that inhibit phagocytosis (blue) have a negative effect size (dotted line, P=0.05). (f), Distributions of negative control sgRNAs (gray) and Rab9-targeting sgRNAs (blue). Positive values indicate enrichment in the phagocytic fraction, and negative values indicate enrichment in the non-phagocytic fraction. (g), Distributions of negative control sgRNAs (gray) and CMAS-targeting sgRNAs (red). Positive values indicate enrichment in the phagocytic fraction, and negative values indicate enrichment in the non-phagocytic fraction. (h), Statistical overrepresentation test showing enrichment of Reactome pathway annotations within phagocytosis-promoting (red) and -inhibiting (blue) hits. (i), Histogram showing CD22 expression in WT (blue), CD22 KO (green), and isotype control stained (black) BV2 cells assessed by flow cytometry. (j), Percent confluence of control (gray) and CD22 KO (green) BV2 cells during time-lapse microscopy phagocytosis assays (n=3, N.S. not significant). (k), Number of beads ingested per cell were calculated in control and CD22 KO BV2 cells after 8 hours of phagocytosis. While CD22 KO cells display enhanced phagocytosis at a population level (*P<0.05, t-test), we observed no significant differences in the number of beads ingested per cell (2-way ANOVA).
Figure 31:
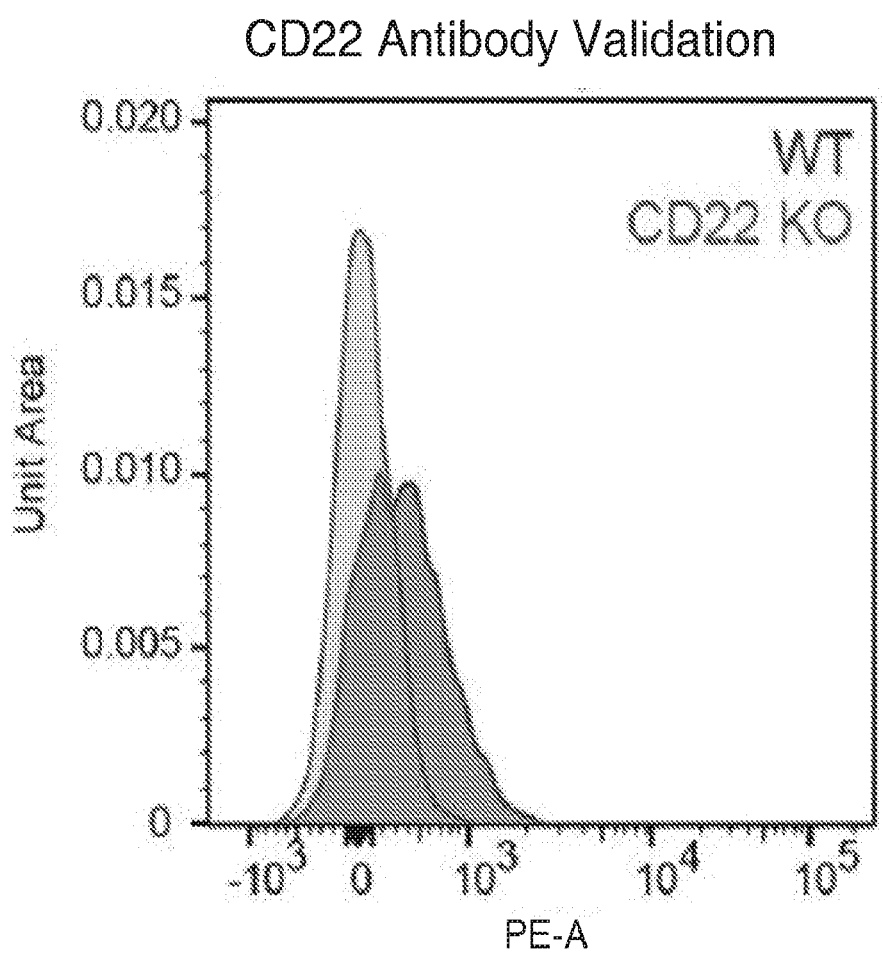
FIG. 31 shows immunophenotyping of sialic acid-related molecule expression on young and aged microglia. Microglia from WT or CD22−/− aged mice were stained with the particular anti-CD22 clone used for immunophenotyping. CD22−/− microglia show no staining relative to FMO.

Combined CRISPR-Cas9 Screens and RNA-Seq Analysis Identify a Genetic Modifier of Phagocytosis that is Differentially Expressed with Age Microglia undergo significant transcriptional changes with age[24-26]. We used CRISPR-Cas9 knockout screens[27-34], to identify genetic modifiers of phagocytosis in the microglia-derived cell line, BV2[35]. Given the cell number limitations[36] of culturing primary microglia[37], primary cell screens are not feasible. Although BV2 cells do not accurately recapitulate all features of microglia in vivo[38], the two cell types express similar phagocytic machinery (FIG. 30a). Therefore, genetic modifiers of phagocytosis in BV2 cells are suitable candidates for subsequent validation in vivo. In order to identify genes responsive to therapeutic intervention, we used libraries of single-guide RNAs (sgRNAs) targeting 954 genes coding for transmembrane proteins and 2,015 genes coding for known drug targets, kinases, and phosphatases, with 10 sgRNAs per gene along with ~3,000 negative control sgRNAs.

We infected Cas9-expressing BV2 cells with a pool of sgRNAs to obtain a population of single-knockout cells for every gene targeted in the sgRNA library (FIG. 1a). To ensure adequate representation of each knockout, we maintained the cells at 1,000× coverage throughout the screen (~1,000 cells containing each sgRNA), a level previously shown to reduce false negative rate[28]. After selecting for stable sgRNA expression, we incubated the cells with latex particles labeled with a pH-sensitive fluorescent dye to monitor particle uptake and lysosomal trafficking. Next, we sorted phagocytic and non-phagocytic populations by fluorescence-activated cell sorting (FACS) (FIGS. 30b-c), sequenced genomic DNA from each population, and analyzed the sgRNA distributions between populations. The effect size and P-value of each gene knockout were estimated using casTLE[39], wherein sgRNAs enriched in the phagocytic population are represented by a positive effect sign and sgRNAs enriched in the non-phagocytic population are represented by a negative effect sign. The screens identified 286 significant hits, including multiple known negative and positive regulators of phagocytosis (FIGS. 30d-h).

Figure 26:
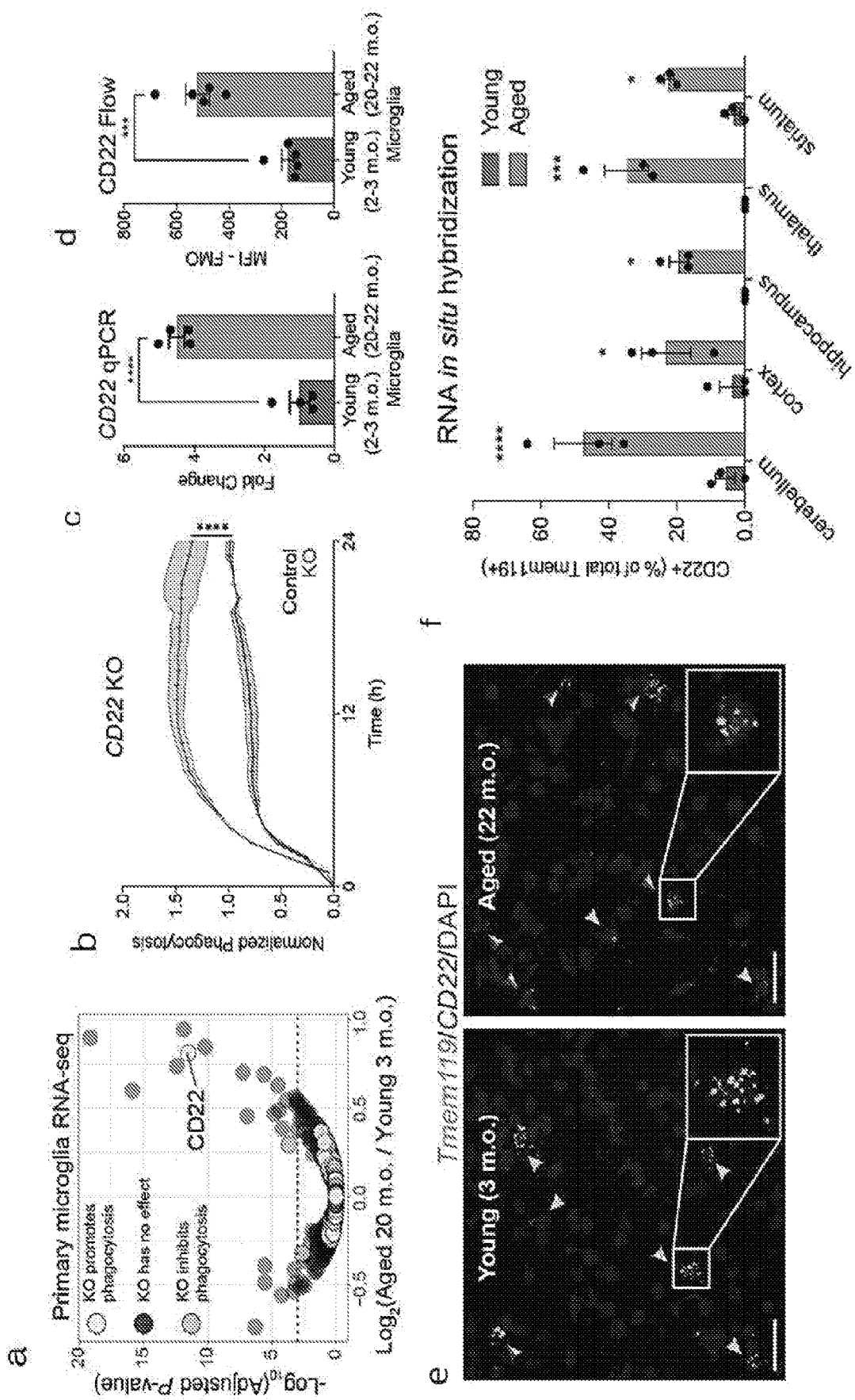
FIG. 26 shows that combined CRISPR-Cas9 screens and RNA-seq analyses identify CD22 as a target for restoration of microglial phagocytosis in the aging brain. (a), Volcano plot of RNA-seq analysis showing differentially expressed genes between aged (20 m.o., n=8) and young (3 m.o., n=8) primary microglia overlaid with significant hits from CRISPR-Cas9 screen of BV2 cells. Yellow dots represent hits that promote phagocytosis, blue dots represent hits that inhibit phagocytosis, and gray dots are knockouts that showed no effect. Dashed line represents 0.1% false discovery rate (FDR). (b), Phagocytosis of pH-sensitive fluorescent beads monitored by time-lapse microscopy over 24 hours, imaged every hour. Control BV2 cells were infected with a "safe-targeting" sgRNA and KO BV2 cells were infected with a sgRNA targeting CD22 (n=3, **P<0.00005, ANOVA with repeated measures; shading, S.E.M.). (c), qPCR of CD22 expression in acutely isolated primary microglia from young (2-3 m.o.) and aged (20-22 m.o.) mice, normalized to a housekeeping gene (β-actin); data represent fold change relative to young microglia (n=4, P<0.00005, t-test). (d), Quantification of CD22 mean fluorescence intensity (MFI)-fluorescence minus one (FMO) background intensity of young (2-3 m.o.) and aged (20-22 m.o.) microglia assessed by flow cytometry (n=5, *P<0.0005, t-test). (e), Representative images of young and aged cerebella probed for Tmem119 (green), CD22 (red), and stained with DAPI to show nuclei. Green arrows indicate Tmem119+ microglia, and half-green, half-red arrows indicate Tmem119+CD22+ microglia. Scale bar=30 microns. (f), Quantification of RNA in situ hybridization assessing the percentage of Tmem119+ microglia that co-express CD22 in multiple brain regions of young (3 m.o., brown) and aged (22 m.o., gray) mice (n=3, *P<0.05, *P<0.0005, **P<0.00005, 2-way ANOVA with Sidak correction).

To identify genes that contribute to the decreased phagocytic capacity of aged microglia, we performed RNA-seq on purified hippocampal microglia from young (3-month-old) and aged (20-month-old) mice and compared hits from our BV2 screen to genes differentially expressed with age in primary microglia. We focused on the hippocampus due to its selective sensitivity to aging and functional importance in learning and memory[40-43]. Within the subset of genes targeted by our CRISPR-Cas9 screen, we tested for age-upregulated microglial genes whose corresponding BV2 knockout promotes phagocytosis, or age-downregulated microglial genes whose corresponding BV2 knockout inhibits phagocytosis. These genes might have a functional role in age-related microglial impairment, either through increased inhibition or decreased activation of phagocytosis. CD22, a Siglec typically expressed on B-cells[44,45] fit these criteria (FIG. 26a). CD22 is significantly upregulated in aged microglia, corroborating previously published datasets[24,25,26] and that its corresponding BV2 knockout promotes phagocytosis. We confirmed this effect in orthogonal time-lapse microscopy validation experiments (FIG. 26b, FIGS. 30j,k). CD22 negatively regulates B-cell receptor (BCR) signaling[46], and modulates leukocyte phagocytosis in fish species[47,48].

Other Siglecs regulate microglial phagocytosis in diverse contexts[49] including suppression of Aβ clearance by CD33 in Alzheimer's disease (AD)[50]. We analyzed the differential expression of all known mouse Siglecs between young and aged microglia, and found that CD22 is a Siglec that is significantly upregulated with age in the hippocampus. CD22 upregulation was confirmed by qPCR and by flow cytometry with a KO-validated antibody (FIG. 7, FIGS. 26c-d). Using a quantitative flow cytometry-based assay (FIG. 33a), we determined that aged microglia display approximately 300 CD22 molecules on their cell surface, three times the expression on young microglia and roughly equal to the number of molecules on immature B-cells (FIG. 33b). To test the regional distribution of microglial CD22 expression, we performed multiplexed fluorescence RNA in situ hybridization (RNAscope) on 5 brain regions from young and aged mice. We probed for CD22 as well as Tmem119, a microglia-specific marker[51]. Whereas CD22+ Tmem119+ microglia were nearly completely absent in the young brain, the aged brain contained a large proportion of these cells in every region assessed (FIGS. 26e-f). The thalamus and cerebellum contained especially high proportions of CD22+ microglia. We did not observe CD22+ puncta outside of Tmem119+ microglia, corroborating RNA-seq datasets showing that CD22 is expressed exclusively by microglia in the CNS (FIGS. 33c,e,f). The combined CRISPR-Cas9 screens and RNA-seq analysis show that CD22 is a potent negative regulator of phagocytosis in BV2 cells, and indicate that it is a potential target for restoration of phagocytosis in aged microglia.

CD22 Inhibition Promotes Microglial Phagocytosis In Vivo

Figure 27:
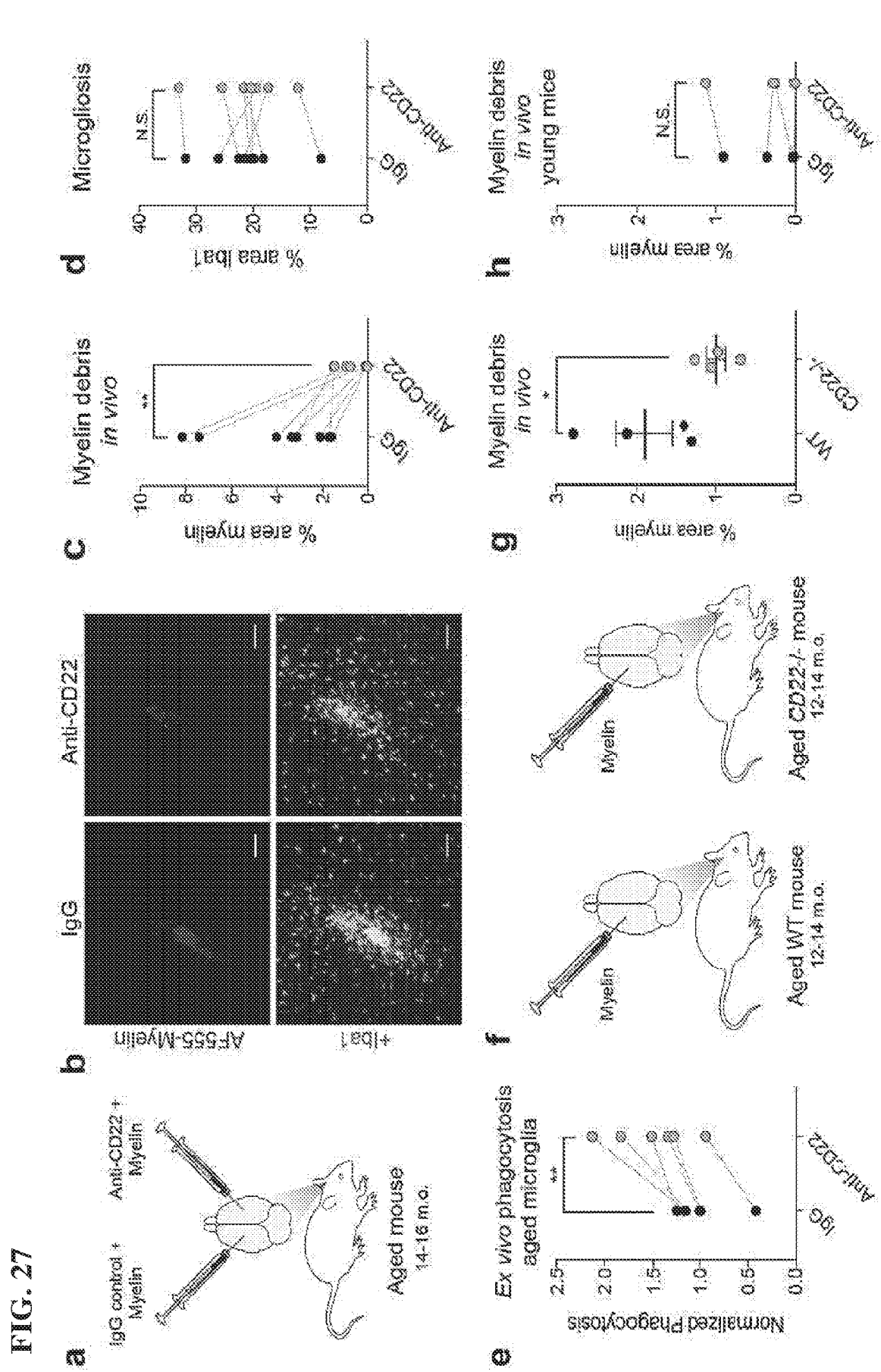
FIG. 27 shows that CD22 negatively regulates microglial phagocytosis in vivo. (a), Schematic diagram of in vivo phagocytosis assay in which myelin labeled with a fluorescent dye (AF555) was stereotactically co-injected with a CD22 blocking antibody or an IgG control antibody into the cortex on opposite hemispheres of the same aged (14-16 m.o.) mouse. (b) Representative images of myelin (red, top row) and myelin overlaid with the microglia marker Iba1 (green, bottom row) at the injection site (+/−2 mm lateral, 0 mm A-P, −1.5 mm D-V relative to bregma) of IgG (left) or anti-CD22 (right) treated hemispheres of the same aged brain. Scale bar=100 microns. (c), Clearance of myelin debris in the IgG (black) or anti-CD22 (green) treated hemispheres assessed 48 hours post-injection (n=8, **P<0.005, paired t-test). (d), Microgliosis, as assessed by % Iba1+ area at the injection site, was not altered by CD22 blockade (n=8, N.S. not significant). (e), Microglia were acutely isolated from the brains of aged mice, treated with an IgG isotype control antibody or anti-CD22, and incubated with pH-sensitive fluorescent latex beads. Microglia specific phagocytosis was measured using flow cytometry (n=6, *P<0.005, paired t-test). (f), Schematic diagram of in vivo phagocytosis assay in which myelin was stereotactically injected into the cortices of aged (12-14 m.o.) WT or CD22−/− mice. (g), Clearance of myelin debris in aged WT (black) or CD22−/−(green) mice was assessed 48 hours later (n=4, *P<0.05, t-test). (h), CD22 blockade does not affect myelin debris clearance in young mice (n=4, N.S. not significant). (i), Representative images of Aβ (red, left column) and Aβ overlaid with the microglia marker Iba1 (green, right column) at the injection site (+/−2 mm lateral, 0 mm A-P, −1.5 mm D-V relative to bregma) of IgG (top row) or anti-CD22 (bottom row) treated hemispheres of the same aged brain. Scale bar=100 microns. (j), Clearance of Aβ oligomers in the IgG (black) or anti-CD22 (green) treated hemispheres assessed 48 hours post-injection (n=8, **P<0.005, paired t-test). (k), Representative images of α-synuclein and Iba1 at the injection site in IgG and anti-CD22 treated mice. Scale bar=100 microns. (l), Clearance of α-synuclein fibrils in the IgG (black) or anti-CD22 (green) treated hemispheres assessed 48 hours post-injection (n=7, *P<0.05, paired t-test).
Figure 27:
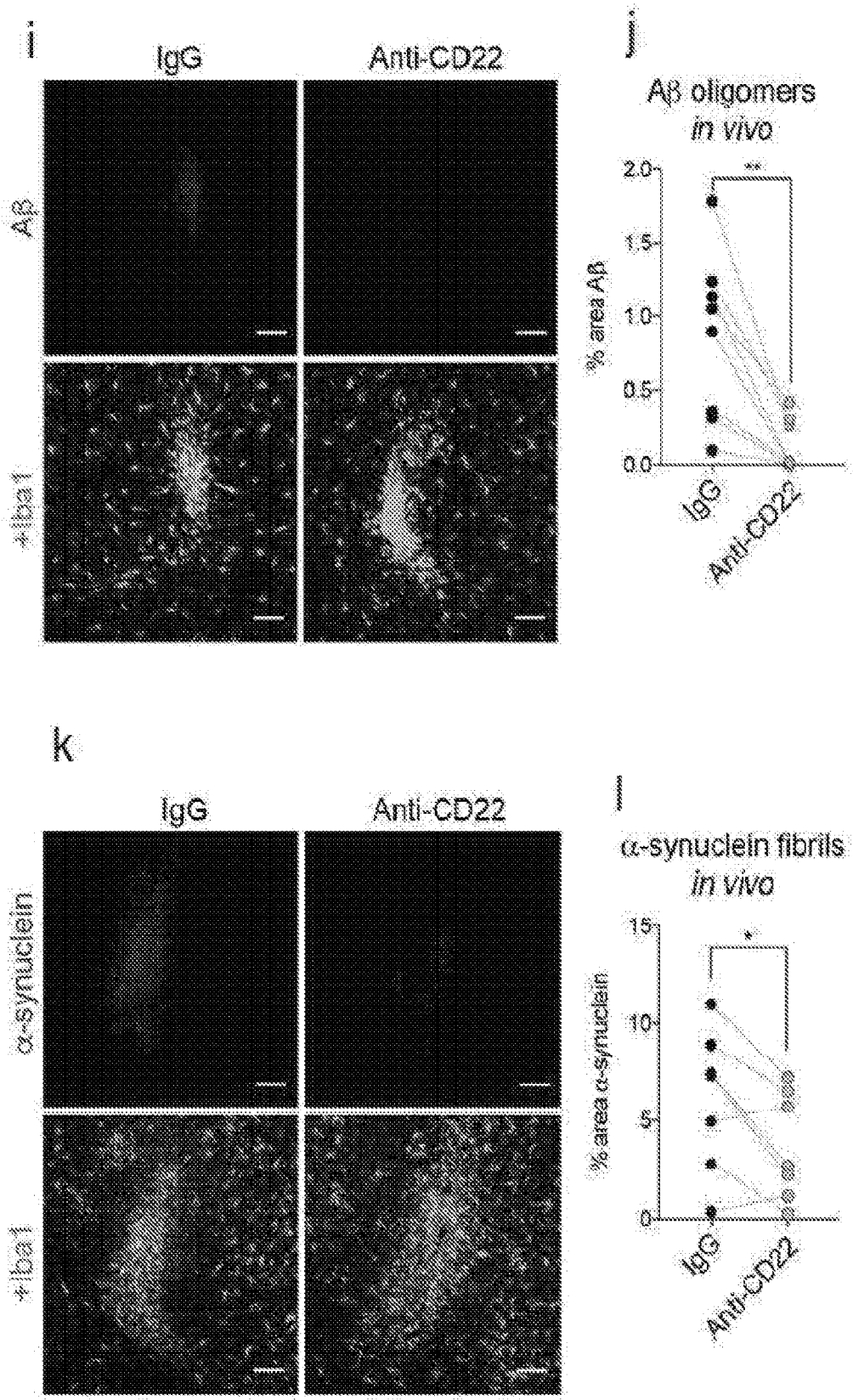

To test the function of CD22 upregulation in aged microglia, we performed an in vivo phagocytosis assay in which fluorescent myelin debris was stereotactically co-injected with a CD22 blocking antibody or an IgG isotype control antibody into opposite hemispheres of the same aged mouse (FIG. 27a). The assay comprises several advantages over in vitro primary cell or ex vivo organotypic slice culture methods. It more accurately simulates the native CNS environment, it is internally controlled for mouse-to-mouse variability, and it does not require serum to stimulate phagocytosis[37]. Myelin debris was injected as a physiological target because it accumulates in the aging brain and overwhelms the clearance function of microglia[17]. To confirm microglial engulfment and lysosomal trafficking, we labeled the myelin debris with a second pH-sensitive fluorescent dye and assessed overlap with the microglia marker, Iba1 (FIGS. 32a,b).

After 48 hours, we found that anti-CD22 treatment promotes clearance of myelin debris compared to IgG control (FIGS. 27b,c). Because microglia are the only cell type in the mouse CNS that express CD22[52] (FIG. 33c), the effect is microglia-specific. CD22 blockade did not influence the recruitment of microglia to the injection site relative to IgG (FIG. 27d) or a stab wound control (FIGS. 32c,e), and IgG itself did not influence myelin clearance (FIGS. 32c,d). Nearly all cells at the injection site were Tmem119+ regardless of treatment (FIGS. 32f,g), indicating that the pro-phagocytic effect of CD22 blockade is mediated by resident microglia and not infiltrating peripheral macrophages[51]. We confirmed the pro-phagocytic effect of anti-CD22 treatment in an orthogonal ex vivo phagocytosis assay using freshly isolated microglia from aged mice and pH-sensitive fluorescent latex particles (FIG. 27e). To rule out the possibility of Fc-dependent stimulation of phagocytosis and nonspecific binding interactions of the antibody, we injected labeled myelin debris into the brains of aged CD22−/− mice or age-matched wild-type mice (FIG. 27f). We observed comparable increases in myelin clearance with either genetic ablation or antibody-based blockade of CD22 (FIG. 27g). CD22 blockade (FIG. 27h) or genetic ablation (FIG. 32h) had no significant effect in the young mouse CNS, in which myelin debris is efficiently cleared at baseline and CD22 is minimally expressed.

Next, we evaluated the ability of anti-CD22 treatment to promote microglial phagocytosis of the characteristic pathological protein aggregates of AD or Parkinson's disease (PD). For AD, we co-injected oligomeric Aβ, a neurotoxic protein aggregate that accumulates in AD brain[53], along with anti-CD22 or an IgG control antibody into opposite hemispheres of the same aged mouse. Compared to control, anti-CD22 treatment promoted robust clearance of Aβ oligomers in vivo (FIG. 27i, FIGS. 32j,k). A larger percentage of residual Aβ in anti-CD22 treated hemispheres was contained in acidified lysosomes, as indicated by a pH-sensitive fluorescent dye (FIG. 32i), suggesting that CD22 blockade promotes degradation of engulfed debris. One of the pathological hallmarks of PD is the accumulation of α-synuclein as neuronal deposits (Lewy bodies) and extracellular fibrils. Accumulation of α-synuclein strongly correlates with cognitive decline and has been shown to alter the phagocytic capacity of microglia[54]. In an in vivo phagocytosis assay, we found that anti-CD22 treatment promotes the clearance of α-synuclein fibrils (FIGS. 27k,l, FIG. 32l). These data indicate that CD22 is a broad negative regulator of microglial phagocytosis in the aged CNS.

CD22 Mediates the Anti-Phagocytic Effect of Cell-Surface Sialic Acid

Figure 17:
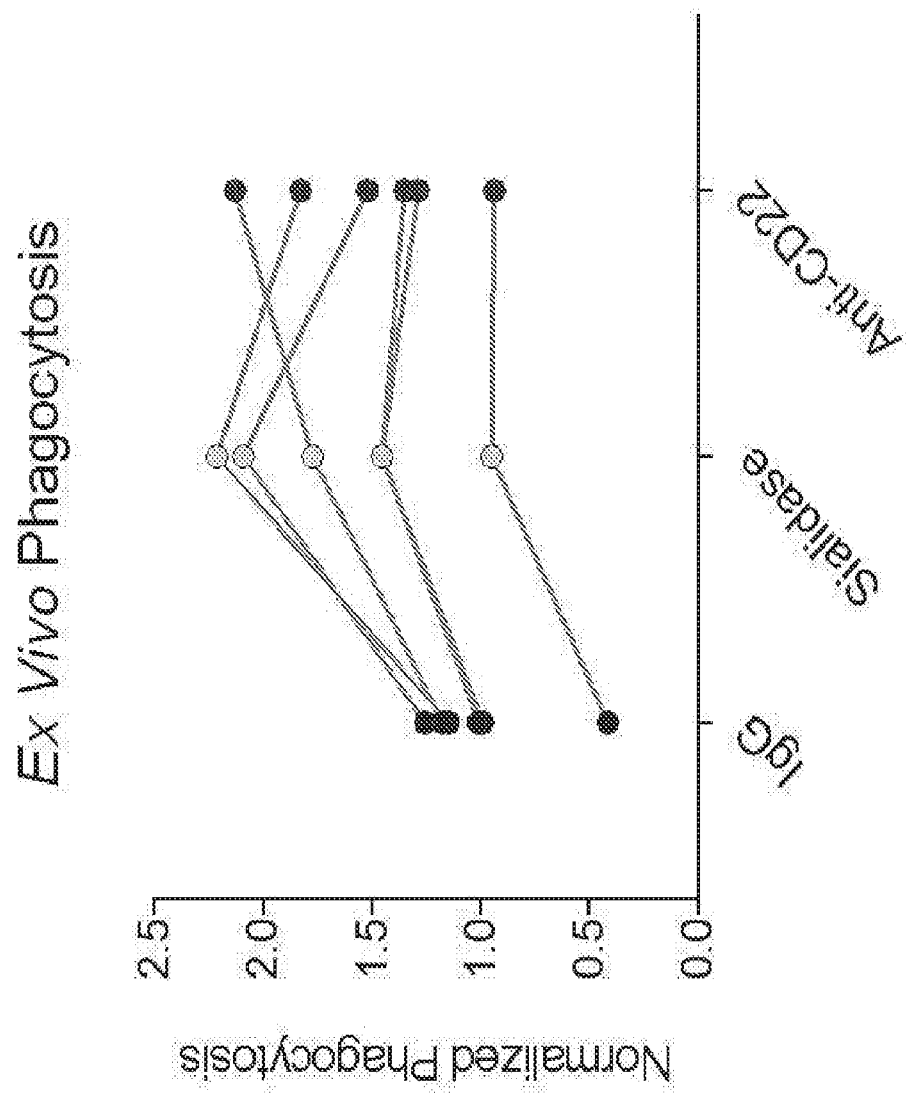
FIG. 17 shows that CD22 inhibits aged microglial phagocytosis. Phagocytosis of pH-dependent fluorescent particles by aged microglia treated with sialidase (yellow), a monoclonal mouse IgG1 anti-CD22 antibody (clone Cy34.1) (red), or no treatment (purple) for one hour prior to feeding. N=4 animals per group. Lines indicate paired samples harvested from the same mouse split into three separate tubes, and treated in parallel accordingly.
Figure 18:
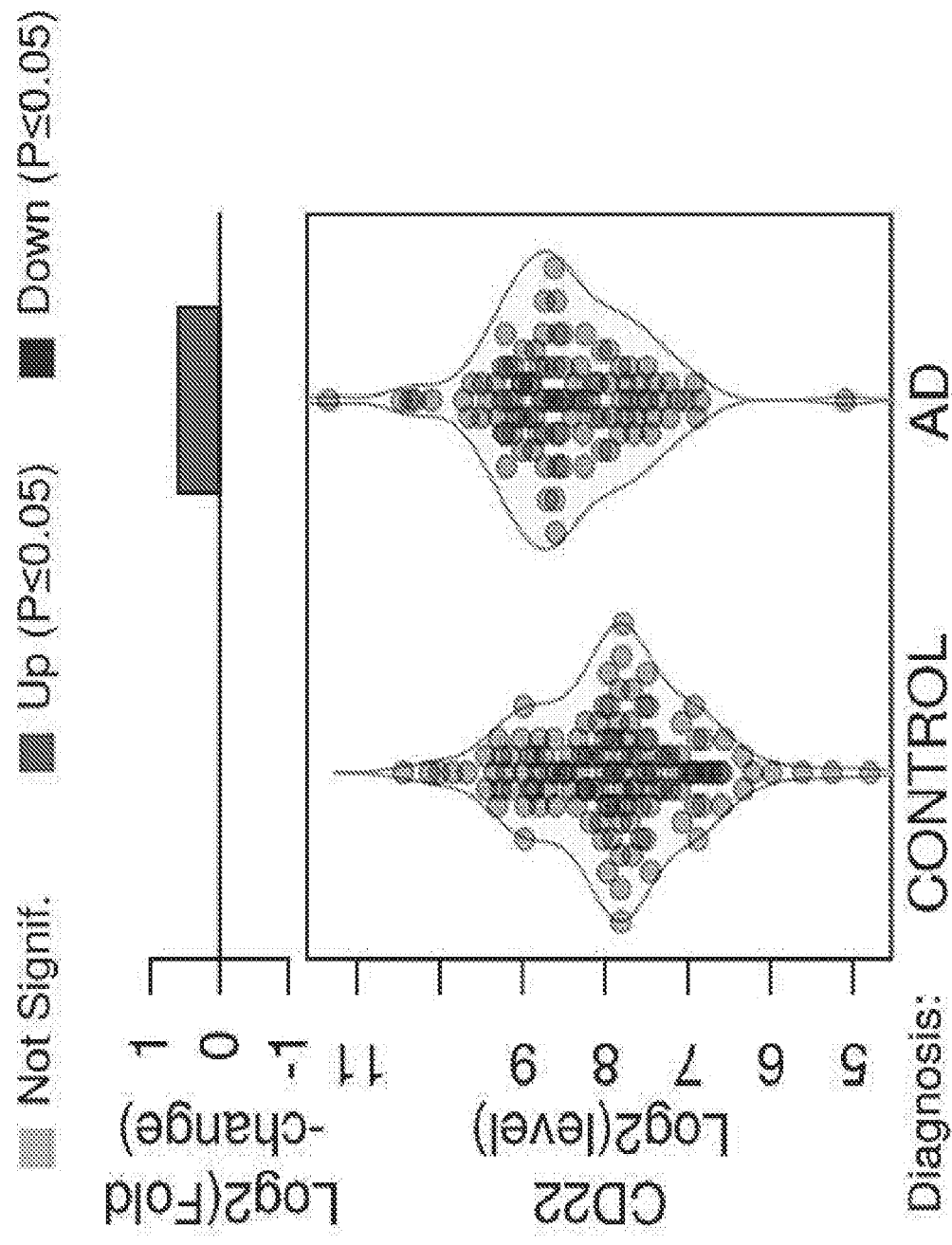
FIG. 18 shows that that CD22 is upregulated in the brains of Alzheimer's disease patients compared to age-matched, clinically-unimpaired controls in an analysis of published human microglia transcriptome datasets (Webster et al. Genetic control of human brain transcript expression in Alzheimer disease. *Am J Hum Genet* 2009 April; 84(4):445-58; and Friedman et al. Diverse brain myeloid expression profiles reveal distinct microglial activation states and aspects of Alzheimer's disease not evident in mouse models. *Cell Rep.* 2018 Jan. 16; 22(3):832-847.) These data indicate that targeting CD22 is applicable to multiple etiologies of late onset Alzheimer's disease (LOAD) irrespective of underlying genomic variation.
Figure 19:
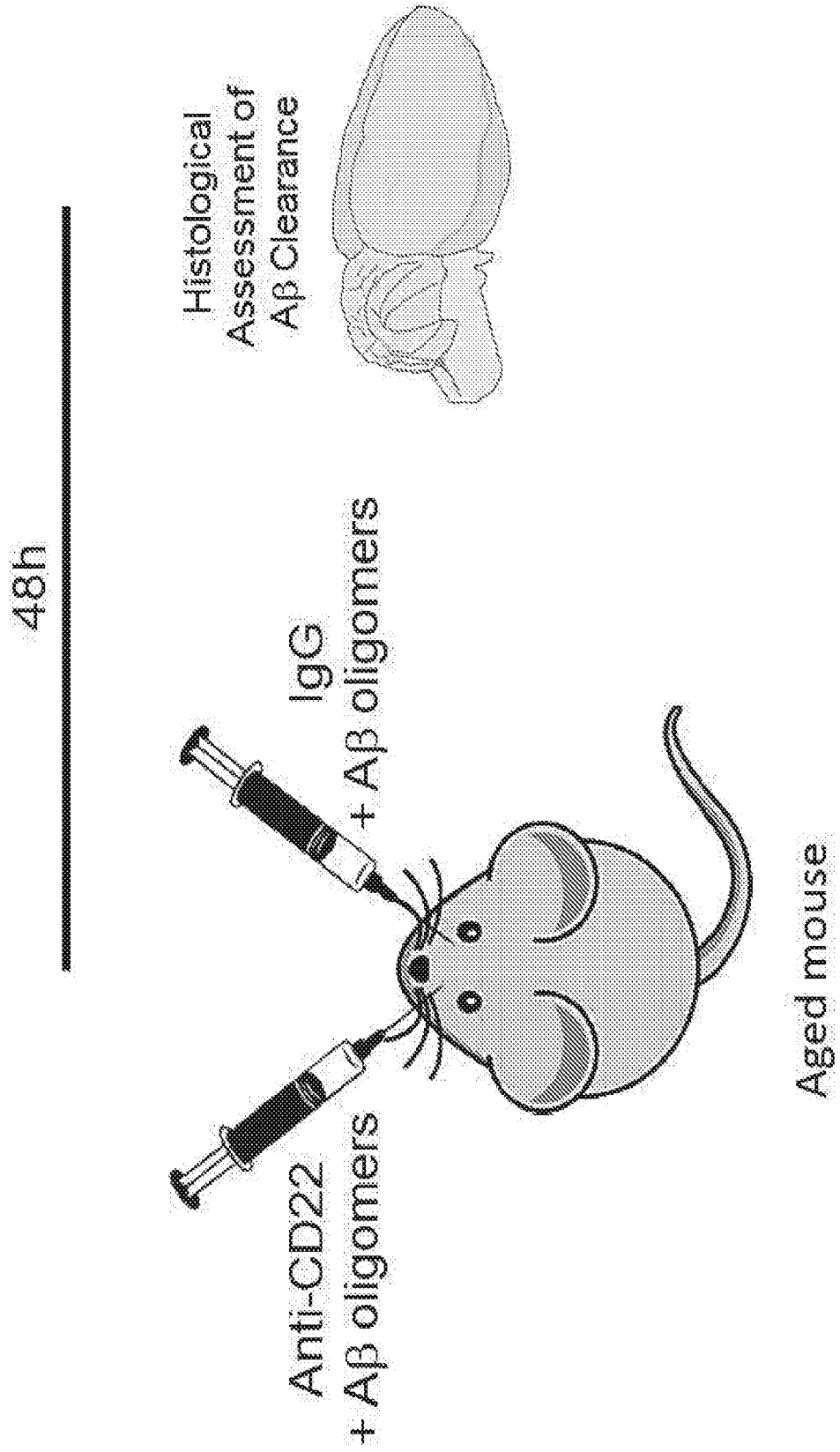
FIG. 19 shows a schematic diagram of an in vivo phagocytosis assay. Amyloid beta1-42 (Aβ) oligomers were prepared using the method of Stine et al. (Stine et al. *Methods Mol Biol.* 2011; 670: 13-32.) Hexafluoroisopropanol (HFIP) treated monomers were re-suspended in ice cold PBS and allowed to oligomerize overnight at 4 degrees C. Twenty-four hours later, oligomers were covalently labeled with a pH-sensitive dye (CypHer5E), and excess dye was removed with size exclusion columns. The labeled oligomers were then mixed with 1 ug of anti-CD22 (Cy34.1 clone) and/or IgG1 control antibody. Aged mice (13-16-month old) mice were anesthetized with isoflurane and placed in a stereotactic brain injection instrument. 1 uL of anti-CD22/oligomer mixture was cortically injected into one hemisphere, and 1 uL of IgG1 control/oligomer mixture was cortically injected into the other hemisphere. Forty-eight hours later, mice were perfused with paraformaldehyde, brains were fixed overnight, cryoprotected in sucrose, sectioned, and stained for Iba1 (microglia) and Aβ (total). Images were acquired on a ZEISS LSM880 confocal microscope. Percent areas of residual Aβ normalized to Iba1 percent areas were calculated. Compared to an isotype control antibody, treatment of aged microglia with anti-CD22 promoted phagocytosis of Aβ ex vivo. To confirm this effect in vivo, oligomeric Aβ together with anti-CD22 or an isotype control antibody was injected into the corticies of live age mice (a).
Figure 22:
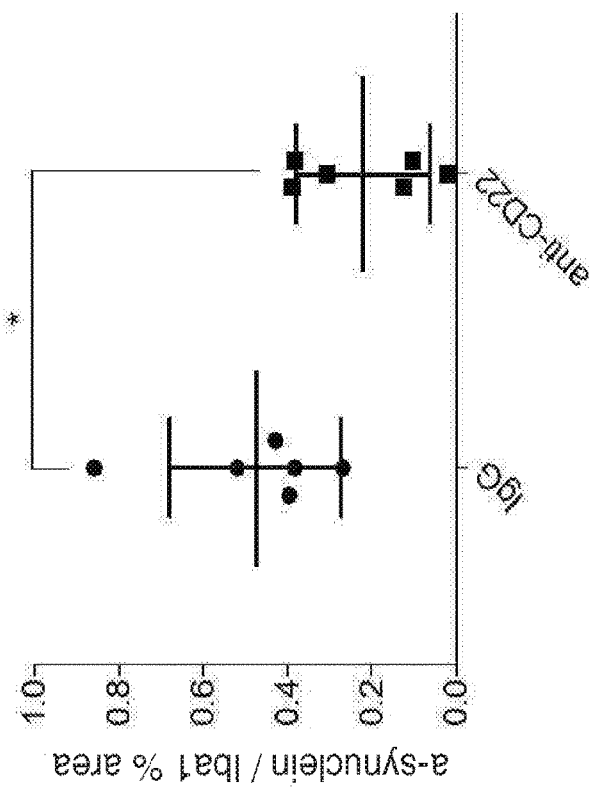
FIG. 22 shows that CD22 blockade promotes clearance and phagocytosis of α-synuclein fibrils when α-synuclein fibrils prepared by the method of Volpicelli-Daley et al. (Volpicelli-Daley et al. Addition of α-synuclein pre-formed fibrils to primary neuronal cultures to seed recruitment of endogenous α-synuclein to Lew body and Lewy neurite-like aggregates. *Nat Protoc.* 2014: 9(9); 2135-2146) are used instead of Aβ oligomers in the quantitative methods provided in the description of FIG. 19.
Figure 21:
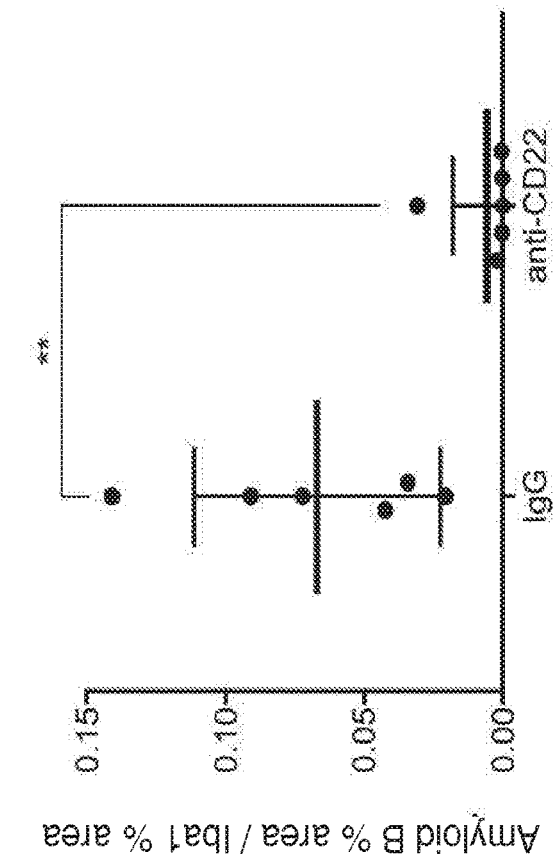
FIG. 21 shows that CD22 blockade promotes clearance and phagocytosis of Aβ using the quantitative methods provided in the description of FIG. 19. Forty-eight hours after injection, mice treated with anti-CD22 showed dramatically increased clearance of oligomeric Aβ compared to control mice. These data indicate that CD22 blockage promotes phagocytosis of neurotoxic Aβ.
Figure 23:
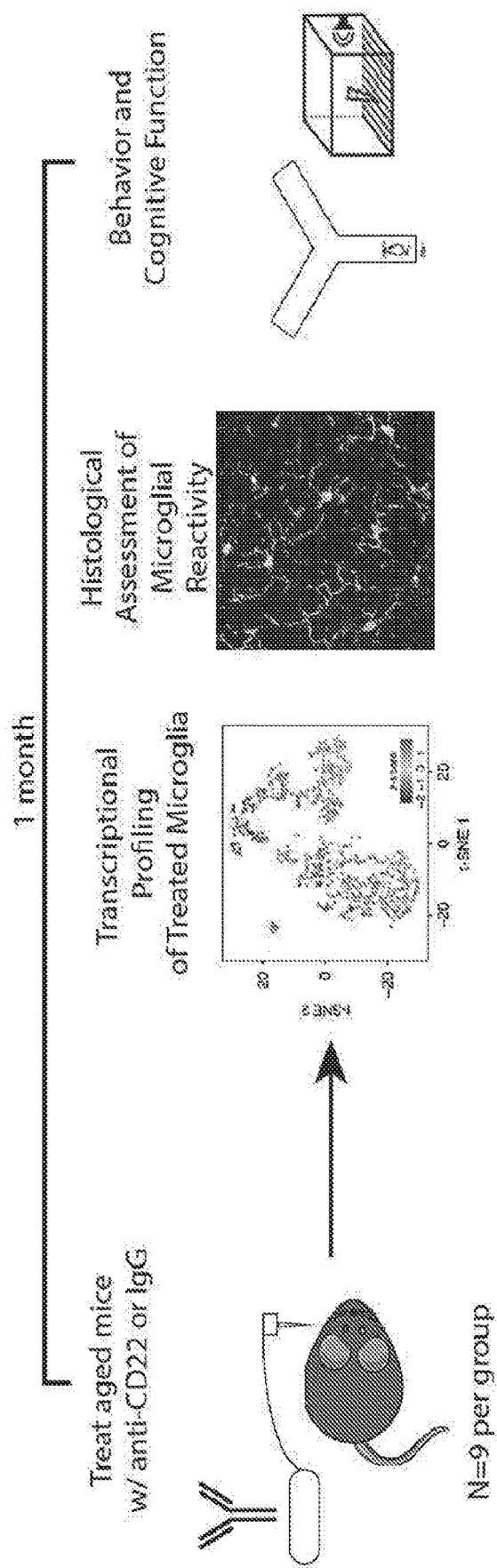
FIG. 23 shows a schematic diagram of methods used to assay the outcomes of long-term CD22 blockade in aged mice. One mg/mL Anti-CD22 (clone Cy34.1) or IgG1 control antibody were labeled with Alexa647, and loaded into an osmotic pump to deliver 0.25 uL/hour for 28 days to the right lateral ventricle. After 28 days, mice were tested for learning and memory including contextual fear conditioning.
Figure 24:
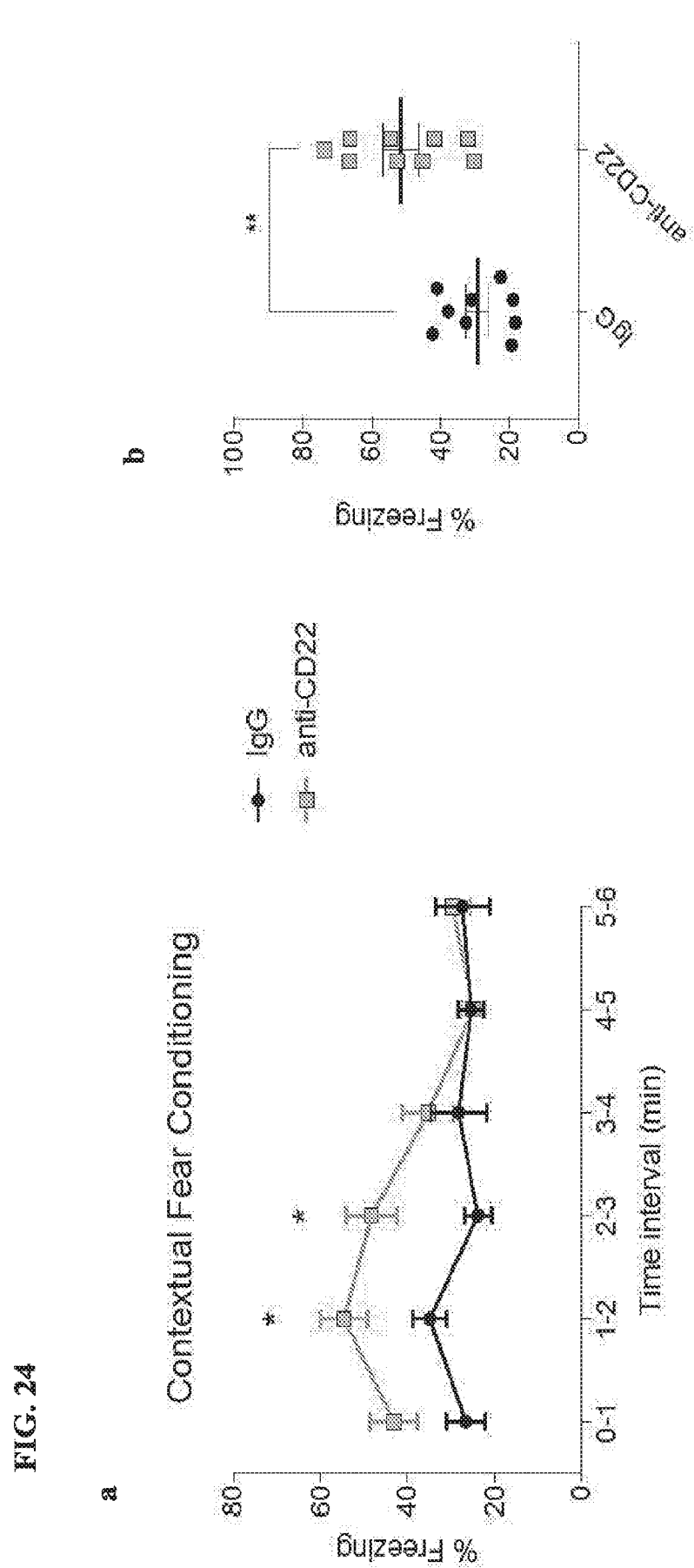
FIG. 24 shows that intracerebroventricular (ICV) anti-CD22 antibody improves cognitive function in aged mice demonstrated by improved contextual fear conditioning by the methods of Villeda et al. (Villeda et al. Young blood reverses age-related impairments in cognitive function and synaptic plasticity in mice. *Nat. Med.* 2014:20: 659-663). (b), shows % freezing at minutes 1-3. These results show that specific CD22 blockade slows cognitive decline in aged animals, and is of value in conditions in which the aging phenotype of microglia participates in pathogenesis. Other cells in the mouse central nervous system (CNS) do not express CD22.
Figure 25:
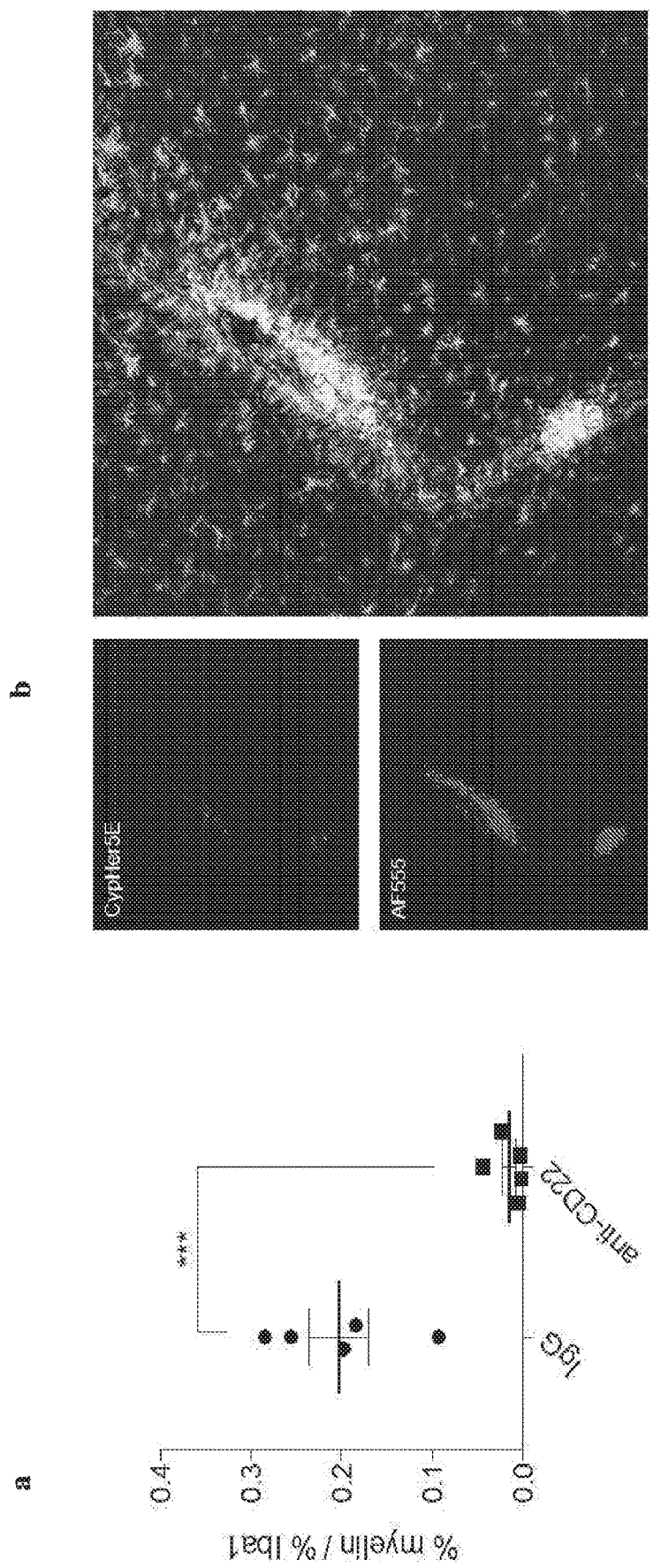
FIG. 25 shows that CD22 blockade promotes clearance of myelin debris. Purified CNS myelin was prepared using the method of Jorge et al. (Jorge et al. *Current Protocols in Cell Biology* (2006) 3.25.1-3.25.19.) After serial discontinuous sucrose gradients, myelin was double labeled with AlexaFluor 555 (constitutively fluorescent) NHS and CypHer5E (pH-dependent fluorescence) NHS. Labeled myelin was then co-injected with either anti-CD22 or IgG control as described above in experiments with Aβ and alpha-synuclein. Results show that CD22 blockade promotes clearance of myelin by microglia in the aged brain. CNS myelin accumulates with age (Safaiyan et al. Age-related myelin degradation burdens the clearance function of microglia during aging. *Nature Neuroscience* 19, 995-998). Accordingly, blockade of myelin accumulation reduces the debris burden in the CNS observed with age and other pathogenic conditions associated with myelin accumulation including, for example, spinal cord injury.
Figure 28:
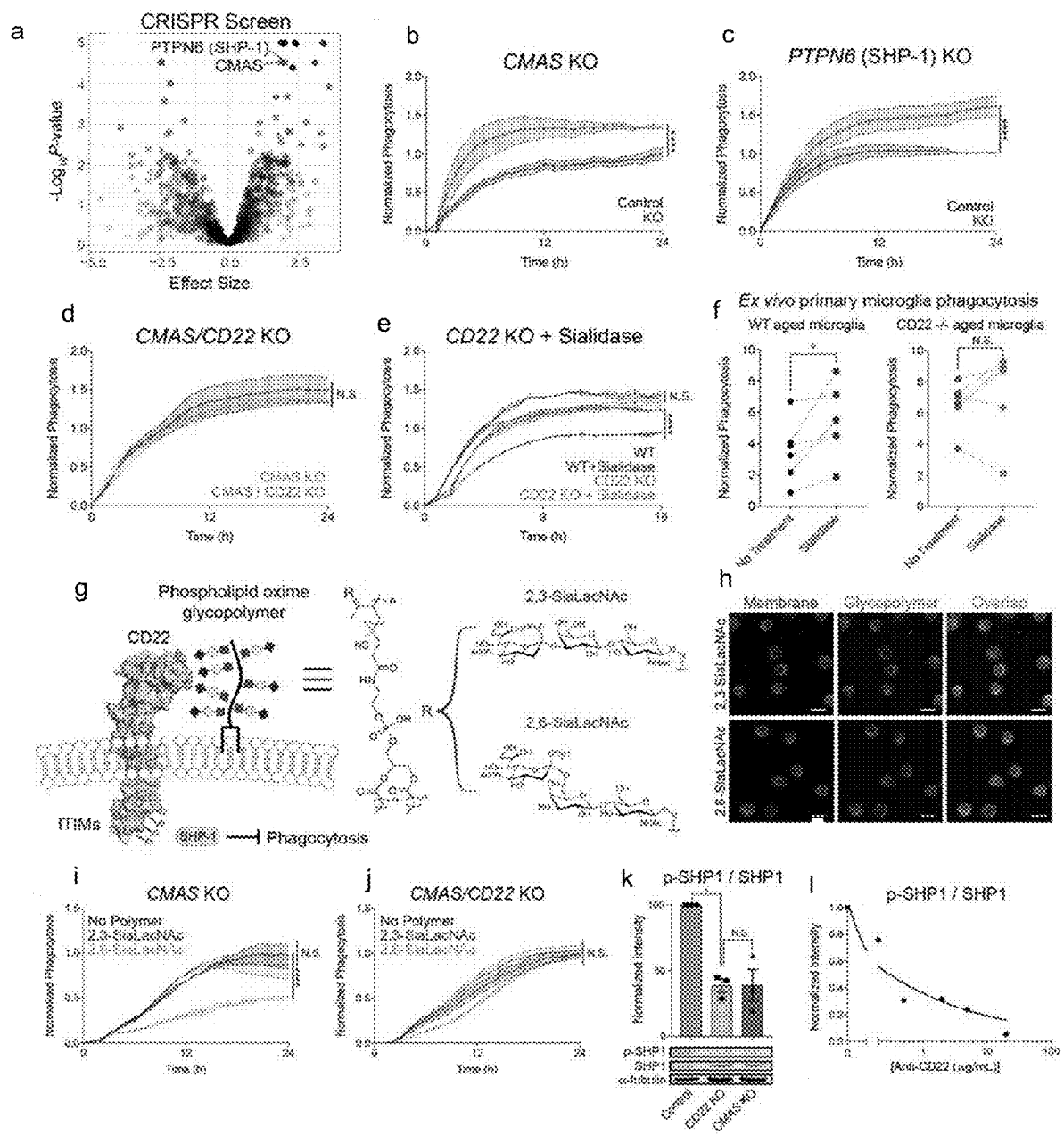
FIG. 28 shows that CD22 mediates the anti-phagocytic effect of cell-surface sialic acid. (a), Volcano plot showing significant hits from CRISPR-Cas9 screen targeting 2,015 drug targets, kinases, and phosphatases in BV2 cells. Knockouts that promote phagocytosis have a positive effect size and knockouts that inhibit phagocytosis have a negative effect size (dashed line, P=0.05). (b), Phagocytosis of pH-sensitive fluorescent beads by control (black) or CMAS KO (red) BV2 cells (n=3, **P<0.00005, ANOVA with repeated measures; shading, S.E.M.). (c), Phagocytosis of pH-sensitive fluorescent beads by control (black) or PTPN6 KO (red) BV2 cells (n=3, P<0.00005, ANOVA with repeated measures; shading, S.E.M.). (d), Phagocytosis of pH-sensitive fluorescent beads by control CMAS KO BV2 cells or CMAS/CD22 double KO BV2 cells (n=3, N.S. not significant, ANOVA with repeated measures; shading, S.E.M.). (e), Phagocytosis of pH-sensitive fluorescent beads by WT (black), WT+ sialidase (red), CD22 KO (blue), or CD22 KO+ sialidase (green) BV2 cells (n=3, **P<0.00005, N.S. not significant, ANOVA with repeated measures; shading, S.E.M.). (f), Microglia were acutely isolated from the brains of aged (18 m.o.) WT (left) or CD22−/−(right) mice, treated with or without sialidase, and incubated with pH-sensitive fluorescent latex beads. Microglia specific phagocytosis was measured using flow cytometry (n=6, *P<0.05, paired t-test). (g), Schematic of cell-surface glycan engineering using lipid tail-functionalized glycopolymers bearing sialic acid α2,3- or α2-6-linked to N-acetyllactosamine. ITIMs=immunoreceptor tyrosine-based inhibitory motifs, SHP-1=Src homology region 2 domain-containing phosphatase-1. (h), Representative images of BV2 cells coated with AlexaFluor 488 conjugated glycopolymers (green) and stained with a plasma membrane-specific dye (CellMask) showing overlap (yellow). Scale bar=25 microns. (i), Phagocytosis of pH-sensitive fluorescent beads monitored by time-lapse microscopy over 24 hours, imaged every hour. CMAS KO BV2 cells were coated with no polymer (black), 2,3-linked sialic acid (purple) or 2,6-linked sialic acid (orange) prior to phagocytosis (n=3, ****P<0.00005, ANOVA with repeated measures; shading, S.E.M.). (j), Same experiment as in (I) except using CMAS/CD22 double KO BV2 cells (n=3, N.S. not significant, ANOVA with repeated measures; shading, S.E.M.). (k), Intensity quantification and image of western blot showing ratio of active phosphorylated SHP1 (p-SHP1) to total SHP1 in control (dark blue), CD22 KO (light blue), and CMAS KO (green) BV2 cells, normalized to a loading control protein ($\alpha$-tubulin) (n=3, *P<0.05, N.S. not significant, one-way ANOVA with Tukey's correction). (l), Quantification of western blot assessing ratio of active pSHP1 to total SHP1 protein in BV2 cells pretreated with various concentrations of anti-CD22. Blue line represents the fitted variable slope inhibitor-response curve.

CD22 is expressed on B-cells, where it negatively regulates BCR signaling through sialic acid binding interactions and recruitment of SHP-1 phosphatase via immunoreceptor tyrosine-based inhibitory motifs (ITIMs)[55]. To test for signaling partners of CD22 on microglia, we analyzed the initial CRISPR-Cas9 screen for hits related to CD22 function. Gene ontology analysis revealed that the 'BCR signaling' annotation was significantly enriched among hits that promote phagocytosis (FIG. 30h). Other hits with this annotation were CMAS, a key enzyme in sialic acid synthesis, and PTPN6, which codes for SHP-1. Although not differentially expressed with age, CMAS and PTPN6 were among the most significant hits in the drug targets, kinases, and phosphatases CRISPR-Cas9 screen (FIG. 28a). Independent validation experiments confirmed that knocking out CMAS or PTPN6 robustly promotes phagocytosis (FIGS. 17b,c, FIGS. 34a,b,c), phenocopying CD22 ablation. Knocking out both CD22 and CMAS simultaneously did not produce an additive phagocytic effect (FIG. 28d), indicating that the two genes participate in a shared pathway via genetic interaction, and that sialic acid participates in microglial CD22 signaling.

Figure 34:
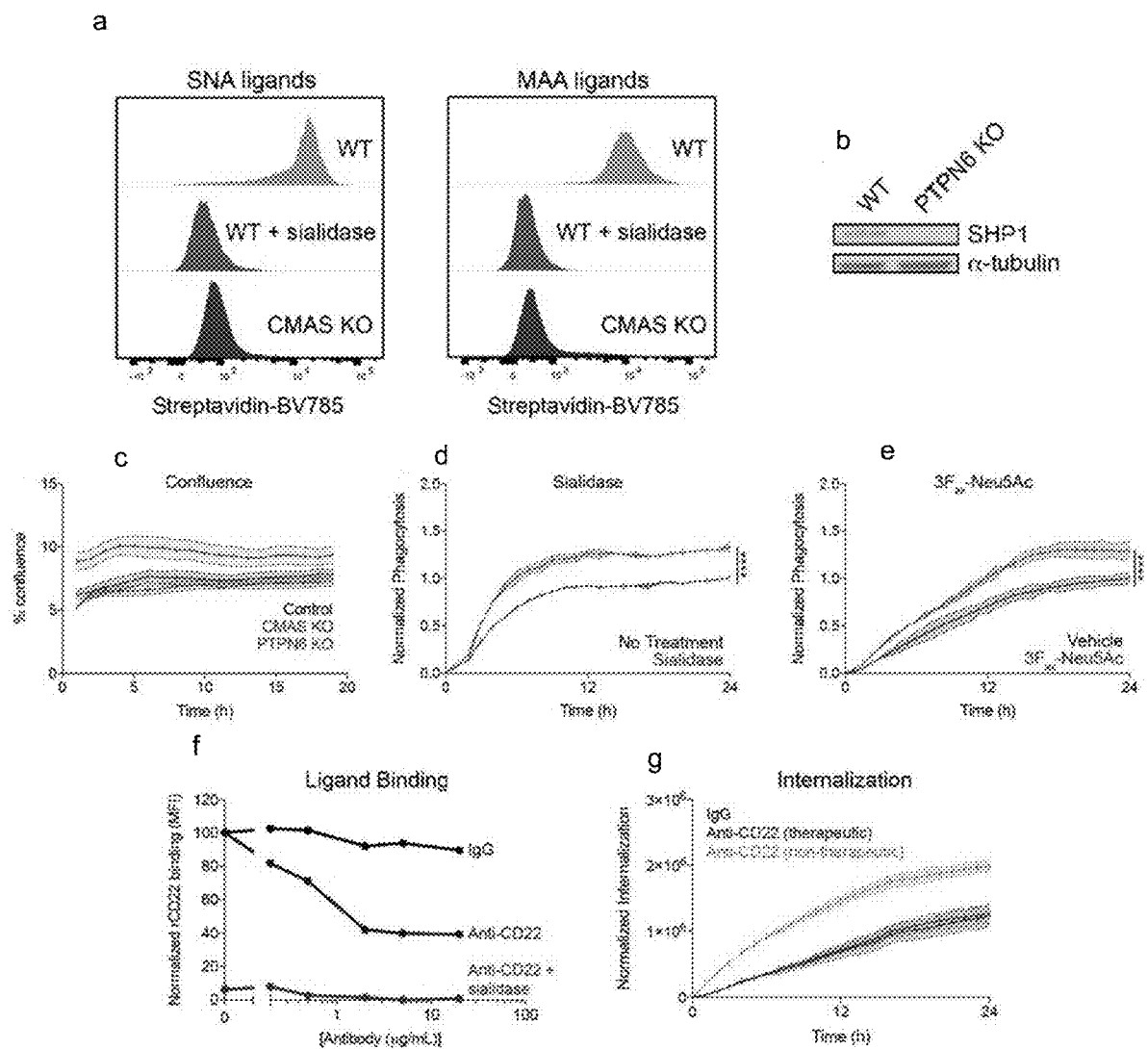
FIG. 34 shows that BCR signaling genes regulate phagocytosis. (a), Histograms of SNA and MAA ligand expression in WT BV2 cells (orange), WT BV2 cells pretreated with sialidase (blue), and CMAS KO cells (red) assessed by flow cytometry. Sialidase treatment and CMAS KO reduce sialic acid ligands on the cell surface. (b), Western blot showing SHP1 protein expression in WT and PTPN6 KO BV2 cells. (c), Percent confluence of control (gray), CMAS KO (red), and PTPN6 KO (blue) BV2 cells during time-lapse microscopy phagocytosis assays (n=3, N.S. not significant). (d), Phagocytosis of pH-sensitive fluorescent beads monitored by time-lapse microscopy over 24 hours, imaged every hour. BV2 cells were either untreated (black) or treated with sialidase (red) prior to phagocytosis (n=3, **P<0.00005, ANOVA with repeated measures; shading, S.E.M.). (e), Phagocytosis of pH-sensitive fluorescent beads by BV2 cells treated with DMSO (black) or a selective sialic acid synthesis inhibitor, 3Fax-Neu5Ac, (red) prior to and during phagocytosis (n=3, **P<0.00005, ANOVA with repeated measures; shading, S.E.M.). (f), Recombinant mouse CD22-human Fc fusion protein was pre-complexed with AF647 anti-human Fc secondary antibody, treated with various concentrations of IgG (black) or anti-CD22 (blue, red), and subsequently allowed to bind to ligands on the surface of BV2 cells or BV2 cells pretreated with sialidase (red). Binding was measured by flow cytometry. (g), Internalization of IgG (black), therapeutic anti-CD22 (blue), and non-therapeutic anti-CD22 (green) conjugated to a pH-sensitive fluorescent dye by BV2 cells assessed by time-lapse microscopy.

Sialic acid cell-intrinsically inhibits phagocytosis. Loss of sialic acid facilitates acquisition of phagocytic potential during differentiation of monocytes to mature macrophages[56], and dendritic cells from mice lacking a specific sialyltransferase display enhanced phagocytic capacity[57]. Based on these previous studies, we observed that removal of sialic acid via treatment with sialidase or 3Fax-Neu5Ac, a specific sialic acid biosynthesis inhibitor[58], promotes phagocytosis in BV2 cells (FIG. 34d,e). The pro-phagocytic effect of sialic acid inhibition was completely abrogated in the absence of CD22 (FIG. 28e). To validate this effect in primary cells, we isolated microglia from aged WT or CD22−/− mice, pretreated the cells with or without sialidase, and incubated them with pH-sensitive fluorescent latex particles. Cleavage of cell-surface sialic acid promoted phagocytosis in WT microglia but had no effect in CD22−/− microglia (FIG. 28f).

To test CD22-sialic acid receptor-ligand interactions, we used synthetic glycopolymers functionalized with lipid tails to introduce defined glycans onto the cell-surface[5] (FIG. 28g). We decorated CMAS knockout cells, devoid of endogenous sialic acid, with synthetic glycopolymers bearing sialic acid linked to N-acetyllactosamine in either an α2-3- or α2-6-configuration. These linkages confer sialic acid with distinct binding specificities and biological functions. To confirm membrane incorporation, we conjugated each glycopolymer to a fluorophore and assessed overlap with a plasma membrane specific dye (FIG. 28h). We observed similar levels of membrane incorporation for α2-3- and α2-6-linked sialic acid glycopolymers. We found that addition of α2-6-linked sialic acid, the preferred ligand of CD22[60], but not α2-3-linked sialic acid, inhibited phagocytosis in CMAS KO cells (FIG. 28i). Next, we performed the same experiment on a CMAS/CD22 double knockout background. The anti-phagocytic effect of α2-6-linked sialic acid was abrogated in the absence of CD22 (FIG. 28j). These findings demonstrate that α2-6-linked sialic acid inhibits phagocytosis in a CD22-dependent manner.

To transduce the inhibitory signal of sialic acid ligands, most Siglecs contain one or more cytoplasmic ITIM domains[61]. In the context of B-cell biology, CD22 is normally sequestered away from the BCR in nanoclusters of homo-oligomers[62]. Upon antigen binding, CD22 associates with the BCR, where Lyn kinase phosphorylates its ITIM domains, recruiting SHP-1, which itself is phosphorylated yielding active pSHP-1[63], a phosphatase that inhibits downstream BCR-induced calcium signaling. SHP-1 has also been shown to negatively regulate phagocytosis[64,65]. We assessed basal SHP-1 activity in a variety of knockout BV2 lines, and found that CD22 KO cells express a reduced ratio of active pSHP-1 to total SHP-1 protein, comparable to CMAS KO cells (FIG. 28k). Furthermore, treatment with a CD22 ligand-blocking antibody (FIG. 34f,g) decreased SHP-1 activity in a dose-dependent manner (FIG. 28l). These data indicate that α2-6-linked sialic acid binds CD22, thereby promoting inhibitory SHP-1 signaling to restrain the phagocytic capacity of microglia.

Figure 29:
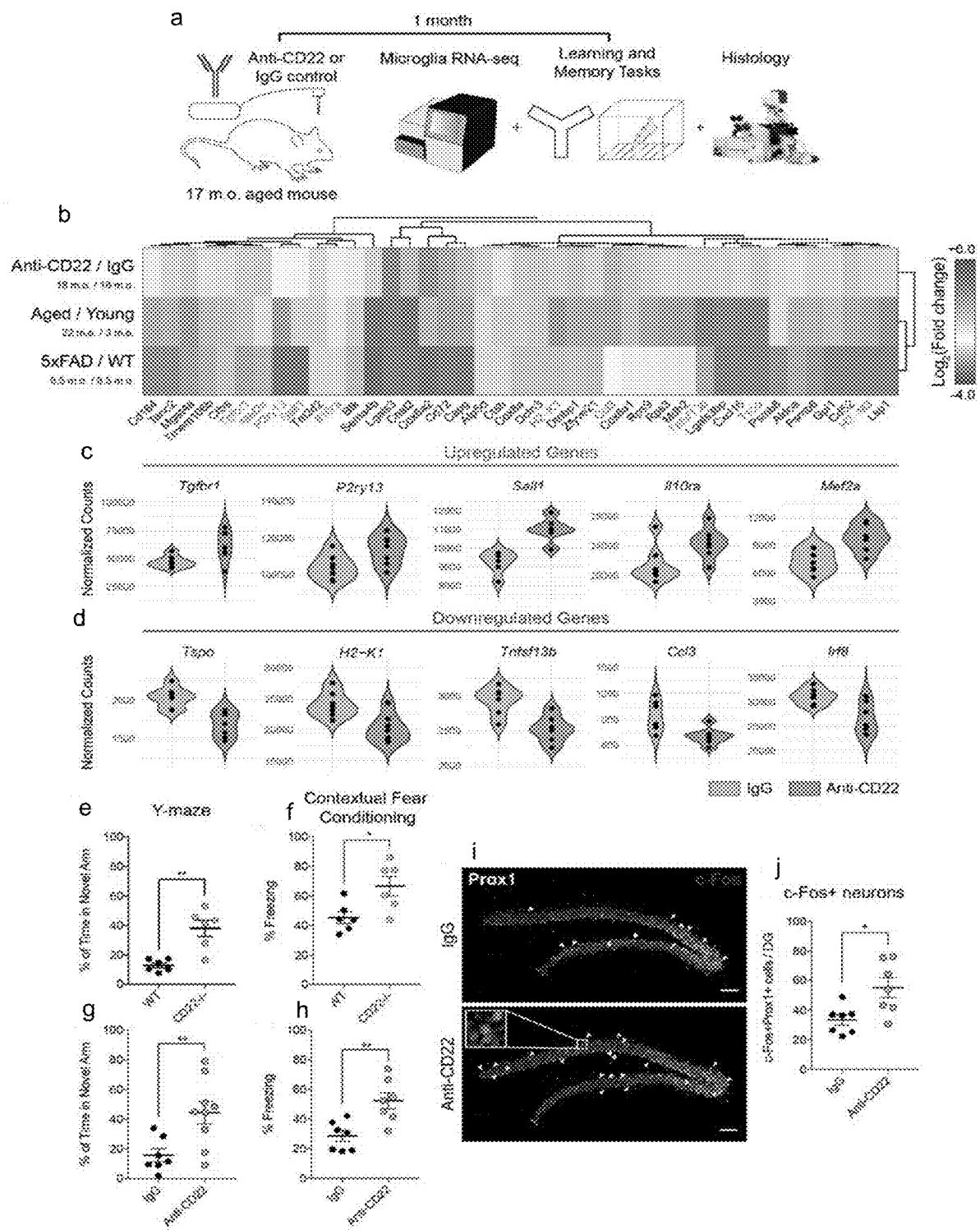
FIG. 29 shows that long-term CD22 blockade restores microglial homeostasis and improves cognitive function in aged mice. (a), Schematic of long-term CD22 inhibition. Aged mice were implanted with an osmotic pump delivering IgG or anti-CD22 continuously over 1 month via the lateral ventricle directly into the CSF. Experimental endpoint readouts included microglia RNA-seq, learning and memory tasks, and histological analysis of the hippocampus. (b), Hierarchically clustered heatmap of Log-2 normalized fold changes between microglia from anti-CD22 (n=7) and IgG (n=7) treated mice, between microglia from aged (22 m.o., n=3) and young (3 m.o., n=3) mice (Deczkowska, et al., 2017), and between microglia from the 5XFAD AD-model (8.5 m.o., n=5) and age-matched WT (8.5 m.o., n=5) mice (Wang, et al., 2015). Significantly differentially expressed genes (P-value<0.05) between experimental and control groups that were shared among the three datasets are displayed. Upregulated (red) and downregulated (blue) genes of interested are highlighted. (c), Normalized read counts of IgG (gray, n=7) and anti-CD22 (green, n=7) treated microglia showing upregulation of homeostatic microglia genes following anti-CD22 treatment. FDR<10% for all comparisons. (d), Normalized read counts of IgG (gray, n=7) and anti-CD22 (green, n=7) treated microglia showing downregulation of activated microglia genes. FDR<10% for all comparisons. (e), Working memory and exploratory behavior in aged (18 m.o.) WT and CD22−/− mice as assessed by % of time spent in the novel arm during the first two minutes of the retrieval trial in a forced alternation Y-maze behavioral test (**P<0.005, t-test). (f), Contextual memory in aged (18 m.o.) WT and CD22−/− mice as assessed by % of time displaying freezing behavior during the first two minutes of the retrieval trial in a contextual fear conditioning test (independent cohort from Y-maze mice, *P<0.05, t-test). (g), Working memory and exploratory behavior in IgG (n=7) and anti-CD22 (n=9) treated mice as assessed by % of time spent in the novel arm during the first two minutes of the retrieval trial in a forced alternation Y-maze behavioral test (P<0.005, t-test). (h), Contextual memory in IgG (n=7) and anti-CD22 (n=7) treated mice as assessed by % of time displaying freezing behavior during the first two minutes of the retrieval trial in a contextual fear conditioning test (independent cohort from Y-maze mice, P<0.005, t-test). (i), Representative images of dentate gyri from IgG (top) and anti-CD22 (bottom) treated mice showing Prox1+ granule neurons (white) and c-Fos+ cells (red). White arrows indicate cFos+Prox1+ active granule neurons. Scale bar=100 microns. (j), Total number of Prox1+ granule neurons in the dentate gyrus that co-express the immediate early marker c-Fos quantified over 5 tissue sections (n=7, *P<0.05, t-test).
Figure 35:
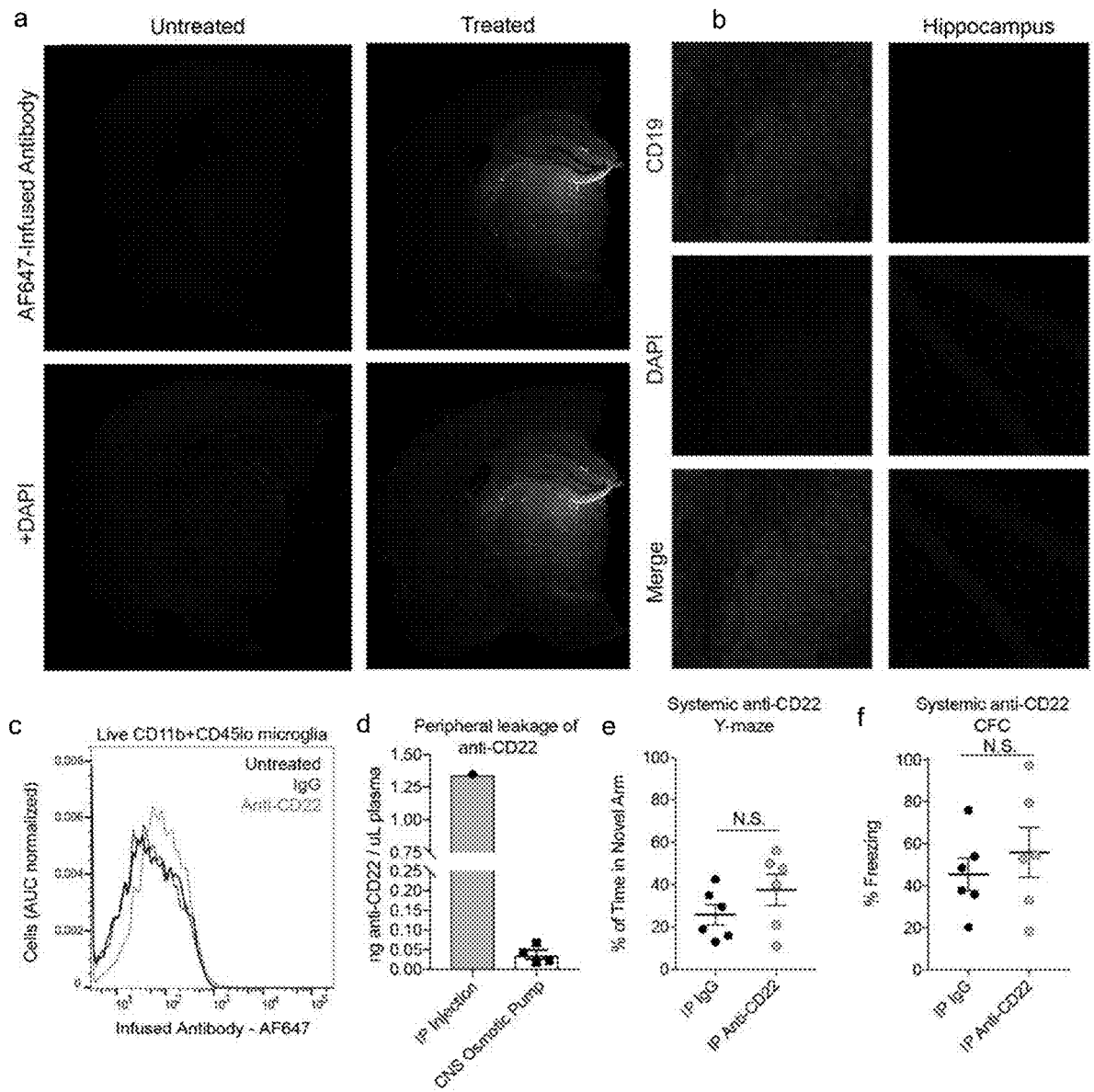
FIG. 35 shows the distribution of anti-CD22 in the brain and target engagement with microglia following long-term continuous intracerebroventricular infusion. (a), Representative coronal images of brains of untreated (left column) and IgG treated (right column) mice. IgG was labeled with an AlexaFluor647 NHS-ester (top row, white) to assess antibody distribution throughout the brain (bottom row, DAPI, blue). In addition to the para-ventricular areas, antibodies penetrated to the thalamus and hippocampus. (b), Representative images of CD19+B-cells (red, top row), DAPI (blue, middle row), and merged (bottom row) in the spleen (left, positive control) and hippocampus (right) of a mouse treated with anti-CD22 via intracerebroventricular osmotic pump. (c), Flow cytometry analysis of AF647-labeled antibody on microglia isolated from untreated (black), IgG (red), or anti-CD22 (blue) infused mice. Microglia from anti-CD22 treated mice display elevated AF647 signal, indicative of antibody target engagement. (d), Concentration of trans-cyclooctene-labeled anti-CD22 in the plasma 7 days after administration of 200 ug anti-CD22 via IP injection or intracerebroventricular osmotic pump infusion, assessed by in-gel fluorescence and quantification based on a standard curve. (e), Working memory and exploratory behavior in aged (18 m.o.) mice treated with IgG (black) or anti-CD22 (green) via IP injection weekly for one month as assessed by % of time spent in the novel arm during the first two minutes of the retrieval trial in a forced alternation Y-maze behavioral test (N.S. not significant, paired t-test). (f), Contextual memory aged (18 m.o.) mice treated with IgG (black) or anti-CD22 (green) via IP injection weekly for one month as assessed by % of time displaying freezing behavior during the first two minutes of the retrieval trial in a contextual fear conditioning test (independent cohort from Y-maze mice, *P<0.05, t-test).

Long-Term CD22 Blockade Promotes Microglial Homeostasis and Improves Cognitive Function in Aged Mice Aging and disease overwhelm the homeostatic function of microglia, leading to a distinctive transcriptional state[66] characterized by the downregulation of resting microglial signature genes and the upregulation of activated microglial signature genes. Because phagocytosis is a central homeostatic function of microglia, we tested whether CD22 blockade restores aged microglia to a homeostatic state. We implanted aged mice with osmotic pumps to continuously infuse a CD22 ligand-blocking antibody or an IgG control antibody directly into the cerebrospinal fluid for one month (FIG. 29a). As opposed to systemic antibody administration or CD22−/− mice, this intervention enabled CNS-specific targeting of CD22 without B-cell infiltration into the brain (FIG. 35b), or significant leakage into the periphery (FIG. 35d). We labeled the respective antibodies with a fluorescent dye to test drug distribution within the brain parenchyma (FIG. 35a), and target engagement with CD22 on microglia (FIG. 35c).

Figure 36:
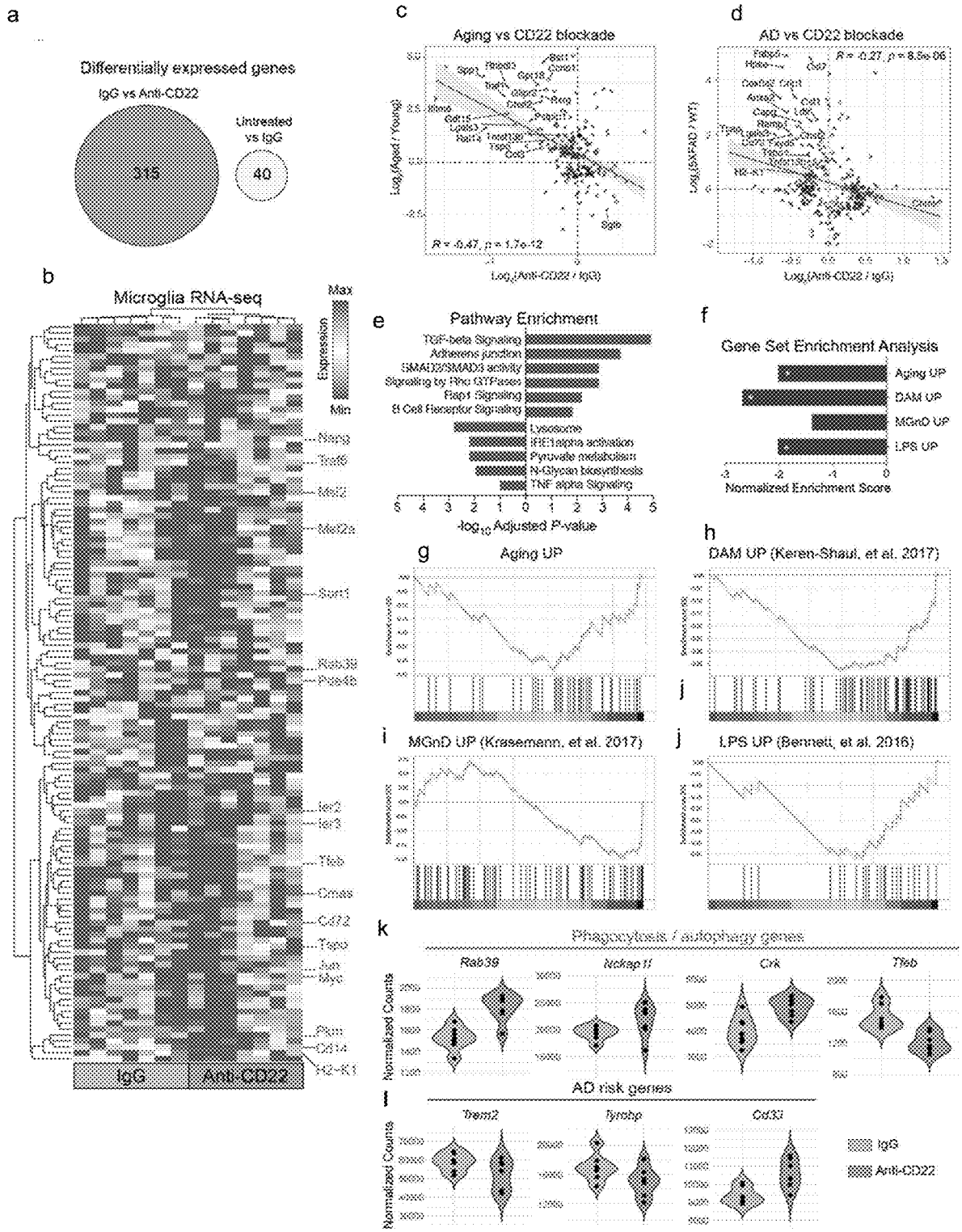
FIG. 36 shows that anti-CD22 treatment partially reverses age- and disease-related microglia transcriptional signatures. (a), Venn diagram showing the lack of any intersection between 315 genes differentially expressed between IgG and anti-CD22 treated microglia and 40 genes differentially expressed between untreated and IgG treated microglia at an FDR cutoff of 10%. (b), Hierarchically clustered heatmap of normalized read counts from IgG and anti-CD22 treated microglia, normalized by row mean. The top-100 differentially expressed genes are shown (n=7). (c), Enrichr analysis showing overrepresentation of genes upregulated (red) and downregulated (blue) by anti-CD22 treatment in various pathways. (d), Gene set enrichment analysis (GSEA) showing normalized enrichment score between microglia genes modulated by anti-CD22 treatment and genes upregulated in aging microglia, disease-associate microglia (DAM, Keren-Shaul, et al. 2017), microglial neurodegenerative phenotype (MGnD, Krasemann, et al. 2017), and microglia from lipopolysaccharide treated mice (LPS, Bennett, et al. 2016) (*FDR<0.05). (e), GSEA showing ranked enrichment scores between microglia genes modulated by anti-CD22 treatment and genes upregulated in aging microglia. (f), GSEA with disease-associate microglia genes (DAM, Keren-Shaul, et al. 2017). (g) GSEA with microglial neurodegenerative phenotype genes (MGnD, Krasemann, et al. 2017). (h), GSEA with lipopolysaccharide-upregulated microglia genes (LPS, Bennett, et al. 2016). (i), Scatter plot showing negative correlation between genes differentially expressed between anti-CD22 and IgG treated microglia and genes differentially expressed between aged and young microglia (R=−0.47, P=1.7e-12, blue line, linear regression, Spearman correlation). (j), Scatter plot showing negative correlation between genes differentially expressed between anti-CD22 and IgG treated microglia and genes differentially expressed between 5×FAD and WT microglia (R=−0.27, P=8.5e-6, blue line, linear regression, Spearman correlation). (k), Normalized read counts of IgG (gray) and anti-CD22 (green) treated microglia showing the differential expression of regulators of phagocytosis and autophagy. (1), Normalized read counts of IgG (gray) and anti-CD22 (green) treated microglia showing the differential expression of selected AD-risk genes enriched in microglia.

Following one month of continuous infusion, we performed RNA-seq on purified microglia from the hemi-brains of treated mice contralateral to the cannulation site. This allowed a focus on transcriptional changes due to anti-CD22 treatment while minimizing the potential for injury-induced changes to confound the analysis. We found very few transcriptional changes between microglia from untreated and IgG-infused mice (FIG. 36a). In contrast, we found 315 differentially expressed genes between IgG and anti-CD22 treated microglia meeting a false discovery rate (FDR) cutoff of 10% (FIG. 36b). We compared these genes to those that are differentially expressed between microglia from young and aged mice[67], and between microglia from wild-type and end-stage 5×FAD AD-model mice[68] (FIG. 29b). Anti-CD22 treatment promoted the upregulation of homeostatic microglial signature genes and the downregulation of activated microglial signature genes, partially reversing the transcriptional hallmarks of aging and disease (FIGS. 36c,d).

Figure 37:
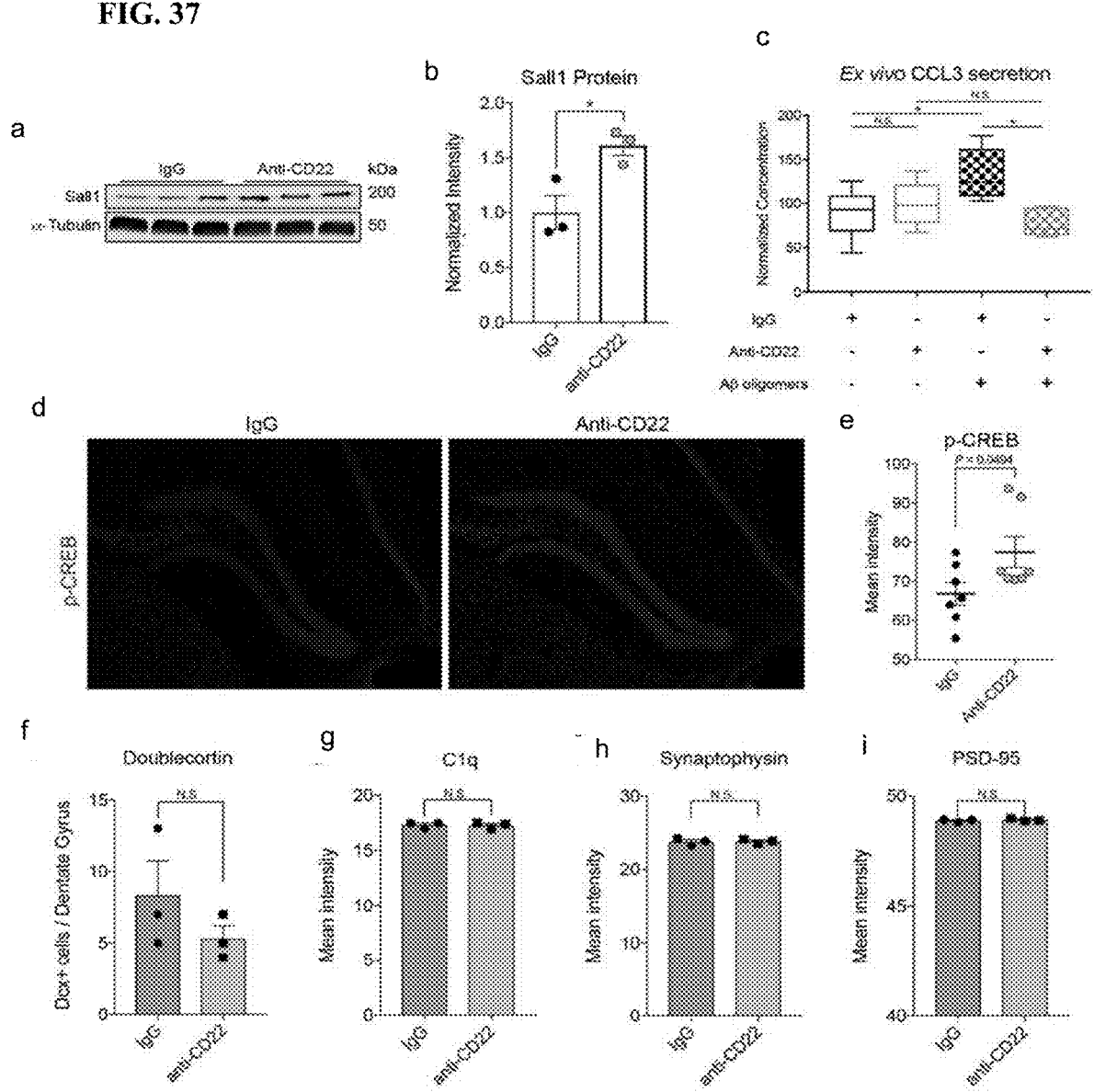
FIG. 37 shows a histological assessment of long-term CD22 blockade in the hippocampus. (a), Western blot for Sall1 and α-Tubulin (loading control) in whole hippocampus lysates from IgG and anti-CD22 treated mice. (b), Quantification of (a) showing upregulation of Sall1 protein in anti-CD22 hippocampi (n=3, *P<0.05, t-test). (c), Protein concentration of CCL3 in the supernatant of FACS-isolated aged microglia treated for 8 hours with IgG or anti-CD22 in the absence or presence of Aβ oligomers (n=6, N.S. not significant, *P<0.05, ANOVA with Tukey's multiple hypothesis correction). (d), Representative images of p-CREB expression (red) in the dentate gyrus of IgG (left) and anti-CD22 (right) treated mice. (e), Quantification of p-CREB mean intensity in the dentate gyrus of IgG (black) and anti-CD22 (green) treated mice (n=7, t-test). (f), Quantification of total doublecortin-positive cells in three equally-spaced dentate gyrus sections of IgG (black) and anti-CD22 (green) treated mice (n=3, N.S. not significant). (g), Quantification of C1q mean intensity in the hippocampus of IgG (black) and anti-CD22 (green) treated mice (n=3, N.S. not significant). (h), Quantification of synaptophysin (pre-synaptic marker) mean intensity in the hippocampus of IgG (black) and anti-CD22 (green) treated mice (n=3, N.S. not significant). (i), Quantification of PSD-95 (post-synaptic marker) mean intensity in the hippocampus of IgG (black) and anti-CD22 (green) treated mice (n=3, N.S. not significant).

Among significantly upregulated genes in anti-CD22 treated microglia were various members of the TGF-beta signaling pathway, including the upstream receptor Tgfbr1 (FIG. 29c, FIG. 36e), which are critical for microglial development[38,69] and neuroprotection[70,71]. Other significantly upregulated genes included P2ry13, a purinergic receptor enriched in resting microglia[51], Il10ra, which transduces anti-inflammatory IL-10 signaling, Mef2a, a transcription factor correlated with the establishment of homeostatic microglial function in adulthood[72], and Sall1, a transcriptional regulator of microglial homeostasis[73]. To test this upregulation at the protein level, we performed a Western blot analysis of hippocampi from IgG and anti-CD22 infused mice and found a significant increase in Sall1 expression (FIGS. 37a,b).

Among significantly downregulated genes in anti-CD22 treated microglia were various hallmarks of activated microglia typically observed during injury51, aging, and disease[74-76] (FIGS. 36f-j). These included subunits of the MHC Class-II complex and translocator protein (Tspo), a biomarker of disease progression and microglial activation in AD, PD, and amyotrophic lateral sclerosis (ALS)[77] (FIG. 29d). Irf8, a transcriptional regulator that mediates the transition from homeostatic to activated microglia upon injury[78], was downregulated in anti-CD22 treated microglia. Multiple pro-inflammatory cytokine genes were downregulated by anti-CD22 treatment including Tnfsf13b, which codes for B-cell-activating factor of the tumor-necrosis-factor family (BAFF), and Ccl3, a chemokine elevated in models of amyloidosis and tauopathy[26] and implicated in hippocampal-dependent memory impairment[79]. Although mRNA and protein levels are not always correlated[80], these concomitant transcriptional changes suggest that long-term CNS-targeted anti-CD22 treatment partially restores aged microglia to a homeostatic state.

CD22 alters cytokine secretion in lipopolysaccharide-stimulated microglia[81]. To test whether CD22 regulates CCL3 secretion in the context of aging, and to validate RNA-seq results at the protein level, we purified microglia from aged mice, treated with IgG or anti-CD22 ex vivo, and subjected cell supernatants to bead-based multiplexed immunoassays. We observed no effect of CD22 blockade on CCL3 secretion at baseline (FIG. 37c). However, when we stimulated microglia with oligomeric Aβ, a potent damage-associated molecular pattern (DAMP) in the aging brain[82], we observed a large spike in CCL3 secretion that was abrogated by CD22 blockade (FIG. 37c). These data show that CD22 blockade reduces CCL3 secretion in the presence of extracellular debris, providing a link between the pro-phagocytic and homeostatic effects of inhibiting microglial CD22.

Microglia contribute to impaired cognitive function in aging and disease through synaptic pruning and pro-inflammatory cytokine secretion[67,83-85]. Conversely, they have also been implicated in improved cognitive function through clearance of pathological protein aggregates in AD mouse models[86] and neurotrophic factor[87] or anti-inflammatory cytokine secretion[88,89]. To test the consequences of CD22 inhibition on age-related cognitive dysfunction, we tested hippocampal-dependent learning and memory function in aged WT and CD22−/− mice using the forced alternation Y-maze and fear conditioning paradigms. CD22−/− mice exhibited improved spatial memory and exploratory behavior as measured by time spent in the novel arm of the Y-maze (FIG. 29e). Moreover, CD22−/− mice displayed increased freezing behavior in the fear conditioning paradigm, indicative of improved contextual associative memory (FIG. 29f). To test whether microglial CD22 inhibition was responsible for this behavioral phenotype, we assessed cognitive function in aged mice infused with IgG or anti-CD22 directly into the CNS. Blocking CD22 in the CNS phenocopied the learning and memory improvements seen in CD22−/− mice (FIGS. 29g,h) indicating that microglial CD22 negatively regulates cognitive function in the aging brain. We did not observe a significant cognitive improvement in aged mice treated systemically with anti-CD22 via intraperitoneal injection, indicating that CNS-penetration is necessary for the beneficial effect of CD22 blockade, and that peripheral B-cells are unlikely to contribute to this effect (FIGS. 35e,f).

The hippocampal-dependent behavioral phenotypes were accompanied by an increase in the number of hippocampal Prox1+ dentate granule neurons expressing c-Fos, an immediately early gene induced by neuronal activation[90] (FIG. 29i,j). In addition, anti-CD22 treatment promoted an increase in phosphorylated cyclic AMP responsive element-binding protein (p-CREB) (FIGS. 37d,e) a plasticity-related marker[91], but did not alter hippocampal neurogenesis as assessed by doublecortin-positive neuroblasts (FIG. 37f), phenocopying rejuvenation studies[92,93]. We observed no difference in C1q deposition (FIG. 37g) or synaptic density assessed by the intensity of pre- and post-synaptic markers, synaptophysin and PSD-95 (FIGS. 37h,i). Long-term CD22 blockade reprograms aged microglia to a homeostatic transcriptional state, increases markers of neuronal activation in the hippocampus, and, ultimately, improves cognitive function in aged mice.

Figure 38:
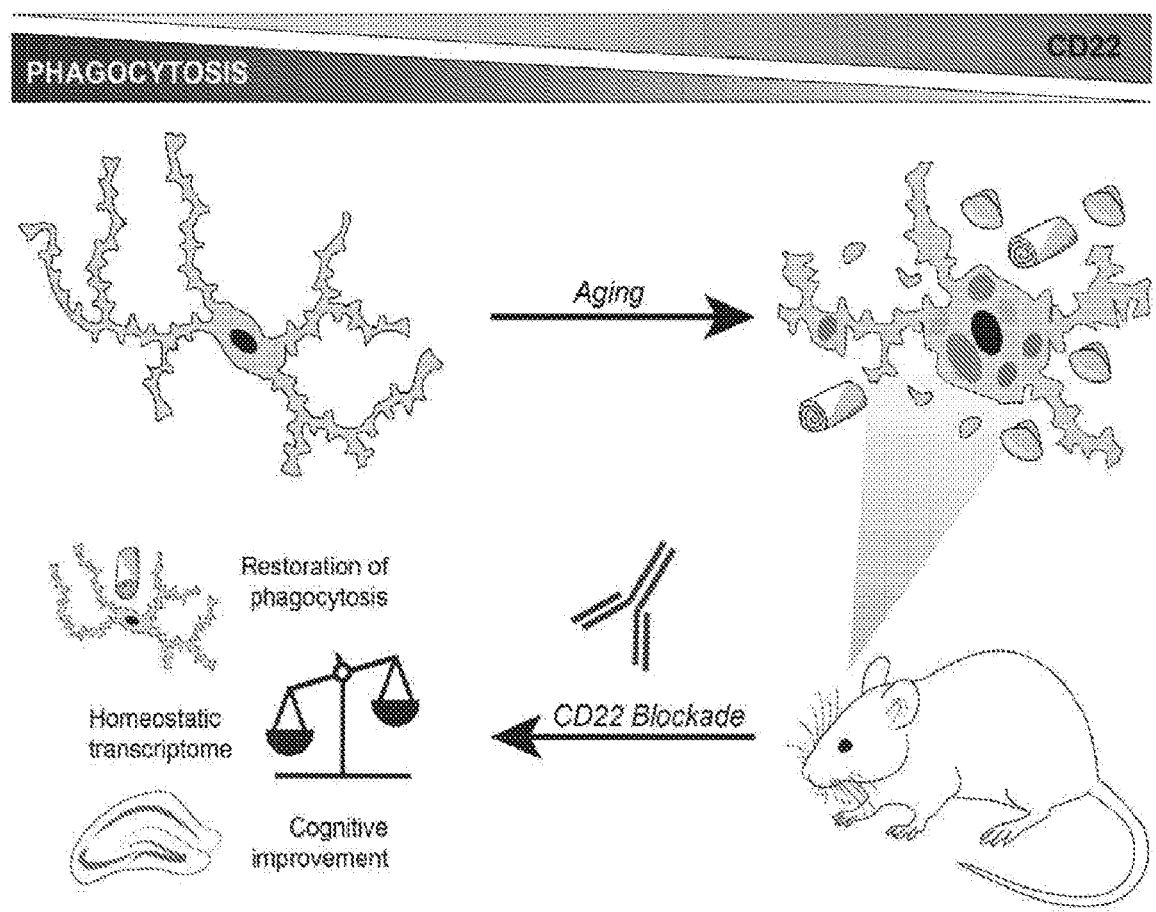
FIG. 38 depicts that microglial phagocytosis declines with age, accompanied by a concomitant increase in CD22 expression. CD22 inhibition restores phagocytosis, promotes a homeostatic transcriptional state, and improves cognitive function in aged mice.

These data indicate that CD22 is a negative regulator of phagocytosis that is upregulated on aged microglia. CD22 mediates the anti-phagocytic effect of α2-6-linked sialic acid, and inhibition of CD22, either via antibody blockade or genetic ablation, promotes the clearance of myelin debris, Aβ oligomers, and α-synuclein fibrils in vivo. Long-term CD22 inhibition partially reverses the transcriptional signature of age- and disease-related microglia and improves cognitive function in aged mice (FIG. 38).

Environmental cues shape microglial identity[69,94,95]. Based on an scRNA-seq dataset of microglia during development[96], CD22 is enriched in a subpopulation of postnatal day 7 microglia (FIG. 33d), a time point corresponding to the peak of synaptic pruning and programmed cell death[97]. This subpopulation, termed proliferative region-associated microglia (PAM), are involved in the phagocytosis of apoptotic oligodendrocytes and express a transcriptional signature resembling disease-associated microglia present in aged and AD brains. In addition to the upregulation of homeostatic microglial signature genes and the downregulation of activated microglial signature genes, the RNA-seq analysis revealed that anti-CD22 treatment promotes the expression of Rab-, Rap1-, and Rho-GTPase signaling cascades (FIGS. 36c,i), which participate in vesicle and membrane trafficking during phagocytosis. Conversely, TFEB, a regulator of lysosomal biogenesis and autophagy induced by lipid starvation[98,99], was downregulated in anti-CD22 treated microglia. These changes indicate that CD22 inhibition promotes phagocytosis, leading to a nutrient-rich metabolic state in aged microglia in which TFEB is suppressed. TFEB, together with TFE3, regulates the transcription of numerous pro-inflammatory molecules[100], including CCL3. Age-related impairments in the perivascular glymphatic system[101] and the meningeal lymphatic system[102] affect cognitive function, and CD22-regulated microglial phagocytosis cooperates with these pathways to control debris accumulation in the aging brain.

Figure 39:
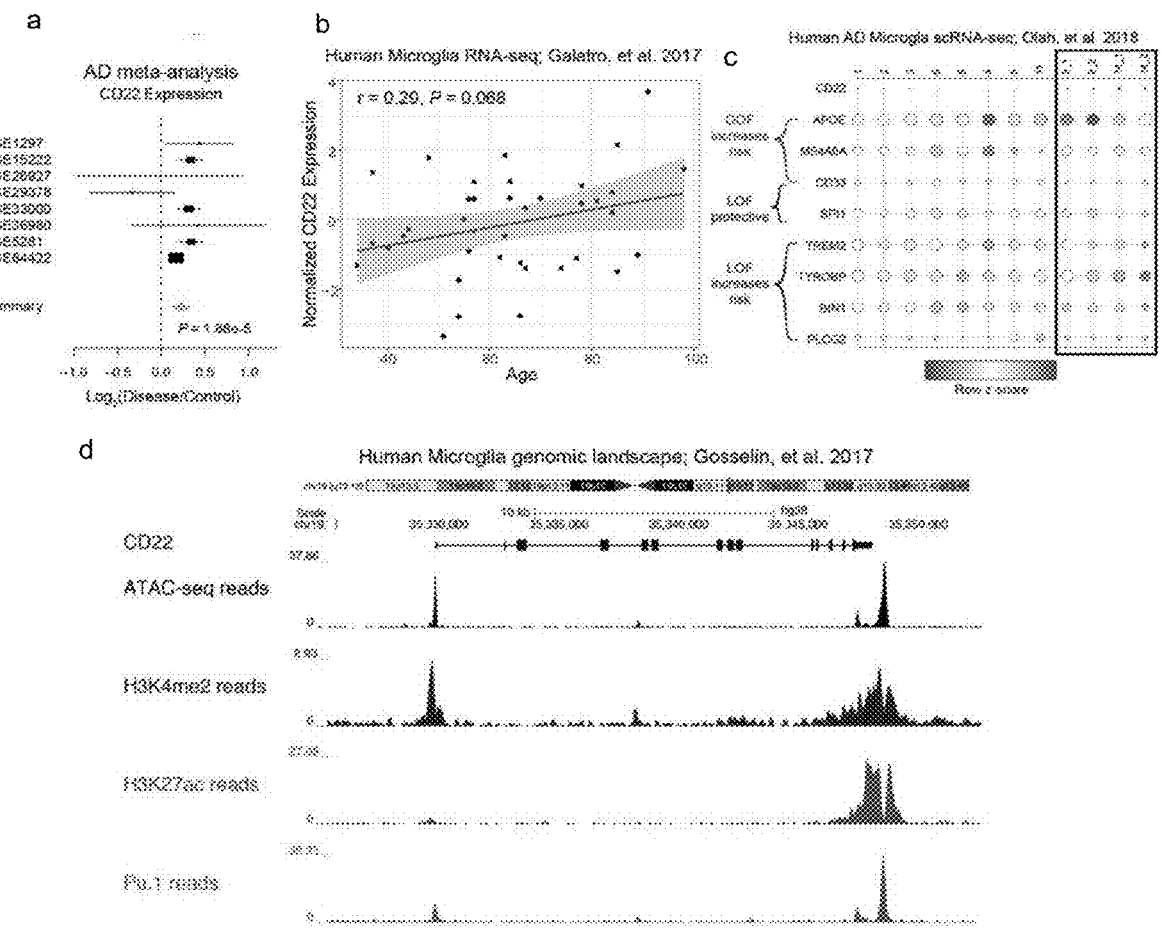
FIG. 39 shows CD22 expression in human microglia and Alzheimer's disease (AD). (a), Forest plot of AD microarray meta-analysis of 8 publicly available NCBI GEO datasets comparing brain tissue from AD patients and age-matched controls. The x axes represent standardized mean difference between disease and control samples, computed as Hedges' g, in log 2 scale. The size of the rectangles is inversely proportional to the standard error. Whiskers represent the 95% confidence interval. The orange diamonds represent overall, combined mean difference of all datasets examined. Width of the diamonds represents the 95% confidence interval of overall mean difference. (b), Correlation of CD22 expression with age in purified human microglia from publicly available RNA-seq dataset (Galatro, et al., 2017) (blue line, linear regression, Spearman correlation). (c), CD22 expression in subpopulations of human microglia. Data from Olah, et al. 2018, scRNA-seq (https://vmenon.shinyapps.io/microglia/). Size of dot represents of the proportion of each cluster expressing a given gene. Clusters 9 and 14 enrich for gain-of-function AD risk genes (e.g., APOE) and de-enrich for loss-of-function AD risk genes (e.g., TREM2). Cluster 14 is correlated with clinical and pathological disease burden. (d), PU.1 binds active cis-regulatory elements of CD22 in human microglia (Data from Gosselin, et al. 2017).

These data indicate that CD22 inhibits phagocytosis via α2-6-linked sialic acid ligand-binding interactions and downstream SHP-1 signaling. CD22 forms nanoclusters with itself and with the sialylated protein tyrosine phosphatase CD45. On B-cells, CD45 positively regulates basal BCR signaling by serving as a cis ligand for CD22, sequestering it away from the BCR[103]. Upon formation of the phagocytic cup and subsequent CD45 exclusion[104], the cytoplasmic ITIMs of CD22 are vulnerable to phosphorylation by Src family kinases downstream of pro-phagocytic receptors, leading to feedback inhibition of phagocytosis. Similar to their dysfunction during normal aging, microglia in the AD brain display signs of impaired phagocytosis, and allelic variants in microglia-specific AD risk genes modify phagocytic function[105-110]. These findings indicate that microglial dysfunction participates in AD pathogenesis and that restoration of homeostatic phagocytosis addresses cognitive decline in AD patients[111]. Accordingly, all publicly available microarray datasets comparing human AD brain tissue to age-matched control tissue were examined[112], and CD22 differential expression across all studies was assessed. A significant upregulation of CD22 is observed in AD patient brains (FIG. 39a). No significant correlation between CD22 expression and age in a previously published RNA-seq dataset of microglia from cognitively normal donors has been observed[113] (FIG. 39b), and one dataset shows CD22 expression in oligodendrocytes[114], a cell-type that acquires phagocytic capabilities in disease[115]. These data indicate that CD22 upregulation in humans is a disease-specific change. Analysis of a single cell atlas of human microglia[116] shows CD22 expression in subpopulations of microglia enriched for AD risk genes, and correlates with clinicopathological decline (FIG. 39c).

The present data complement the established role of microglial immune regulatory genes, TREM2 and CD33, in AD pathogenesis. While TREM2 and CD33 are thought to positively and negatively regulate Aβ phagocytosis respectively, a protein quantitative trait analysis identified crosstalk between the two AD loci wherein the CD33 risk allele leads to increased TREM2 expression, and antibody-based suppression of CD33 reduces TREM2 expression[117]. These data show that long-term CD22 blockade leads to the downregulation of TREM2 and its adaptor TYROBP, and the upregulation of CD33, an indicator of compensatory inhibitory signaling (FIG. 36j). The TREM2 risk variant R47H leads to aberrant glycosylation with increased sialic acid content[118]. CD33 negatively regulates TREM2 signaling via sialic acid interactions, and that CD22 also participates in this regulatory network[119]. In human microglia, all CD22, CD33 and TREM2 genes contain cis-regulatory binding sites for PU.169 (FIG. 39d), a myeloid-lineage master regulator recently implicated in AD risk that modulates the phagocytic capacity of microglia[110]. In addition to AD, CD22 upregulation has been implicated to participate in the pathoeneisis of other diseases in which microglial phagocytosis is impaired. For example, recent studies have found that CD22 is drastically upregulated in mouse models of Niemann Pick Type C120, a neuro-visceral lysosomal storage disease, and ALS[121], a progressive motor neuron disease.

EXPERIMENTAL METHODS

Animals

Aged male C57BL/6 mice (18-24 months old) were obtained from the National Institute on Aging rodent colony. Young male C57BL/6 mice (2-4 months old) were obtained from Jackson Laboratories or Charles River Laboratories. CD22−/− mice were originally generated by L. Nitschke (University of Erlangen) and provided by James Paulson (Scripps Institute) and Romain Ballet and Eugene Butcher (Stanford University). All animal care and procedures complied with the Animal Welfare Act and were in accordance with institutional guidelines and approved by the V. A. Palo Alto Committee on Animal Research and the institutional administrative panel of laboratory animal care at Stanford University.

Cell Culture

BV2 cells were obtained from E. Blasi (Università di Modena e Reggio Emilia) and expanded in DMEM supplemented with 10% FBS, penicillin/streptomycin, and GlutaMAX (Thermo Fisher Scientific). HEK293T cells were cultured in DMEM supplemented with 10% FBS, penicillin/streptomycin, and GlutaMAX. All cells were maintained in a humidified incubator containing 5% CO2 at 37° C.

Flow Cytometry

Antibodies to CD11b (clone M1/70, BioLegend) and CD45 (clone 30-F11, Biolegend) were used for microglia identification (CD11b+CD45lo). For primary microglia immunophenotyping, the following lectins and antibodies were used: biotinylated *Sambucus nigra* agglutinin (SNA, Vector Labs), biotinylated *Maackia amurensis* agglutinins (MAA-1 and MAA-2, Vector), biotinylated *Erythrina cristagalli* lectin (ECL, EY Labs), biotinylated wheat germ agglutinin (WGA, Vector), recombinant mouse Siglec-E (R&D), recombinant mouse Siglec-F (R&D), antibodies to mouse Siglec-1 (clone REA197, Miltenyi Biotec), CD22 (clone OX-97, Biolegend), Siglec-E (clone M1304A01, Biolegend), Siglec-F (clone ES22-10D8, Miltenyi Biotec), Siglec-G (clone SH1, BD Biosciences), Siglec-H (clone 551, Biolegend), CD33 (clone 9A11, eBioscience). For immunostaining, cells were passed through a 100 micron strainer, blocked for 10 minutes on ice with mouse Fc-blocking reagent (BD), and stained for 30 minutes on ice in PBS supplemented with 0.5% bovine serum albumin. When biotinylated antibodies or lectins were used, cells were stained with APC-Cy7-conjugated streptavidin (Biolegend) for 15 minutes on ice following primary stain. When recombinant Siglecs were used, they were precomplexed with APC-Cy7-conjugated anti-human IgG Fc (Biolegend) on ice at 10 micrograms/mL each. The complex was used at 1:2 for a final staining concentration of 5 micrograms/mL. Live cells were identified using Sytox Blue viability dye. Flow cytometry analysis was performed on a BD LSRFortessa and sorting was performed on a BD FACSAria III. Data was analyzed using FlowJo software (TreeStar).

Immunohistochemistry

Mice were euthanized with 2.5% (v/v) Avertin and transcardially perfused with ice-cold HBSS containing glucose and HEPES, or with 4% PFA. Hemibrains were post-fixed in 4% PFA at 4° C. overnight before preservation in 30% sucrose in PBS. Hemibrains were sectioned into 40 micron coronal slices on a microtome and stored in cryoprotective solution at −20° C. Free-floating sections were permeabilized, blocked, and stained overnight at 4° C. with the following primary antibodies at the designated concentrations: goat anti-Iba1 (1:500, ab5076, Abcam), goat anti-Prox1 (1:500, AF2727, R&D), rabbit anti-c-Fos (1:400, 9F6, Cell Signaling), rabbit anti-Aβ (1:200, D54D2, Cell Signaling), rabbit anti-alpha-synuclein (1:200, MJFR1, Abcam), rabbit anti-p-CREB (1:500, 06-519, Millipore), rabbit anti-synaptophysin (1:500, D8F6H, Cell Signaling), rabbit anti-PSD95 (1:500, D27E11, Cell Signaling), rabbit anti-C1q (1:1200, ab182451, Abcam), goat anti-doublecortin (1:500, SC8066, Santa Cruz Biotech), rabbit anti-CD19 (1:500, D4V4B, Cell Signaling), rabbit anti-Tmem119 (1:100, 28-3, Abcam). Sections were washed, stained with Alexa Fluor-conjugated secondary antibodies (1:250), mounted and set under a coverslip before imaging on a confocal laser-scanning microscope (Zeiss LSM880). Thioflavin S staining was performed after secondary antibody staining. Sections were stained in a 0.1% (w/v) solution for 5 minutes, followed by 3 washes in 50% EtOH, and a 30 minute rehydration in diH2O prior to mounting.

Phospho-Western Blot

Protein lysates were prepared by incubating cell pellets on ice in Pierce IP Lysis Buffer or RIPA Lysis Buffer with Complete protease inhibitor cocktail (Thermo Fisher Scientific) and spun at 13,000×g for 10 minutes. The supernatant was collected and protein concentration was measured with the Pierce BCA Protein Assay Kit (Thermo Fisher Scientific). An aliquot containing 5-20 ug of protein from each sample was treated with 5% 2-mercaptoethanol (Sigma-Aldrich) for 5 minutes at 95° C. before being subjected to SDS-PAGE and transferred to a nitrocellulose membrane (Bio-Rad). The membrane was first blocked with Odyssey Blocking Buffer (LI-COR) and stained overnight at 4° C. with primary antibodies at the designated concentrations: mouse anti-α-tubulin (1:10,000, T9026, Sigma), rabbit anti-pSHP-1 (1:5,000, D11G5, Cell Signaling), rabbit anti-Sall1 (1:1000, ab31526, Abcam). The membrane was washed, stained with IRDye conjugated secondary antibodies (1:15,000, LI-COR), and imaged on the Odyssey CLx (LI-COR). The membrane was stripped by incubation with ReBlot Plus Strong Antibody Stripping Solution (Millipore) for 15 minutes before blocking, stained with anti-SHP-1 (1:10,000, C14H6, Cell Signaling) then an IRDye conjugated secondary antibody, and reimaged. Images were analyzed for band intensities with the ImageStudio software (LI-COR).

CRISPR-Cas9 Screen

The 10-sgRNA-per-gene CRISPR/Cas9 deletion library was synthesized, cloned, and infected into Cas9-expressing BV2 cells as previously described[27]. ~12 million (for Membrane Proteins sub-library) or ~24 million (for Drug Targets, Kinases, Phosphatases sub-library) BV2 cells stably expressing EF1alpa-Cas9-BLAST were infected with the 10 guide/gene sgRNA sub-libraries at an MOI<1. Infected cells underwent puromycin selection (1.5 ug/mL) for 5 days after which puromycin was removed and cells were resuspended in normal growth media without puromycin. After selection, sgRNA infection was confirmed by flow cytometry, which indicated >90% of cells expressed the mCherry reporter. Sufficient sgRNA library representation was confirmed by deep sequencing after selection. Cells were cultured and maintained at 1,000× coverage for one week. Phagocytic screening prey were prepared by labeling 3 um amino-coated polystyrene particles (Polysciences) with CypHer5E pH-dependent fluorescent dye (GE Life Sciences). For membrane proteins screen, 12.5 million cells were sorted per replicate (>1000× coverage) with 55.2% in the non-phagocytic gate and 11.2% in the phagocytic gate. For the drug target, kinase, phosphatase screen, 24 million cells were sorted per replicate (>1000× coverage) with 53.1% in the non-phagocytic, and 19.4% in the phagocytic gate. At the end of each screen, genomic DNA was extracted for all populations separately using a QIAGEN Blood Midi Kit. Deep sequencing of sgRNA sequences on an Illumina Nextseq was used to monitor library composition. Guide composition was analyzed and compared to the plasmid library and between conditions using casTLE (https://bitbucket.org/dmorgens/castle). casTLE compares each set of gene-targeting guides to the negative controls, comprising non-targeting and non-genic ("safe-targeting") sgRNAs, which have been shown to more aptly control for on-target toxicity due to endonuclease-induced DNA damage. Enrichment of individual guides was calculated as the log ratio between phagocytic and non-phagocytic populations, and gene-level effects were calculated from t10 guides targeting each gene. P values were calculated by permutating the targeting guides as previously described[39].

In Vitro Phagocytosis Assay

Cells were split into a 24-well plate 24 hours prior to feeding at a density of 50,000 cells/well in serum free medium. Following specific treatments, wells were washed twice with PBS and fed pHrodo-labeled 3 micron amino-coated polystyrene particles (Polysciences) at a ratio of 10 particles per cell. pHrodo labeling was carried out as previously described[37] to minimize background fluorescence. 4 phase and red fluorescent images per well were acquired every hour for 24 hours using the Incucyte S3 live cell analysis system (Essen Bioscience). For each time point, normalized phagocytosis was calculated using the following formula: red object area/phase confluence. To combine data from independent experiments, phagocytosis relative to control was calculated by setting phagocytosis at zero hours in the control condition to 0, and this value at 24 hours to 1. Technical triplicates for each experiment were averaged, and the average of three independent experiments was identified.

Lentivirus Production and Infection

Lentivirus production and infection was performed as previously described[27]. HEK293T cells were transfected with packaging plasmids and sgRNA-containing plasmids. Supernatant was harvested at 48 hours and 72 hours and concentrated with Lenti-X solution (Clontech). BV2 cells stably expressing Cas9 endonuclease under blasticidin (1 ug/mL) selection were spin-infected with lentivirus containing sgRNA plasmids under puromycin selection. Puromycin selection (1.5 ug/mL) was started 48 hours after infection and maintained for 7-14 days. Antibiotic selection was subsequently removed for expansion and freezing. CMAS and CD22 KO ("knock-out") BV2 cells were sub-cloned by single-cell sorting to obtain a monoclonal knockout population. Other single-knockout cell lines were assayed as a polyclonal population.

Sialidase Expression

Sialidase from *Vibrio cholerae* was prepared as previously described[122]. *Escherichia coli* C600 transfected with the pCVD364 vector were grown in 2×YT media supplemented with ampicillin (100 mg/mL) for 12 hours at 37° C. Cells were collected by centrifugation at 4,500×g for 10 minutes. The pellet was resuspended in osmotic shock buffer (20% sucrose, 1 mM EDTA, 30 mM Tris-HCl, pH 8), incubated for 10 min at RT, then spun at 13,000×g for 10 minutes. The pellet was resuspended in ice cold ddH2O, incubated at 4° C. for 10 min, and then spun at 13,000×g. The supernatant was concentrated using a tangential flow filtration system (Pall Corporation). The concentrate was loaded onto a HiTrap Q HP anion exchange column (GE Healthcare Life Sciences) and eluted using a gradient of NaCl in 20 mM Tris, pH 7.6. Fractions containing sialidase were assessed by SDS-PAGE and pooled. Endotoxins were removed using a high capacity endotoxin removal kit (Thermo Fisher Scientific).

Sialic Acid Inhibition

Cells were incubated with 400 nM *Vibrio cholerae* sialidase for 1 hour at 37° C. in serum-free DMEM prior to phagocytosis. $3F_{ax}$-Neu5Ac (R&D) was used as previously described[58]. The inhibitor was used at a concentration of 32 uM serially diluted in DMSO and used at a final concentration of 0.1% DMSO in DMEM. $3F_{ax}$-Neu5Ac was added with serum treatments for 48 hours prior to phagocytosis assays, and replaced in the feeding medium.

Glycopolymer Decoration

Aminooxy glycan-conjugated polymers were based on a poly(methyl vinyl ketone) backbone coupled to a dipalmitoylphosphatidylethanolamine lipid anchor. Glycopolymers were conjugated at 70-85% of ketone sites to either Neu5Ac-α2-3-LacNAc or Neu5Ac-α2-6-LacNAc through oxime chemistry. Cells were decorated with aminooxy glycan-conjugated polymers as previously described[59]. Cells were harvested and resuspended in PBS at 107 cells/mL.

Labeling was carried out by incubating the cell suspension with 1 uM of the specific polymer for 30 minutes at room temperature with constant gentle agitation. Cells were washed with PBS and split into a 24-well plate at 50,000 cells/well for subsequent phagocytosis assays.

Primary Microglia Isolation

Primary mouse microglia were isolated as previously described[123]. Mice were transcardially perfused with ice-cold HBSS containing glucose and HEPES, and brains were removed into the same medium containing DNAse I. On ice, brains were minced with a razor blade and a single cell suspension was obtained by gentle Dounce homogenization. The suspension was filtered through a 100 micron strainer. Myelin was removed using magnetic myelin removal beads (Miltenyi Biotec). The remaining myelin-depleted cell suspension was stained with antibodies to distinguish microglia by flow cytometry. Previous studies show the intense autofluorescent signal of microglia in the aging brain due to the accumulation of the age-related pigment, lipofuscin[22]. To measure expression of proteins on aged microglia by flow cytometry, a gating scheme was used (FIG. 32*f*) to exclude autofluorescent cells (~10% of total microglia) from analysis. Cells with high side-scatter signal which coincided with the autofluorescent population were excluded. Fluorophores with emission spectra in far red channels (e.g., APC-Cy7) were used. This technique supports confident cell-surface profiling of the majority of aged microglia by flow cytometry. For RNA-seq, all microglia including autofluorescent cells were collected.

Quantitative Flow Cytometry

Primary microglia from young and aged mice were isolated as described above. For the same mice, peripheral blood was collected with EDTA anticoagulant by terminal intracardial bleeding. Whole blood was mixed 1:1 with PBS and layered over Ficoll-Paque Plus (GE), spun at 400×g for 30 minutes with no break, and the peripheral blood mononuclear fraction was collected. Microglia and peripheral blood cells were stained with immunophenotyping antibodies as well as PE-conjugated anti-CD22 (Ox97, Biolegend). Quantibrite-PE (BD) beads were resuspended in FACS buffer and analyzed on a BD LSRFortessa. Using shared laser powers and detector voltages, peripheral blood and microglia samples were analyzed for CD22 expression. A standard curve was constructed to correlate PE intensity with number of PE molecules per Quantibrite bead. CD22 molecule numbers on microglia and peripheral blood cells were calculated by interpolation.

Ligand-Binding Assay

Assessment of anti-CD22 on ligand binding was performed as previously described[124]. Recombinant mouse CD22-human Fc fusion protein (R&D) was pre-complexed to an AF647-conjugated anti-human IgG secondary antibody on ice for 30 minutes at equal concentrations (10 ug/mL). The complex was then incubated with various concentrations of a mouse monoclonal anti-CD22 antibody (Cy34, BioXCell) or a mouse IgG1 isotype control antibody (MOPC21, BioXCell) on ice for 30 minutes. Next, the antibody-treated complexes were incubated with WT or sialidase treated BV2 cells for 30 minutes on ice. The cells were washed and rCD22 binding was assessed by flow cytometry on a BD Accuri C6.

Antibody-Mediated Inhibition Assay

WT BV2 cells were incubated in serum-free DMEM containing varying concentrations of a monoclonal anti-CD22 antibody (Cy34, BioXCell) from 20 ug/mL to 0 ug/mL for 8 hours at 37° C. The p-SHP-1:total SHP-1 ratio, indicative of signaling activity downstream of CD22, was determined by phospho-western blot as previously described.

Antibody Internalization Assay

WT BV2 cells were split into a 24-well plate 24 hours prior to antibody treatment at a density of 50,000 cells/well. Cells were treated with rat anti-mouse CD16/CD32 Fc Blocker (2.4G2, BD) then incubated with the following antibodies at 1 ug/mL: mouse IgG1 isotype control antibody (MOPC21, BioXCell), mouse anti-CD22 (Cy34, BioXCell) and rat anti-CD22 (OX-96, Bio-Rad). All antibodies were pre-labeled with Incucyte FabFluor-pH Red (Essen Bioscience) according to the manufacturer's protocol. 9 phase and red fluorescent images per well were acquired every hour for 24 hours using the Incucyte S3 live cell analysis system (Essen Bioscience). For each time point, antibody internalization was calculated using the following formula: red object area/phase confluence. Technical triplicates for each experiment were averaged.

In Vivo Phagocytosis Assay

CypHer5E and AlexaFluor555 double-labeled myelin (25 mg/mL), CypHer5E-labeled Aβ oligomers (1 mg/mL), or CypHer5E-labeled alpha-synuclein fibrils (1 mg/mL) were mixed with a mouse IgG1 isotype control antibody (MOPC21, BioXCell, 1 mg/mL) or anti-CD22 (Cy34, BioXCell, 1 mg/mL), and injected into opposite hemispheres of aged mice using a stereotaxic apparatus (Kopf instruments). Mice were anesthetized using isoflurane, their skulls were exposed, and a hole was drilled at the injection site using aseptic technique. One microliter of the antibody/phagocytic target material mixture was injected at +/−2 mm lateral, 0 mm anterior-posterior, and −1.5 mm deep relative to the intersection of the coronal and sagittal suture (bregma) at a rate of 200 nL/minute. The needle was left in place for an additional 3 minutes to allow for diffusion, then slowly withdrawn. Mice received post-surgical buprenorphine and baytril for pain and infection prevention, respectively. After 48 hours, mice were anesthetized and transcardially perfused with 4% PFA. The injection site was sectioned, stained, and imaged as described above, and 6-8 consecutive sections, spaced 40 um apart, were quantified to test total target clearance over the entire area of the injection site. Sections at the margins of the injection site without noticeable Iba1+ microgliosis, which takes >48 hours to resolve and is not influenced by treatment, were excluded.

Ex Vivo Microglial Phagocytosis Assay

Whole brain myelin-depleted single-cell suspensions were prepared as described above. Next, a rough estimation of microglia counts from each brain was determined by strictly gating a volume-designated aliquot of the suspensions by forward scatter/side scatter on a flow cytometer (BD Accuri C6). Each suspension was adjusted to contain equal microglia per unit volume. Then, single cell brain suspensions were treated accordingly for 1 hour in serum free DMEM-F12 at 37° C. with periodic agitation. Treatments were washed out and cells were resuspended in FACS buffer containing pHrodo- or CypHer5E-conjugated particles at a ratio of 50 particles per microglia. The cell-particle mixture was incubated for 1-2 hours at 37° C. with periodic agitation. Phagocytosis was stopped by transferring the suspensions to ice, where the cells were stained with antibodies to distinguish microglia. Microglial phagocytosis was assessed by flow cytometry by pre-gating live CD11b+ CD45lo cells and assessing pH-dependent particle fluorescence within this population. The eating gate was determined using an unfed control, and confirmed by sorting an aliquot of the sample into non-eating and eating populations by FACS followed by microscopic assessment.

Ex Vivo Microglia Secretome Profiling

Microglia from aged (20-24 m.o.) mice were isolated as described above, with minor modifications. Following myelin depletion, cells were incubated with CD11b-positive enrichment beads (Miltenyi), isolated by magnetic selection using LS-columns, and plated at 30,000 cells/well of a 96-well plate. Microglia were maintained in serum-free defined medium as previously described[37], and treated with either IgG (MOPC21, BioXCell, 20 ug/mL) or anti-CD22 (Cy34, BioXCell, 20 ug/mL) in the presence or absence of Aβ oligomers (5 uM) for 8 hours. Following incubation, supernatant was collected, spun down to remove cells, and flash frozen on dry ice. A bead-based immunoassay for mouse cytokines and chemokines (Eve Technologies) was used for protein detection.

RNA-Sequencing and Analysis 10,000 microglia were isolated from either hemibrains or dissected hippocampi as described above, and sorted into RLT buffer (Qiagen) containing beta-mercaptoethanol. RNA was extracted using a RNeasy Micro Plus kit (Qiagen) according the manufacturer's protocol. RNA integrity was assessed on a Bioanalyzer (Agilent), and high-quality samples were used for library preparation. cDNA synthesis and amplification were performed using the SmartSeq v4 Ultra-low input kit (Takara), and libraries were tagmented, adaptor ligated, and indexed using the Nextera XT kit (Illumina). After normalization and pooling, libraries were sequenced on a Hiseq 4000 (Illumina) using paired-end 100 bp reads. Libraries were sequenced to a depth of >30 million reads per sample. Raw sequencing files were demultiplexed with bcl2fastq, reads were aligned using STAR, the count matrix was generated using SummarizedExperiment, and differential expression analysis was performed using DESeq2 with standard settings.

RNAScope In Situ Hybridization

RNA in situ hybridization was performed on fresh frozen brain tissue using the Multiplex Fluorescence v2 kit (Advanced Cell Diagnostics) according to the manufacturer's protocol. Probes for CD22 and Tmem119 were obtained from the manufacturer.

Osmotic Pump Intracerebroventricular Delivery of Anti-CD22

A monoclonal anti-CD22 antibody (Cy34, BioXCell, 1 mg/mL) or mouse IgG1 isotype control antibody (MOPC21, BioXCell, 1 mg/mL) were conjugated to AlexaFluor647 (ThermoFisher) using NHS chemistry at a dye:protein molar ratio of 4. Free dye was removed, and buffer was exchanged with artificial CSF (Tocris) using 40 kD MWCO Zeba spin desalting columns (ThermoFisher). The labeled antibodies were loaded into 200 microliter osmotic pumps (Alzet/Durect) with a 28-day infusion rate of 0.25 mL per hour. Based on the clearance rate of immunoglobulin from the cerebrospinal fluid[125] (CSF) in rodents, this infusion rate was chosen to maintain a steady state concentration of 10 micrograms/mL, a dose shown to promote phagocytosis with this particular antibody ex vivo. Osmotic pumps were connected to a cannula (Brain infusion kit III, Alzet) inserted at +1 mm lateral, −0.3 mm anterior-posterior, and −3 mm deep relative to bregma in order to target the right lateral ventricle. The pump was placed subcutaneously, and mice received post-surgical buprenorphine and Baytril.

Quantification of Antibody Leakage into the Periphery Following Intracerebroventricular Administration.

1 mg of CD22 antibody was incubated with 30× molar ratio of Trans-Cyclooctene-NHS ester (Click Chemistry Tools) overnight at 4° C. before being quenched with 1M Tris pH 8.0 and desalted (Zeba, 40K MWCO, Thermo). Mice were administered unlabeled or Trans-Cyclooctene (TCO)-labeled CD22 antibody via osmotic pump intracerebroventricularly as detailed above, or with equimolar amounts intravenously (retro-orbital) or intraperitoneally. Seven days later, blood was collected with EDTA anticoagulant by terminal intracardial bleeding. EDTA-plasma was isolated by centrifugation at 1,000 g for 15 min at 4° C. before aliquoting, flash freezing, and storage at −80° C. Protein concentrations of plasma samples and unlabeled and TCO-labeled CD22 antibodies were measured with a BCA Protein Assay Kit (Pierce). 75 ug of plasma was aliquoted, denatured in 1% SDS, and incubated for 90 minutes in the dark at room temperature with 6 uM SiR-tetrazine (Spirochrome) for subsequent click chemistry detection by in-gel fluorescence. 10× decreasing amounts of unlabeled and TCO-labeled CD22 antibody—from 1 ng to 0.1 ng—were processed similarly as a fluorescence standard. A 4× stock solution of NuPAGE LDS (Thermo) was added to each sample before heating at 95° C. for 5 minutes. Proteins were briefly spun and separated by electrophoresis in 12% Bis-Tris polyacrylamide gels (Invitrogen). Gels were washed twice in distilled water for 15 minutes before SiR imaging in the 700-nm channel of an Odyssey CLx (LI-COR). To ensure accurate protein loading, gels were incubated with GelCode Blue Stain Reagent (Thermo) overnight before destaining in distilled water for at least 3 hours and imaged in the 800-nm channel of an Odyssey CLx (LI-COR). CD22 fluorescence signals were quantified in accompanying Image Studio™ software (LI-COR).

Behavioral Assays

The forced alternation Y-maze test was performed as previously described with minor alterations[126]. The test consisted of a 5-minute training trial followed by a 5 minute retrieval trail, with a 1 hour inter-trial interval. For the training trial, one arm of the Y-maze was blocked off, and mice were allowed to explore the two open arms. One hour later, the mouse was again placed in the Y-maze with all three arms open, and a black and white pattern placed at the end of the novel arm. Between mice and trials, the maze was wiped with ethanol to remove odor cues. For analysis, video images were analyzed by a blinded observer, and both the number of arm entries and the time spent in each arm was quantified. Mice with less than 2 arm entries in the first minute of the retrieval trial were excluded from the analysis.

The fear-conditioning paradigm was performed as previously described[92]. Mice were trained to associate cage context or an audiovisual cue with an aversive stimulus (foot-shock). The test was administered over two days. On day 1, mice were placed in a cage and exposed to two periods of 30s of paired cue light and 1,000-Hz tone followed by a 2-s foot shock (0.6 mA), with a 180-s interval. On day 2, mice were subjected to two trials. In the first trial assessing contextual memory, mice were re-exposed to the same cage context, and freezing behavior was measured during minute 1-3 using a FreezeScan tracking system (Cleversys). In the second trial measuring cued memory, mice were placed in a novel context and exposed to the same cue light and tone from day 1 after 2 minutes of exploration. Freezing behavior was measured for 1-3 minutes following the cue.

Gene Ontology Analysis

For gene ontology analysis of CRISPR-Cas9 screen hits, Panther was used to test statistical overrepresentation of hits in the Reactome pathway database given a reference list containing all genes targeted by the sgRNA library. For analysis of RNA-seq data, Enrichr was used to test enrichment of significantly up- or down-regulated genes in KEGG, BioCarta, WikiPathways, and Reactome databases. Pre-ranked gene set enrichment analysis was performed using GSEA software v3 (Broad Institute) with default settings and signed log-normalized p-values as a ranking metric.

Meta-Analysis of Gene Expression Data

Microarray meta-analysis was performed with publicly available data. Microarray gene expression datasets were downloaded from the NCBI GEO comprising samples from patients diagnosed with spontaneous late onset AD or PD. All gene expression was normalized and log 2 transformed. For each study, the sample phenotypes as defined by the primary publication of a source study were used. Samples were excluded if the diagnosis of AD was designated as uncertain. Microarray probes in each dataset were mapped to Entrez Gene identifiers (IDs) to facilitate integrated analysis. If a probe matched more than one gene, the expression data for that probe were expanded to add one record for each mapped gene (Ramasamy et al., 2008). We then applied a multicohort gene expression analysis strategy. We estimated the effect size for each gene in each dataset as Hedges' adjusted g. If multiple probes mapped to a gene, the effect size for each gene was summarized via the fixed effect inverse-variance model.

Preparation of Fluorescent Phagocytic Material

Purified CNS myelin was isolated as previously described[127]. Mice were euthanized and their brains homogenized. Crude brain homogenate was subjected to a series of sucrose gradients under ultracentrifugation followed by osmotic shocks in hypotonic buffers to remove myelin sheaths from severed axons. Aβ oligomers were prepared as previously described[128]. $A\beta_{1-42}$ (Anaspec) was treated with hexafluoroisopropanol (HFIP) to achieve a monomeric solution. Oligomerization was induced by diluting a 5 mM monomeric Aβ DMSO stock to 200 uM in ice-cold PBS and incubated overnight at 4 degrees. Phagocytic material was conjugated to fluorescent dyes as previously described[37]. For double-labeled myelin, 50 mg/mL of myelin prep was incubated with equimolar concentrations of AlexaFluor555-NHS ester and CypHer5E-NHS ester in PBS with 0.1M sodium bicarbonate for 45 minutes at room temperature. Myelin was washed 4 times with PBS and centrifugation to remove free dye. For Aβ and α-synuclein, 100 uL of the 200 uM protein aggregates were incubated with 4 uL CypHer5E-NHS ester in PBS with 0.1M sodium bicarbonate for 30 minutes at room temperature. Free dye was removed using BioSpin Micro P-6 desalting columns (BioRad).

qPCR

Microglia were isolated by flow activated cell sorting (FACS) as described above, and sorted into Trizol LS. RNA was prepared by chloroform-phenol extraction, treated with RNase-free DNase, and purified with Qiagen RNeasy Min-Elute columns. RNA quality was assessed by Bioanalyzer RNA integrity number quantification (Agilent Technologies). cDNA synthesis and amplification was performed with a SMART-seq V4 Ultra-Low Input RNA Kit (Clontech). Samples were diluted and mixed with SYBR green master mix before loading as technical triplicates for qPCR on a LightCycler 480 (Roche). ΔΔCT values normalized to b-actin were used to test relative gene expression between samples. The following validated primer pairs for murine CD22 were used: 5'-CCA CTC CTC AGG CCA GAA ACT-3' (forward) and 5'-TGC CGA TGG TCT CTG GAC TG-3' (reverse).

REFERENCES

1. Aguzzi, A., Barres, B. A., and Bennett, M. L. (2013). Microglia: scapegoat, saboteur, or something else? Science 339, 156-161.

2. Arandjelovic, S., and Ravichandran, K. S. (2015). Phagocytosis of apoptotic cells in homeostasis. Nat Immunol 16, 907-917.
3. Ransohoff, R. M., and El Khoury, J. (2015). Microglia in Health and Disease. Cold Spring Harb Prospect Biot 8, a020560-16.
4. Fourgeaud, L., Través, P. G., Tufail, Y., Leal-Bailey, H., Lew, E. D., Burrola, P. G., Callaway, P., Zagórska, A., Rothlin, C. V., Nimmerjahn, A., et al. TAM receptors regulate multiple features of microglial physiology. Nature 532, 240EP-.
5. Salter, M. W., and Stevens, B. (2017). Microglia emerge as central players in brain disease. Nature Medicine 23, 1018-1027.
6. Fuger, P., Hefendehl, J. K., Veeraraghavalu, K., Wendeln, A.-C., Schlosser, C., Obermüller, U., Wegenast-Braun, B. M., Neher, J. J., Martus, P., Kohsaka, S., et al. (2017). Microglia turnover with aging and in an Alzheimer's model via long-term in vivo single-cell imaging. Nat Neurosci 20, 1371-1376.
7. Réu, P., Khosravi, A., Bernard, S., Mold, J. E., Salehpour, M., Alkass, K., Perl, S., Tisdale, J., Possnert, G., Druid, H., et al. (2017). The Lifespan and Turnover of Microglia in the Human Brain. CellReports 20, 779-784.
8. Nimmerjahn, A., Kirchhoff, F., and Helmchen, F. (2005). Resting microglial cells are highly dynamic surveillants of brain parenchyma in vivo. Science 308, 1314-1318.
9. Davalos, D., Grutzendler, J., Yang, G., Kim, J. V., Zuo, Y., Jung, S., Littman, D. R., Dustin, M. L., and Gan, W.-B. (2005). ATP mediates rapid microglial response to local brain injury in vivo. Nat Neurosci 8, 752-758.
10. Tremblay, M. E., Lowery, R. L. & Majewska, A. K. Microglial interactions with synapses are modulated by visual experience. PLoS Biol. 8, e1000527 (2010).
11. Schafer, D. P. et al. Microglia sculpt postnatal neural circuits in an activity and complement-dependent manner. Neuron 74, 691-705 (2012).
12. Paolicelli, R. C. et al. Synaptic pruning by microglia is necessary for normal brain development. Science 333, 1456-1458 (2011).
13. Hong, S. et al. Complement and microglia mediate early synapse loss in Alzheimer mouse models. Science 352, 712-716 (2016).
14. Stephan, A. H., Barres, B. A. & Stevens, B. The complement system: an unexpected role in synaptic pruning during development and disease. Annu. Rev. Neurosci. 35, 369-389 (2012).
15. Williams, P. A. et al. Inhibition of the classical pathway of the complement cascade prevents early dendritic and synaptic degeneration in glaucoma. Mol. Neurodegener. 11, 26 (2016).
16. Lui, H., Zhang, J., Makinson, S. R., Cahill, M. K., Kelley, K. W., Huang, H.-Y., Shang, Y., Oldham, M. C., Martens, L. H., Gao, F., et al. (2016). Progranulin Deficiency Promotes Circuit-Specific Synaptic Pruning by Microglia via Complement Activation. Cell 165, 921-935.
17. Safaiyan, S., Kannaiyan, N., Snaidero, N., Brioschi, S., Biber, K., Yona, S., Edinger, A. L., Jung, S., Rossner, M. J., and Simons, M. (2016). Age-related myelin degradation burdens the clearance function of microglia during aging. Nature Neuroscience 19, 995-998.
18. Deczkowska, A., Amit, I., and Schwartz, M. (2018). Microglial immune checkpoint mechanisms. Nature Publishing Group 21, 779-786.
19. Hefendehl, J. K., Neher, J. J., Sühs, R. B., Kohsaka, S., Skodras, A., and Jucker, M. (2013). Homeostatic and injury-induced microglia behavior in the aging brain. Aging Cell 13, 60-69.
20. Vaughan, D. W. and Peters, A. (1974). Neuroglial cells in the cerebral cortex of rats from young adulthood to old age: an electron microscope study. J Neurocytol. 3, 405-429.
21. Tremblay, M.-È., Zettel, M. L., Ison, J. R., Allen, P. D., and Majewska, A. K. (2012). Effects of aging and sensory loss on glial cells in mouse visual and auditory cortices. Glia 60, 541-558.
22. Sierra, A., Gottfried-Blackmore, A. C., McEwen, B. S., and Bulloch, K. (2007). Microglia derived from aging mice exhibit an altered inflammatory profile. Glia 55, 412-424.
23. Mosher, K. I., and Wyss-Coray, T. (2014). Microglial dysfunction in brain aging and Alzheimer's disease. Alzheimer's Disease—Amyloid, Tau and Beyond 88, 594-604.
24. Hickman, S. E., Kingery, N. D., Ohsumi, T. K., Borowsky, M. L., Wang, L.-C., Means, T. K., and Khoury, El, J. The microglial sensome revealed by direct RNA sequencing. Nat Neurosci 16, 1896EP-.
25. Grabert, K., Michoel, T., Karavolos, M. H., Clohisey, S., Baillie, J. K., Stevens, M. P., Freeman, T. C., Summers, K. M., and McColl, B. W. Microglial brain region-dependent diversity and selective regional sensitivities to aging. Nat Neurosci 19, 504EP-.
26. Kang, S. S., Ebbert, M. T. W., Baker, K. E., Cook, C., Wang, X., Sens, J. P., Kocher, J.-P., Petrucelli, L., and Fryer, J. D. (2018). Microglial translational profiling reveals a convergent APOE pathway from aging, amyloid, and tau. J Exp Med jem.20180653-11.
27. Deans, R. M., Morgens, D. W., Ökesli, A., Pillay, S., Horlbeck, M. A., Kampmann, M., Gilbert, L. A., Li, A., Mateo, R., Smith, M., Glenn, J. S., Carette, J. E., Khosla, C., and Bassik, M. C. (2016). Parallel shRNA and CRISPR-Cas9 screens enable antiviral drug target identification. Nature Chemical Biology 12, 361-366.
28. Morgens, D. W., Wainberg, M., Boyle, E. A., Ursu, O., Araya, C. L., Tsui, C. K., Haney, M. S., Hess, G. T., Han, K., Jeng, E. E., et al. (2017). Genome-scale measurement of off-target activity using Cas9 toxicity in high-throughput screens. Nature Communications 8, 1-8.
29. Kramer, N. J., Haney, M. S., Morgens, D. W., Jovičić, A., Couthouis, J., Li, A., Ousey, J., Ma, R., Bieri, G., Tsui, C. K., et al. (2018). CRISPR-Cas9 screens in human cells and primary neurons identify modifiers of C9ORF72 dipeptide-repeat-protein toxicity. Nature Genetics 1-14.
30. Koike-Yusa, H., Li, Y., Tan, E. P., Velasco-Herrera Mdel, C., and Yusa, K. (2014). Genome-wide recessive genetic screening in mammalian cells with a lentiviral CRISPR-guide RNA library. Nat Biotechnol 32, 267-273.
31. Shalem, O., Sanjana, N. E., Hartenian, E., Shi, X., Scott, D. A., Mikkelson, T., Heckl, D., Ebert, B. L., Root, D. E., Doench, J. G., et al. (2014). Genome-scale CRISPR-Cas9 knockout screening in human cells. Science 343, 84-87.
32. Shalem, O., Sanjana, N. E. and Zhang, F (2015). High-throughput functional genomics using CRISPR-Cas9 Nature Reviews Genetics 16, 299-311.
33. Wang, T., Wei, J. J., Sabatini, D. M., and Lander, E. S. (2014). Genetic screens in human cells using the CRISPR-Cas9 system. Science 343, 80-84.

34. Zhou, Y., Zhu, S., Cai, C., Yuan, P., Li, C., Huang, Y., and Wei, W. (2014). High-throughput screening of a CRISPR/Cas9 library for functional genomics in human cells. Nature 509, 487-491.
35. Blasi, E., Barluzzi, R., Bocchini, V., Mazzolla, R., and Bistoni, F. (1990). Immortalization of murine microglial cells by a v-raf/v-myc carrying retrovirus. Journal of Neuroimmunology 27, 229-237.
36. Bohlen, C. J., Bennett, F. C., and Bennett, M. L. (2018). Isolation and Culture of Microglia. Current Protocols in Immunology 339, e70-21.
37. Bohlen, C. J., Bennett, F. C., Tucker, A. F., Collins, H. Y., Mulinyawe, S. B., and Ben A Barres (2017). Diverse Requirements for Microglial Survival, Specification, and Function Revealed by Defined-Medium Cultures. Neuron 94, 759-773.e8.
38. Butovsky, O., Jedrychowski, M. P., Moore, C. S., Cialic, R., Lanser, A. J., Gabriely, G., Koeglsperger, T., Dake, B., Wu, P. M., Doykan, C. E., et al. Identification of a unique TGF-β-dependent molecular and functional signature in microglia. Nat Neurosci 17, 131EP-.
39. Morgens, D. W., Deans, R. M., Li, A., and Bassik, M. C. (2016). Systematic comparison of CRISPR/Cas9 and RNAi screens for essential genes. Nature Biotechnology 34, 634-636.
40. Burke, S. N. & Barnes, C. A. Neural plasticity in the ageing brain. Nature Rev. Neurosci. 7, 30-40 (2006).
41. Verbitsky, M. et al. Altered hippocampal transcript profile accompanies an age-related spatial memory deficit in mice. Learn. Mem. 11, 253-260 (2004).
42. Lund, P. K. et al. Transcriptional mechanisms of hippocampal aging. Exp. Gerontol. 39, 1613-1622 (2004).
43. Lee, C. K., Weindruch, R. and Prolla, T. A. Gene-expression profile of the ageing brain in mice. Nature Genet. 25, 294-297 (2000).
44. Müller, J., and Nitschke, L. (2014). The role of CD22 and Siglec-G in B-cell tolerance and autoimmune disease. Nature Publishing Group 10, 422-428.
45. Macauley, M. S., Crocker, P. R., and Paulson, J. C. (2014). Siglec-mediated regulation of immune cell function in disease. Nat Rev Immunol 14, 653-666.
46. Nitschke, L., Carsetti, R., Ocker, B., Köhler, G. and Lamers, M. C. CD22 is a negative regulator of B-cell receptor signalling. Curr. Biol. 7, 133-143 (1997).
47. Li, Y.-Q., Zhang, J., Li, J., and Sun, L. (2017). First characterization of fish CD22: An inhibitory role in the activation of peripheral blood leukocytes. Veterinary Immunology and Immunopathology 190, 39-44.
48. Li, Y.-Q., Sun, L., and Li, J. (2018). Macropinocytosis-dependent endocytosis of Japanese flounder IgM+ B cells and its regulation by CD22. Fish and Shellfish Immunology 84, 138-147.
49. Linnartz-Gerlach, B., Kopatz, J., and Neumann, H. (2014). Siglec functions of microglia. Glycobiology 24, 794-799.
50. Griciuc, A., Serrano-Pozo, A., Parrado, A. R., Lesinski, A. N., Asselin, C. N., Mullin, K., Hooli, B., Choi, S. H., Hyman, B. T., and Tanzi, R. E. (2013). Alzheimer's Disease Risk Gene CD33 Inhibits Microglial Uptake of Amyloid Beta. Neuron 78, 631-643.
51. Bennett, M. L., Bennett, F. C., Liddelow, S. A., Ajami, B., Zamanian, J. L., Fernhoff, N. B., Mulinyawe, S. B., Bohlen, C. J., Adil, A., Tucker, A., et al. (2016). New tools for studying microglia in the mouse and human CNS. Proc Natl Acad Sci USA 113, E1738-E1746.
52. Zhang, Y., Chen, K., Sloan, S. A., Bennett, M. L., Scholze, A. R., O'Keeffe, S., Phatnani, H. P., Guarnieri, P., Caneda, C., Ruderisch, N., et al. (2014). An RNA-Sequencing Transcriptome and Splicing Database of Glia, Neurons, and Vascular Cells of the Cerebral Cortex. Journal of Neuroscience 34, 11929-11947.
53. Benilova, I., Karran, E., and De Strooper, B. (2012). The toxic Aβ oligomer and Alzheimer's disease: an emperor in need of clothes. Nature Publishing Group 15, 349-357.
54. Abeliovich, A. and Gitler, A. D. (2016). Defects in trafficking bridge Parkinson's disease pathology and genetics. Nature 539, 207-216.
55. Müller, J., Obermeier, I., Wöhner, M., Brandi, C., Mrotzek, S., Angermüller, S., Maity, P. C., Reth, M., and Nitschke, L. (2013). CD22 ligand-binding and signaling domains reciprocally regulate B-cell Ca2+ signaling. Proc. Natl. Acad. Sci. U.S.a. 110, 12402-12407.
56. Seyrantepe, V., Iannello, A., Liang, F., Kanshin, E., Jayanth, P., Samarani, S., Szewczuk, M. R., Ahmad, A., and Pshezhetsky, A. V. (2009). Regulation of Phagocytosis in Macrophages by Neuraminidase 1. J. Biol. Chem. 285, 206-215.57.
57. Cabral, M. G., Silva, Z., Ligeiro, D., Seixas, E., Crespo, H., Carrascal, M. A., Silva, M., Piteira, A. R., Paixão, P., Lau, J. T., et al. (2013). The phagocytic capacity and immunological potency of human dendritic cells is improved by α2,6-sialic acid deficiency. Immunology 138, 235-245.
58. Rillahan, C. D., Antonopoulos, A., Lefort, C. T., Sonon, R., Azadi, P., Ley, K., Dell, A., Haslam, S. M., and Paulson, J. C. (2012). Global metabolic inhibitors of sialyl- and fucosyltransferases remodel the glycome. Nat Chem Biol 8, 662-669.
59. Hudak, J. E., Canham, S. M., and Bertozzi, C. R. (2013). Glycocalyx engineering reveals a Siglec-based mechanism for NK cell immunoevasion. Nat Chem Biol 10, 69-75.
60. Ereño-Orbea, J., Sicard, T., Cui, H., Mazhab-Jafari, M. T., Benlekbir, S., Guarné, A., Rubinstein, J. L., and Julien, J.-P. (2017). Molecular basis of human CD22 function and therapeutic targeting. Nature Communications 1-11.
61. Linnartz, B., Wang, Y., and Neumann, H. (2010). Microglial Immunoreceptor Tyrosine-Based Activation and Inhibition Motif Signaling in Neuroinflammation. International Journal of Alzheimer's Disease 2010, 1-
62. Han, S., Collins, B. E., Bengtson, P., and Paulson, J. C. (2005). Homomultimeric complexes of CD22 in B cells revealed by protein-glycan cross-linking. Nat Chem Biol 1, 93-97.
63. Hibbs, M. L., Harder, K. W., Armes, J., Kountouri, N., Quilici, C., Casagranda, F., Dunn, A. R., and Tarlinton, D. M. (2002). Sustained activation of Lyn tyrosine kinase in vivo leads to autoimmunity. J Exp Med 196, 1593-1604.
64. Kant, A. M., De, P., Peng, X., Yi, T., Rawlings, D. J., Kim, J. S., and Durden, D. L. (2002). SHP-1 regulates Fcγ receptor-mediated phagocytosis and the activation of RAC. Blood 100, 1852.
65. Gomez, C. P., Tiemi Shio, M., Duplay, P., Olivier, M., and Descoteaux, A. (2012). The Protein Tyrosine Phosphatase SHP-1 Regulates Phagolysosome Biogenesis. The Journal of Immunology 189, 2203-2210.
66. Deczkowska, A., Keren-Shaul, H., Weiner, A., Colonna, M., Schwartz, M., and Amit, I. (2018). Disease-Associated Microglia: A Universal Immune Sensor of Neurodegeneration. Cell 173, 1073-1081.
67. Deczkowska, A., Matcovitch-Natan, O., Tsitsou-Kampeli, A., Ben-Hamo, S., Dvir-Szternfeld, R., Spinrad, A., Singer, O., David, E., Winter, D. R., Smith, L. K., et al. (2017). Mef2C restrains microglial inflammatory 68. Wang, Y., Cella, M., Mallinson, K., Ulrich, J. D., Young, K. L., Robinette, M. L., Gilfillan, S., Krishnan, G. M., Sudhakar, S., Zinselmeyer, B. H., et al. (2015). TREM2 Lipid Sensing Sustains the Microglial Response in an Alzheimer's Disease Model. Cell 160, 1061-1071.
69. Gosselin, D., Link, V. M., Romanoski, C. E., Fonseca, G. J., Eichenfield, D. Z., Spann, N. J., Stender, J. D., Chun, H. B., Garner, H., Geissmann, F., et al. (2014). Environment Drives Selection and Function of Enhancers Controlling Tissue-Specific Macrophage Identities. Cell 159, 1327-1340.
70. Qin, Y., Garrison, B. S., Ma, W., Wang, R., Jiang, A., Li, J., Mistry, M., Bronson, R. T., Santoro, D., Franco, C., et al. (2018). A Milieu Molecule for TGF-β Required for Microglia Function in the Nervous System. Cell 174, 156-171.e16.
71. Wyss-Coray, T., Lin, C., Yan, F., Yu, G.-Q., Rohde, M., McConlogue, L., Masliah, E., and Mucke, L. TGF-β1 promotes microglial amyloid-β clearance and reduces plaque burden in transgenic mice. Nature Medicine 7, 612EP31.
72. Matcovitch-Natan, O., Winter, D. R., Giladi, A., Vargas Aguilar, S., Spinrad, A., Sarrazin, S., Ben-Yehuda, H., David, E., Zelada González, F., Perrin, P., et al. (2016). Microglia development follows a stepwise program to regulate brain homeostasis. Science 353, aad8670-aad8670.
73. Buttgereit, A., Lelios, I., Yu, X., Vrohlings, M., Krakoski, N. R., Gautier, E. L., Nishinakamura, R., Becher, B., and Greter, M. (2016). Sall1 is a transcriptional regulator defining microglia identity and function. Nat. Immunol. 1-11.
74. Holtman, I. R., Raj, D. D., Miller, J. A., Schaafsma, W., Yin, Z., Brouwer, N., Wes, P. D., Möller, T., One, M., Kamphuis, W., et al. (2015). Induction of a common microglia gene expression signature by aging and neurodegenerative conditions: a co-expression meta-analysis. Acta Neuropathol Commun 3, 31.
75. Keren-Shaul, H., Spinrad, A., Weiner, A., Matcovitch-Natan, O., Dvir-Szternfeld, R., Ulland, T. K., David, E., Baruch, K., Lara-Astaiso, D., Toth, B., et al. (2017). A Unique Microglia Type Associated with Restricting Development of Alzheimer's Disease. Cell 1-33.
76. Krasemann, S., Madore, C., Cialic, R., Baufeld, C., Calcagno, N., Fatimy, El, R., Beckers, L., O'Loughlin, E., Xu, Y., Fanek, Z., et al. (2017). The TREM2-APOE Pathway Drives the Transcriptional Phenotype of Dysfunctional Microglia in Neurodegenerative Diseases. Immunity 47, 566-581.e569.
77. Dupont, A.-C., Largeau, B., Santiago Ribeiro, M., Guilloteau, D., Tronel, C., and Arlicot, N. (2017). Translocator Protein-18 kDa (TSPO) Positron Emission Tomography (PET) Imaging and Its Clinical Impact in Neurodegenerative Diseases. International Journal of Molecular Sciences 18, 785-37.
78. Holtman, I. R., Raj, D. D., Miller, J. A., Schaafsma, W., Yin, Z., Brouwer, N., Wes, P. D., Möller, T., One, M., Kamphuis, W., et al. (2015). Induction of a common microglia gene expression signature by aging and neurodegenerative conditions: a co-expression meta-analysis. Acta Neuropathol Commun 3, 31.
79. Marciniak, E., Faivre, D., Dutar, P., Pires, C. A., Demeyer, D., Caillierez, R., Laloux, C., Buée, L., Blum, D., and Humez, S. (2015). The Chemokine MIP-1α/ CCL3 impairs mouse hippocampal synaptic transmission, plasticity and memory. Nature Publishing Group 1-11.
80. Liu, Y., Beyer, A., and Aebersold, R. (2016). On the Dependency of Cellular Protein Levels on mRNA Abundance. Cell 165, 535-550.
81. Mott, R. T., Ait-Ghezala, G., Town, T., Mori, T., Vendrame, M., Zeng, J., Ehrhart, J., Mullan, M., and Tan, J. (2004). Neuronal expression of CD22: Novel mechanism for inhibiting microglial proinflammatory cytokine production. Glia 46, 369-379.
82. Heneka, M. T., McManus, R. M., and Latz, E. (2018). Inflammasome signalling in brain function and neurodegenerative disease. Nature Reviews Neuroscience 19, 610-621.
83. Ekdahl, C. T., Claasen, J. H., Bonde, S., Kokaia, Z., and Lindvall, O. (2011) Inflammation is detrimental for neurogenesis in adult brain. Proc Natl Acad Sci USA 100, 13632-13637.
84. Bialas, A. R., Presumey, J., Das, A., van der Poel, C. E., Lapchak, P. H., Mesin, L., Victora, G., Tsokos, G. C., Mawrin, C., Herbst, R., et al. (2017). Microglia-dependent synapse loss in type I interferon-mediated lupus. Nature Publishing Group 1-18.
85. Berg, vom, J., Prokop, S., Miller, K. R., Obst, J., lin, R. E. K. A., Lopategui-Cabezas, I., Wegner, A., Mair, F., Schipke, C. G., Peters, O., et al. (2012). Inhibition of IL-12/IL-23 signaling reduces Alzheimer's disease– like pathology and cognitive decline. Nature Medicine 18, 1812-1819.
86. Sevigny, J., Chiao, P., Bussière, T., Weinreb, P. H., Williams, L., Maier, M., Dunstan, R., Salloway, S., Chen, T., Ling, Y., et al. (2016). The antibody aducanumab reduces Aβ plaques in Alzheimer's disease. Nature Publishing Group 537, 50-56.
87. Parkhurst, C. N., Yang, G., Ninan, I., Savas, J. N., Yates, J. R.3., Lafaille, J. J., Hempstead, B. L., Littman, D. R., and Gan, W.-B. (2013). Microglia promote learning-dependent synapse formation through brain-derived neurotrophic factor. Cell 155, 1596-1609.
88. Vukovic, J., Colditz, M. J., Blackmore, D. G., Ruitenberg, M. J., and Bartlett, P. F. (2012). Microglia Modulate Hippocampal Neural Precursor Activity in Response to Exercise and Aging. Journal of Neuroscience 32, 6435-6443.
89. Battista, D., Ferrari, C. C., Gage, F. H., and Pitossi, F. J. (2006). Neurogenic niche modulation by activated microglia: transforming growth factor β increases neurogenesis in the adult dentate gyrus. European Journal of Neuroscience 23, 83-93.
90. Cole, A. J., Saffen, D. W., Baraban, J. M. & Worley, P. F. Rapid increase of an immediate early gene messenger RNA in hippocampal neurons by synaptic NMDA receptor activation. Nature 340, 474-476 (1989).
91. Alberini, C. M. (2009). Transcription Factors in Long-Term Memory and Synaptic Plasticity. Physiological Reviews 89, 121-145.
92. Villeda, S. A., Plambeck, K. E., Middeldorp, J., Castellano, J. M., Mosher, K. I., Luo, J., Smith, L. K., Bieri, G., Lin, K., Berdnik, D., et al. Young blood reverses age-related impairments in cognitive function and synaptic plasticity in mice. Nature Medicine 20, 659EP-.
93. Castellano, J. M., Mosher, K. I., Abbey, R. J., McBride, A. A., James, M. L., Berdnik, D., Shen, J. C., Zou, B., Xie, X. S., Tingle, M., et al. Human umbilical cord plasma proteins revitalize hippocampal function in aged mice. Nature 544, 488EP-.

94. Cronk, J. C., Filiano, A. J., Louveau, A., Marin, I., Marsh, R., Ji, E., Goldman, D. H., Smirnov, I., Geraci, N., Acton, S., et al. (2018). Peripherally derived macrophages can engraft the brain independent of irradiation and maintain an identity distinct from microglia. J Exp Med 215, 1627-1647.

95. Bennett, F. C., Bennett, M. L., Yaqoob, F., Mulinyawe, S. B., Grant, G. A., Gephart, M. H., Plowey, E. D., and Ben A Barres (2018). A Combination of Ontogeny and CNS Environment Establishes Microglial Identity. Neuron 1-23.

96. Li, Q., Cheng, Z., Zhou, L., Darmanis, S., Neff, N., Okamoto, J., Gulati, G., Bennett, M. L., Sun, L. O., Clarke, L. E., et al. (2018). Developmental heterogeneity of microglia and brain myeloid cells revealed by deep single-cell RNA sequencing. bioRxiv 406363.

97. Reemst, K., Noctor, S. C., Lucassen, P. J., and Hol, E. M. (2016). The Indispensable Roles of Microglia and Astrocytes during Brain Development. Front. Hum. Neurosci. 10, 15983-28.

98. Sardiello, M., Palmieri, M., di Ronza, A., Medina, D. L., Valenza, M., Gennarino, V. A., Di Malta, C., Donaudy, F., Embrione, V., Polishchuk, R. S., et al. (2009). A gene network regulating lysosomal biogenesis and function. Science 325, 473-477.

99. Settembre, C., De Cegli, R., Mansueto, G., Saha, P. K., Vetrini, F., Visvikis, O., Huynh, T., Carissimo, A., Palmer, D., Jurgen Klisch, T., et al. TFEB controls cellular lipid metabolism through a starvation-induced autoregulatory loop. Nat Cell Biol 15, 647EP-.

100. Pastore, N., Brady, O. A., Diab, H. I., Martina, J. A., Sun, L., Huynh, T., Lim, J.-A., Zare, H., Raben, N., Ballabio, A., et al. (2016). TFEB and TFE3 cooperate in the regulation of the innate immune response in activated macrophages. Autophagy 12, 1240-1258.

101. Rasmussen, M. K., Mestre, H., Nedergaard, M. (2018). The glymphatic pathway in neurological disorders. The Lancet Neurology 17, 1016-1024.

102. Da Mesquita, S., Louveau, A., Vaccari, A., Smirnov, I., Cornelison, R. C., Kingsmore, K. M., Contarino, C., Onengut-Gumuscu, S., Farber, E., Raper, D., et al. (2018). Functional aspects of meningeal lymphatics in ageing and Alzheimer's disease. Nature 560, 185-191.

103. Coughlin, S., Noviski, M., Mueller, J. L., Chuwonpad, A., Raschke, W. C., Weiss, A., and Zikherman, J. (2015). An extracatalytic function of CD45 in B cells is mediated by CD22. Proc Natl Acad Sci USA 112, E6515-E6524.

104. Freeman, S. A., Goyette, J., Furuya, W., Woods, E. C., Bertozzi, C. R., Bergmeier, W., Hinz, B., van der Merwe, P. A., Das, R., and Grinstein, S. (2016). Integrins Form an Expanding Diffusional Barrier that Coordinates Phagocytosis. Cell 164, 128-140.

105. Guerreiro, R., Wojtas, A., Bras, J., Carrasquillo, M., Rogaeva, E., Majounie, E., Cruchaga, C., Sassi, C., Kauwe, J. S. K., Younkin, S., et al. (2013). TREM2 Variants in Alzheimer's Disease. N Engl J Med 368, 117-127.

106. Jonsson, T., Stefansson, H., Steinberg, S., Jonsdottir, I., Jonsson, P. V., Snaedal, J., Bjornsson, S., Huttenlocher, J., Levey, A. I., Lah, J. J., et al. (2013). Variant of TREM2 Associated with the Risk of Alzheimer's Disease. N Engl J Med 368, 107-116.

107. Naj, A. C., Jun, G., Beecham, G. W., Wang, L.-S., Vardarajan, B. N., Buros, J., Gallins, P. J., Buxbaum, J. D., Jarvik, G. P., Crane, P. K., et al. (2011). Common variants at MS4A4/MS4A6E, CD2AP, CD33 and EPHA1 are associated with late-onset Alzheimer's disease. Nature Genetics 43, 436-441.

108. The Alzheimer's Disease Neuroimaging Initiative, CHARGE consortium, EADI1 consortium, Hollingworth, P., Harold, D., Sims, R., Gerrish, A., Lambert, J.-C., Carrasquillo, M. M., Abraham, R., et al. (2011). Common variants at ABCA7, MS4A6A/MS4A4E, EPHA1, CD33 and CD2AP are associated with Alzheimer's disease. Nature Genetics 43, 429-435.

109. Siddiqui, S. S., Springer, S. A., Verhagen, A., Sundaramurthy, V., Alisson-Silva, F., Jiang, W., Ghosh, P., and Varki, A. (2017). The Alzheimer's disease-protective CD33 splice variant mediates adaptive loss of function via diversion to an intracellular pool. J. Biol. Chem. 292, 15312-15320.

110. Huang, K.-L., Marcora, E., Pimenova, A. A., Di Narzo, A. F., Kapoor, M., Jin, S. C., Harari, O., Bertelsen, S., Fairfax, B. P., Czajkowski, J., et al. (2017). A common haplotype lowers PU.1 expression in myeloid cells and delays onset of Alzheimer's disease. Nat Neurosci 20, 1052-1061.

111. Sarlus, H., and Heneka, M. T. (2017). Microglia in Alzheimer's disease. J. Clin. Invest. 127, 3240-3249.

112. Li, M. D., Burns, T. C., Morgan, A. A., and Khatri, P. (2014). Integrated multi-cohort transcriptional meta-analysis of neurodegenerative diseases. Acta Neuropathol Commun 2, 1989-23.

113. Galatro, T. F., Holtman, I. R., Lerario, A. M., Vainchtein, I.D., Brouwer, N., Sola, P. R., Veras, M. M., Pereira, T. F., Leite, R. E. P., Möller, T., et al. (2017). Transcriptomic analysis of purified human cortical microglia reveals age-associated changes. Nat Neurosci 20, 1162-1171.

114. Zhang, Y., Sloan, S. A., Clarke, L. E., Caneda, C., Plaza, C. A., Blumenthal, P. D., Vogel, H., Steinberg, G. K., Edwards, M. S. B., Li, G., et al. (2016). Purification and Characterization of Progenitor and Mature Human Astrocytes Reveals Transcriptional and Functional Differences with Mouse. Neuron 89, 37-53.

115. MendanhaFalcao, A., Bruggen, D., Marques, S., Meijer, M., kel, S. J. X., Agirre, E., Samudyata, Floriddia, E. M., Vanichkina, D. P., ffrench-Constant, C., et al. (2018). Disease-specific oligodendrocyte lineage cells arise in multiple sclerosis. Nature Medicine 1-15.

116. Olah, M., Menon, V., Habib, N., Taga, M., Yung, C., Cimpean, M., Khairalla, A., Dionne, D., Hopp, S., Frosch, M. P., et al. (2018). A single cell-based atlas of human microglial states reveals associations with neurological disorders and histopathological features of the aging brain. bioRxiv 343780.

117. Chan, G., White, C. C., Winn, P. A., Cimpean, M., Replogle, J. M., Glick, L. R., Cuerdon, N. E., Ryan, K. J., Johnson, K. A., Schneider, J. A., et al. (2015). CD33 modulates TREM2: convergence of Alzheimer loci. Nat Neurosci 18, 1556-1558.

118. Park, J.-S., Ji, I. J., Kim, D.-H., An, H. J., and Yoon, S.-Y. (2017). The Alzheimer's Disease-Associated R47H Variant of TREM2 Has an Altered Glycosylation Pattern and Protein Stability. Front. Neurosci. 10, 26043-10.

119. Schwarz, F., Springer, S. A., Altheide, T. K., Varki, N. M., Gagneux, P., and Varki, A. (2016). Human-specific derived alleles of CD33 and other genes protect against postreproductive cognitive decline. Proc Natl Acad Sci USA 113, 74-79.

120. Cougnoux, A., Drummond, R. A., Collar, A. L., Iben, J. R., Salman, A., Westgarth, H., Wassif, C. A., Cawley, N.

X., Farhat, N. Y., Ozato, K., et al. (2018). Microglia activation in Niemann-Pick disease, type C1 is amendable to therapeutic intervention. Human Molecular Genetics 27, 2076-2089.
121. Funikov, S. Y., Rezvykh, A. P., Mazin, P. V., Morozov, A. V., Maltsev, A. V., Chicheva, M. M., Vikhareva, E. A., Evgen'ev, M. B., and Ustyugov, A. A. (2018). FUS(1-359) transgenic mice as a model of ALS: pathophysiological and molecular aspects of the proteinopathy. 1-16.
122. Xiao, H., Woods, E. C., Vukojicic, P., and Bertozzi, C. R. (2016). Precision glycocalyx editing as a strategy for cancer immunotherapy. Proc Natl Acad Sci USA 113, 10304-10309.
123. Bohlen, C. J., Bennett, F. C., and Bennett, M. L. (2018). Isolation and Culture of Microglia. Current Protocols in Immunology 339, e70-21.
124. Kelm, S., Pelz, A., Schauer, R., Filbin, M. T., Tang, S., Bellard, M.-E. de, Schnaar, R. L., Mahoney, J. A., Hartnell, A., Bradfield, P., et al. (1994). Sialoadhesin, myelin-associated glycoprotein and CD22 define a new family of sialic acid-dependent adhesion molecules of the immunoglobulin superfamily. Current Biology 4, 965-972.
125. Noguchi, Y., Kato, M., Ozeki, K., and Ishigai, M. (2017). Pharmacokinetics of an intra-cerebroventricularly administered antibody in rats. mAbs 9, 1210-1215.
126. Wolf, A., Bauer, B., Abner, E. L., Ashkenazy-Frolinger, T., and Hartz, A. M. S. (2016). A Comprehensive Behavioral Test Battery to Assess Learning and Memory in 12956/Tg2576 Mice. PLoS ONE 11, e0147733-23.
127. Larocca, J. N., and Norton, W. T. (2007). Isolation of myelin. Curr. Protoc. Cell Biol. Chapter 3, 25.
128. Stine, W. B., Jungbauer, L., Yu, C., and LaDu, M. J. (2010). Preparing Synthetic Aβ in Different Aggregation States. In Biological Microarrays, A. Khademhosseini, K.-Y. Suh, and M. Zourob, eds. (Totowa, N. J.: Humana Press), pp. 13-32.es Example 2—Anti-CD22 Antibodies Treat Niemann-Pick Disease Type C Niemann-Pick disease type C (NPC) is a rare autosomal recessive neurodegenerative disorder with an estimated prevalence of 1:100,000. Loss of function mutations in the NPC1 (~95% of cases) or NPC2 (~5% of cases) gene lead to the accumulation of unesterified cholesterol and glycolipids in the lysosomal/late endosomal system. The mutations manifest in neurological dysfunction and sometimes in liver, lung, or spleen dysfunction. Neurological complications are the overwhelming primary cause of death, and CNS-directed treatments have proven to be the most successful interventions in animal models to prolong lifespan and healthspan. Although the neurological symptoms of NPC were originally attributed to cholesterol dysregulation in neurons, recent studies highlight the importance of microglia in disease pathogenesis. Delivery of the WT NPC1 gene to glia[1], or crossing NPC1-/- mice to mice deficient in a microglia-specific transcriptional regulator of pro-inflammatory activation[2], markedly extends lifespan. These findings demonstrate that microglial dysfunction is a crucial participant in disease pathogenesis, and that microglia-directed therapies alter clinical manifestations of NPC, including mortality. Primary symptoms of NPC begin early in childhood, and include ataxia, dysarthria, vertical gaze palsy, sensorineural hearing loss, hypotonia, psychosis, and premature cognitive decline. For many patients, NPC leads to fatal complications in childhood, although late onset NPC is marked by the slow progression of symptoms into adulthood. Fatality is often the result of neurological sequelae, such as intractable epilepsy or aspiration pneumonia. There are no approved disease-modifying therapies for NPC. Conventional treatment is directed at symptom management.

Figure 40:
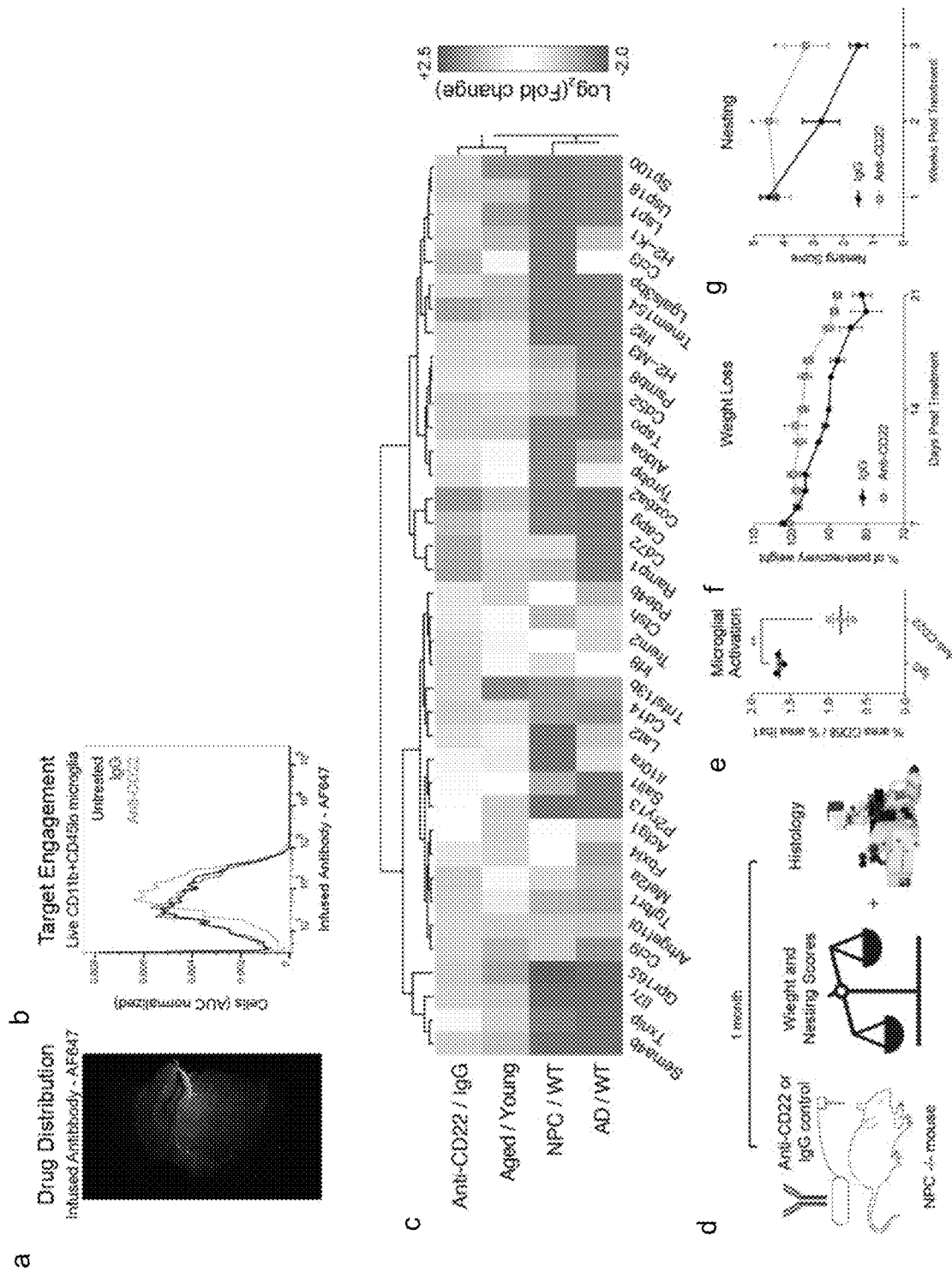
FIG. 40 shows that intrathecal CD22 antibodies improve cognitive function in aged mice and ameliorate disease in NPC1−/− mice. (a), Distribution of labeled antibody in parenchyma. (b), Flow analysis of microglia from mice infused with AF647-labeled IgG or anti-CD22 showing target engagement of the anti-CD22 antibody. (c), Hierarchically clustered heatmap of Log-2 normalized fold changes between microglia from anti-CD22 and IgG treated mice, aged and young mice, NPC1−/− and WT mice, and AD-model and age-matched WT mice. (d) Schematic of long-term CNS-targeted anti-CD22 treatment in NPC1−/− mice. (e), Microglial activation (CD68 reactivity) is reduced in anti-CD22 treated NPC1−/− mice. (f), Weight of NPC1−/− mice treated with IgG or anti-CD22. (g), Nesting scores NPC1−/− mice treated with IgG or anti-CD22.

In the course of development of the present invention, we've discovered that CD22 is upregulated and expressed on microglia in the NPC central nervous system, and sCD22 is a potential biomarker of NPC in human patients. Aging and disease overwhelm the homeostatic function of microglia, leading to a distinctive transcriptional state characterized by the downregulation of resting microglial signature genes and the upregulation of activated microglial signature genes, which code for pro-inflammatory molecules that cause neuronal death and contribute to premature cognitive decline in NPC. Because phagocytosis is a central homeostatic function of microglia, we tested whether CD22 blockade restores microglia to a homeostatic state. To do so, we implanted aged mice with osmotic pumps to continuously infuse a CD22 function-blocking antibody or an IgG control antibody directly into the cerebrospinal fluid for one month (FIG. 29a). We labeled the respective antibodies with a fluorescent dye to test drug distribution within the brain parenchyma (FIG. 40a) and target engagement with CD22 on microglia (FIG. 40b). Anti-CD22 treatment promoted the upregulation of homeostatic microglial signature genes and the downregulation of activated microglial signature genes, partially reversing the transcriptional hallmarks of aging and NPC (FIG. 40c). The therapeutic antibody ameliorates age-related cognitive decline as assessed by the Y-maze (FIG. 29e) and contextual fear conditioning (FIG. 29h) hippocampal-dependent memory paradigms, demonstrating the safety of targeting CD22 in the CNS.

CD22 functional blockade improves clinical outcomes in the NPC1-/- mouse model. To test the therapeutic potential of the anti-CD22 antibody, we implanted 4-week-old NPC1-/- mice with osmotic pumps to continuously infuse IgG or anti-CD22 directly into the CSF for one month (FIG. 40d). The infusion regimen extends from the onset of clinicopathological decline (at 4 weeks of age) to end-stage disease (at 8 weeks of age). The drug delivery route is consistent with intrathecal administration modalities currently used in NPC clinical trials. One month of CNS-targeted anti-CD22 treatment improved clinical measures including weight change (FIG. 40f) and behavioral outcomes such as nesting (FIG. 40g), an indicator of general well-being in mice. Mice were euthanized at 8-weeks-old to harvest tissues for transcriptomic and histological analyses. Anti-CD22 treatment reduced histological hallmarks of pro-inflammatory microglial activation in the NPC brain (FIG. 40e), demonstrating target-specific efficacy. These results indicate that delivery of an anti-CD22 antibody into the CNS leads to clinical, behavioral, and cognitive improvements in the relevant NPC disease models.

Figure 41:
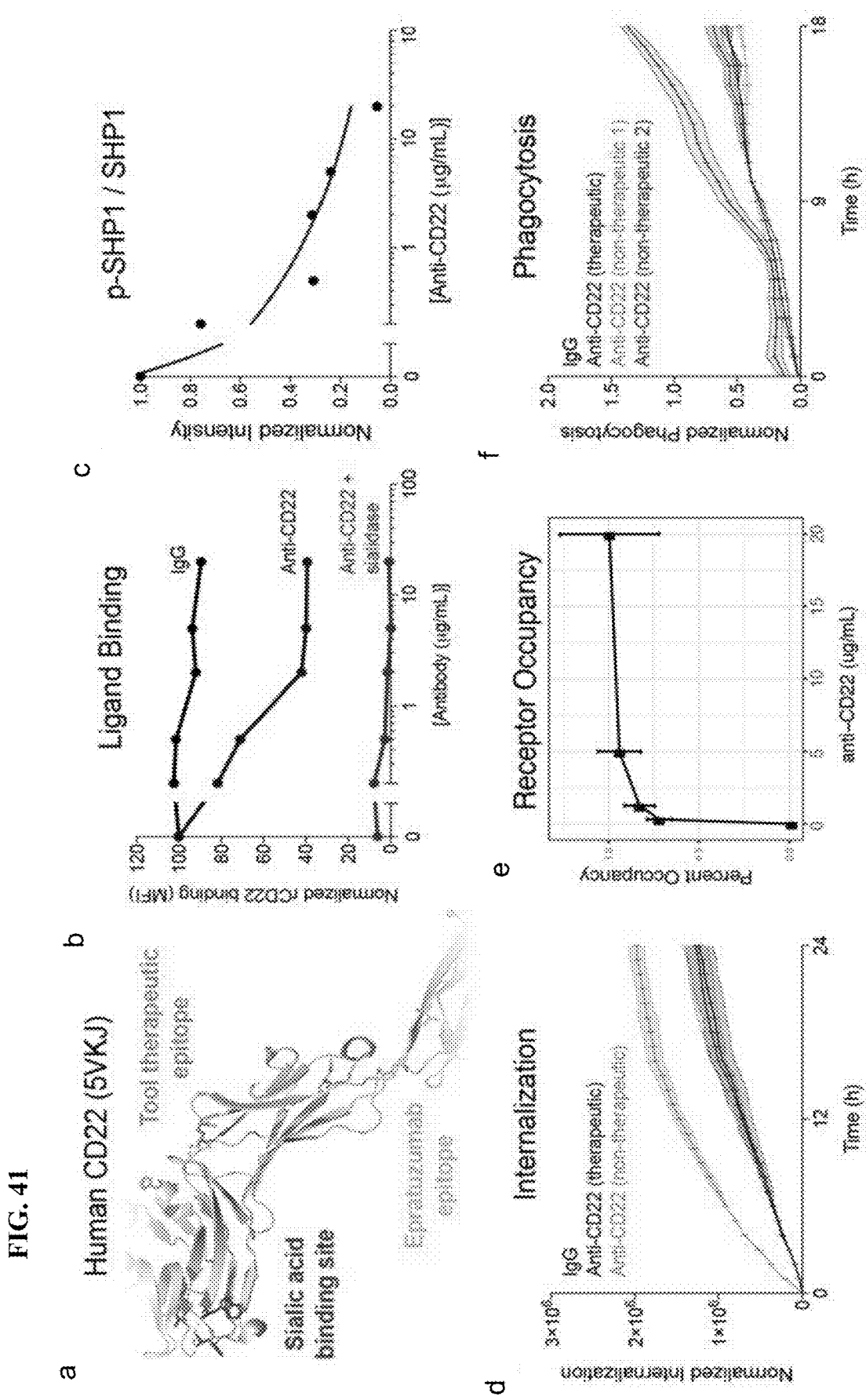
FIG. 41 shows functional properties of an anti-CD22 antibody. (a), Crystal structure of human CD22, highlighting ligand binding site (red), epratuzumab epitope (cyan), and the putative epitope of the anti-CD22 antibody (green). The anti-CD22 antibody blocks CD22 ligand binding, dependent on sialic acid. (c), Quantification of western blot assessing ratio of active pSHP1 to total SHP1 protein in BV2 cells pretreated with various concentrations of anti-CD22. Blue line represents the fitted variable slope inhibitor-response curve. (d), Internalization of IgG (black), therapeutic anti-CD22 antibody (blue), and non-therapeutic anti-CD22 antibody (green) conjugated to a pH-sensitive fluorescent dye by BV2 cells assessed by time-lapse microscopy. (e), The anti-CD22 antibody achieves full receptor occupancy at low concentrations. Comparing to pSHP1/SHP1 assay, <50% occupancy is necessary to achieve IC50. (f), In contrast to other CD22 antibodies, the therapeutic anti-CD22 antibody is only antibody provides a pro-phagocytic effect.

The crystal structures of CD22 in complex with its ligand, sialic acid, or with the FDA-approved antibody epratuzumab is provided in FIG. 41a[3,4] With this antibody, we've demonstrated CD22 binding and therapeutic effect in mice. Based on site-directed mutagenesis experiments, the antibody interacts amino acid residues H110, R139, and Q175 (FIG. 41a) to block ligand binding (FIG. 41b) and to reduce downstream inhibitory SHP-1 signaling in microglia (FIG. 41c). The epitope is in close proximity to, but does not overlap with, the ligand binding domain of CD22, yet displays potent ligand-blocking effects likely through steric hindrance. The antibody does not become internalized (FIG. 41d) and achieves full receptor occupancy at a low concentration (FIG. 41e). Other CD22 antibodies do not block ligand binding, evade internalization, and decrease inhibitory signaling simultaneously. The antibody binds a distinct epitope compared to known epitopes of existing CD22 antibodies (FIG. 41a). The characteristics of the anti-CD22 antibody correspond to its potent pro-phagocytic effect on microglia, distinguishing it from two non-therapeutic CD22 antibodies (FIG. 41f). These findings indicate that the anti-CD22 antibody's unique properties differentiate it from existing CD22 antibodies and are responsible for its therapeutic efficacy in NPC.

REFERENCES

1. Marshall C A, Watkins-Chow D E, Palladino G, Deutsch G, Chandran K, Pavan W J, Erickson R P. In Niemann-Pick C1 mouse models, glial-only expression of the normal gene extends survival much further than do changes in genetic background or treatment with hydroxypropyl-beta-cyclodextrin. Gene. 2018 Feb. 15; 643:117-123.
2. Cougnoux A, Drummond R A, Collar A L, Iben J R, Salman A, Westgarth H, Wassif C A, Cawley N X, Farhat N Y, Ozato K, Lionakis M S, Porter F D. Microglia activation in Niemann-Pick disease, type C1 is amendable to therapeutic intervention. Hum Mol Genet. 2018 Jun. 15; 27(12):2076-2089.
3. Ereño-Orbea J, Sicard T, Cui H, Mazhab-Jafari M T, Benlekbir S, Guarné A, Rubinstein J L, Julien J P. Molecular basis of human CD22 function and therapeutic targeting. Nat Commun. 2017 Oct. 2; 8(1):764
4. Zaccai N R, Maenaka K, Maenaka T, Crocker P R, Brossmer R, Kelm S, Jones E Y. Structure-guided design of sialic acid-based Siglec inhibitors and crystallographic analysis in complex with sialoadhesin. Structure. 2003 May; 11(5):557-67.

All publications and patents mentioned in the above specification are herein incorporated by reference. Various modifications and variations of the described method and system of the disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure that are obvious to those skilled relevant fields are intended to be within the scope of the following claims.

We claim:

1. A method of treating a neurodegenerative disease comprising: exposing one or more of a subject's microglia, macrophage and/or other phagocytic cells to an anti-CD22 antibody wherein said exposing treats said neurodegenerative disease wherein said neurodegenerative disease is Niemann-Pick disease Type C (NPC).

2. The method of claim 1, wherein said anti-CD22 antibody is administered by a method that bypasses and/or promotes transfer across the blood brain barrier, wherein said method that bypasses and/or promotes transfer across the blood brain barrier comprises one or more of direct application to the surface of the central nervous system, direct application to the parenchyma of the central nervous system, direct application to the ventricles of the central nervous system, and direct application to the cerebrospinal fluid of the central nervous system.

3. The method of claim 2, wherein said direct application to the cerebrospinal fluid of the central nervous system is selected from the group consisting of intrathecal administration and epidural administration.

4. The method of claim 3, wherein said intrathecal and epidural administration is selected from the group consisting of single shot administration, a series of single shot administrations, and continuous administration.

5. The method of claim 4, wherein said continuous administration comprises a programmable external pump.

6. The method of claim 4, wherein said continuous administration comprises a programmable implantable pump.

7. The method of claim 1, comprising assaying a microglia, macrophage and/or other phagocytic cell sample from said subject for CD22 expression.

* * * * *